US009238799B2

(12) United States Patent
Pletnev et al.

(10) Patent No.: US 9,238,799 B2
(45) Date of Patent: Jan. 19, 2016

(54) ANTIGENIC CHIMERIC TICK-BORNE ENCEPHALITIS VIRUS/DENGUE VIRUS TYPE 4 RECOMBINANT VIRUSES

(71) Applicant: The United States of America, as Represented by the Secretary of the Department of Health and Human Services, Washington, DC (US)

(72) Inventors: Alexander G. Pletnev, Gaithersburg, MD (US); Brian R. Murphy, Bethesda, MD (US); Amber R. Engel, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 106 days.

(21) Appl. No.: 14/014,920

(22) Filed: Aug. 30, 2013

(65) Prior Publication Data

US 2014/0004147 A1  Jan. 2, 2014

Related U.S. Application Data

(62) Division of application No. 13/322,317, filed as application No. PCT/US2010/036678 on May 28, 2010, now Pat. No. 8,568,739.

(60) Provisional application No. 61/181,982, filed on May 28, 2009.

(51) Int. Cl.
  *C12N 7/00*   (2006.01)
  *A61K 39/12*  (2006.01)
  *C12N 7/01*   (2006.01)
  *A61K 39/00*  (2006.01)

(52) U.S. Cl.
  CPC . *C12N 7/00* (2013.01); *A61K 39/12* (2013.01); *A61K 2039/5254* (2013.01); *A61K 2039/5256* (2013.10); *A61K 2039/70* (2013.01); *C12N 2770/24134* (2013.01); *C12N 2770/24151* (2013.01)

(58) Field of Classification Search
  CPC .................. A61K 39/295; C12N 7/00; C12N 2770/24162; C12N 7/10011; C12N 2770/24011; C12N 2770/24111; C12N 2800/22; C12N 7/06; G01N 2333/18
  See application file for complete search history.

(56) References Cited

U.S. PATENT DOCUMENTS 6,184,024 B1   2/2001  Lai et al.
6,497,884 B1  12/2002  Pletnev et al.
7,094,411 B2   8/2006  Kinney et al.
2004/0223979 A1  11/2004  Chambers et al.
2009/0155301 A1   6/2009  Mason et al.
2009/0324623 A1  12/2009  Frolov et al.

FOREIGN PATENT DOCUMENTS

WO   WO 2008/157136   12/2008

OTHER PUBLICATIONS

Engel et al., "Amino acid substitutions within E and NS5 proteins attenuate the chimeric TBEV/DEN virus for neurovirulence in suckling mice," Abstract, American Society for Virology Annual Conference, 2007 (1 page).
Engel et al., "Attenuation of neurovirulence in suckling mice by introduction of amino acid substitutions within E and NS5 proteins of the chimeric TBEV/DEN virus," Abstract, Eighth International Symposium on positive-strand RNA viruses, 2007 (1 page).
Engel et al., "Attenuation of chimeric TBE/DEN virus neurovirulence for suckling mice by introduction of amino acid substitutions within E and NS5 proteins," Poster, International Congress on Virology, 2008 (1 page).
Engel et al., "Attenuation of chimeric TBE/DEN virus neurovirulence for suckling mice by introduction of amino acid substitutions within E and NS5 proteins," Poster, NIH Fellows Award for Research Excellence Conference, 2008 (1 page).
Engel et al., "The neurovirulence and neuroinvasiveness of chimeric tick-borne encephalitis/dengue virus can be attenuated by introducing defined mutations into the envelope and NS5 protein genes and the 3' non-coding region of the genome," *Virology*, vol. 405, No. 1, pp. 243-252, 2010.
Hanley et al., "Paired Charge-to-Alanine Mutagenesis of Dengue Virus Type 4 NS5 Generates Mutants with Temperature-Sensitive, Host Range, and Mouse Attenuation Phenotypes," *Journal of Virology*, vol. 76, No. 2, pp. 525-531, 2002.
Lai et al., "Infectious RNA transcribed from stably cloned full-length cDNA of dengue type 4 virus," *Proc. Natl. Acad. Sci. USA*, vol. 88, pp. 5139-5143, 1991.
Levenbook et al., "Neuropathogenesis and Neurovirulence of Live Flaviviral Vaccines in Monkey," *Journal of Virology*, vol. 83, No. 10, pp. 5289-5292, 2009.

(Continued)

*Primary Examiner* — Bao Li
(74) *Attorney, Agent, or Firm* — Klarquist Sparkman, LLP

(57) ABSTRACT

Disclosed herein are chimeric TBEV/DEN4 flaviviruses including a first nucleic acid molecule including a 5' non-coding region (NCR) from a DEN4 virus, a nucleic acid encoding a C protein and non-structural proteins from a DEN4 virus, and a 3' NCR from a DEN4 virus, wherein nonstructural protein NS4B includes a phenylalanine at amino acid position 112, nonstructural protein NS5 includes an alanine at amino acid position 654 and an alanine at amino acid position 655, and the 3' NCR includes a deletion of nucleotides 10478-10507. The chimeric construct also includes a second nucleic acid molecule, which is operably linked to the first nucleic acid molecule, encoding a prM protein and an E protein from a TBEV, wherein the E protein includes an amino acid substitution that differs from the wild type TBEV at amino acid position 315 and a tryptophan at amino acid position 240. Also disclosed are methods of eliciting an immune response using the disclosed TBEV/DEN4 chimeric flaviviruses and immunogenic compositions including the disclosed chimeric flaviviruses and a pharmaceutically acceptable carrier.

14 Claims, 9 Drawing Sheets

(56) References Cited

OTHER PUBLICATIONS

Maximova et al., "Comparative Neuropathogenesis and Neurovirulence of Attenuated Flaviviruses in Nonhuman Primates," *Journal of Virology*, vol. 82, No. 11, pp. 5255-5268, 2008.

Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," *Journal of Virology*, vol. 70, No. 6, pp. 3930-3937, 1996.

Mandl, "Steps of the tick-borne encephalitis virus replication cycle that affect neuropathogenesis," *Virus Research*, vol. 111, No. 2, pp. 161-174, 2005.

Pletnev et al., "Construction and characterization of chimeric tick-borne encephalitis/dengue type 4 viruses," *Proc. Natl. Acad. Sci. USA*, vol. 89, pp. 10532-10536, 1992.

Pletnev et al., "Chimeric Tick-Borne Encephalitis and Dengue Type 4 Viruses: Effects of Mutations on Neurovirulence in Mice," *Journal of Virology*, vol. 67, No. 8, pp. 4956-4963, 1993.

Pletnev et al., "Tick-Borne Langat/Mosquito-Borne Dengue Flavivirus Chimera, a Candidate Live Attenuated Vaccine for Protection against Disease Caused by Members of the Tick-Borne Encephalitis Virus Complex: Evaluation in Rhesus Monkeys and in Mosquitoes," *Journal of Virology*, vol. 75, No. 17, pp. 8259-8267, 2001.

Pletnev et al., "West Nile virus/dengue type 4 virus chimeras that are reduced in neurovirulence and peripheral virulence without loss of immunogenicity or protective efficacy," *Proc. Natl. Acad. Sci. USA*, vol. 99, No. 5, pp. 3036-3041, 2002.

Rumyantsev et al., "A Tick-Borne Langat Virus Mutant That Is Temperature Sensitive and Host Range Restricted in Neuroblastoma Cells and Lacks Neuroinvasiveness for Immunodeficient Mice," *Journal of Virology*, vol. 80, No. 3, pp. 1427-1439, 2006.

Rumyantsev et al., "Comparison of live and inactivated tick-borne encephalitis virus vaccines for safety, immunogenicity and efficacy in rhesus monkeys," *Vaccine*, vol. 24, pp. 133-143, 2006.

Suzuki et al., "Construction and Characterization of a Single-Cycle Chimeric Flavivirus Vaccine Candidate That Protects Mice against Lethal Challenge with Dengue Virus Type 2," *Journal of Virology*, vol. 83, No. 4, pp. 1870-1880, 2009.

Taucher et al., "A *trans*-Complementing Recombination Trap Demonstrates a Low Propensity of Flaviviruses for Intermolecular Recombination," *Journal of Virology*, vol. 84, No. 1, pp. 599-611, 2010.

Widman et al., "Third-Generation Flavivirus Vaccines Based on Single-Cycle, Encapsidation-Defective Viruses," *Advances in Virus Research*, vol. 72, pp. 77-126, 2008.

Widman et al., "RepliVAX WN, a single-cycle flavivirus vaccine to prevent West Nile disease, elicits durable protective immunity in hamsters," *Vaccine*, vol. 27, pp. 5550-5553, 2009.

Wright et al., "Evaluation of the Langat/dengue 4 chimeric virus as a live attenuated tick-borne encephalitis vaccine for safety and immunogenicity in healthy adult volunteer," *Vaccine*, vol. 26, No. 7, pp. 882-890, 2008.

FIG. 1

Replication in Vero cells

Replication in SHSY-5Y cells

Replication in LN-18 cells

FIG. 2A

Viral kinetics in the brains of 3 day-old Swiss mice

- TBEV/DEN4Δ30
- TBEV/DEN4Δ30/E-315
- TBEV/DEN4Δ30/NS5-654,655
- TBEV/DEN4Δ30/E-315/NS5-654,655

Y-axis: Viral titer (log10 pfu/ml)
X-axis: Days post-inoculation

FIG. 2B

Viral kinetics in the brains of 5 day-old Swiss mice

- TBE/DEN4Δ30
- TBE/DEN4Δ30/E-315
- TBE/DEN4Δ30/NS5-654,655
- TBE/DEN4Δ30/E-315/NS5-654,655

Y-axis: Viral titer (log10 pfu/g)
X-axis: Days post-inoculation

FIG. 3A
TBEV/DEN4

FIG. 3B
TBEV/DEN4Δ30

Viral replication kinetics in Vero cells

- TBEV/DEN4Δ30
- TBEV/DEN4Δ30/E-$K_{315}D$
- TBEV/DEN4Δ30/NS5-$DR_{654,655}AA$
- TBEV/DEN4Δ30/E-$K_{315}D$/NS5-$DR_{654,655}AA$
- LGT
- DEN4

FIG. 7B

Viral replication kinetics in C6/36 cells

- TBEV/DEN4Δ30
- TBEV/DEN4Δ30/E-$K_{315}D$
- TBEV/DEN4Δ30/NS5-$DR_{654,655}AA$
- TBEV/DEN4Δ30/E-$K_{315}D$/NS5-$DR_{654,655}AA$
- LGT
- DEN4

FIG. 9B ial Patent Application No. 61/181,982, filed May 28,

SEQUENCE LISTING

<160> NUMBER OF SEQ ID NOS: 27

<210> SEQ ID NO 1
<211> LENGTH: 10633

<212> TYPE: DNA
<213> ORGANISM: Artificial Sequence
<220> FEATURE:
<223> OTHER INFORMATION: Chimeric TBEV/Den
      4-delta30/E-K315D/E-R240W/NS4B-L112F/NS5-DR654,655AA
<220> FEATURE:
<221> NAME/KEY: CDS
<222> LOCATION: (102)..(10280)

<400> SEQUENCE: 1

```
agttgttagt ctgtgtggac cgacaaggac agttccaaat cggaagcttg cttaacacag    60
ttctaacagt ttgtttgaat agagagcaga tctctggaaa a atg aac caa cga aaa   116
                                              Met Asn Gln Arg Lys
                                                1               5 aag gtg gtt aga cca cct ttc aat atg ctg aaa cgc gag aga aac cgc     164
Lys Val Val Arg Pro Pro Phe Asn Met Leu Lys Arg Glu Arg Asn Arg
             10              15                  20 gta tca acc cct caa ggg ttg gtg aag aga ttc tca acc gga ctt ttt    212
Val Ser Thr Pro Gln Gly Leu Val Lys Arg Phe Ser Thr Gly Leu Phe
         25                  30                  35 tct ggg aaa gga ccc tta cgg atg gtg cta gca ttc atc acg ttt ttg    260
Ser Gly Lys Gly Pro Leu Arg Met Val Leu Ala Phe Ile Thr Phe Leu
     40                  45                  50 cga gtc ctt tcc atc cca cca aca gca ggg att ctg aag aga tgg gga    308
Arg Val Leu Ser Ile Pro Pro Thr Ala Gly Ile Leu Lys Arg Trp Gly
 55                  60                  65 cag ttg aag aaa aat aag gcc atc aag ata ctg att gga ttc agg aag    356
Gln Leu Lys Lys Asn Lys Ala Ile Lys Ile Leu Ile Gly Phe Arg Lys
70                  75                  80                  85 gag ata ggc cgc atg ctg aac atc ttg aac ggg aga aaa agg tct gca    404
Glu Ile Gly Arg Met Leu Asn Ile Leu Asn Gly Arg Lys Arg Ser Ala
                 90                  95                 100 gta gac tgg aca ggt tgg ttg ctg gtt gtt gtc ctg ttg gga gtg aca    452
Val Asp Trp Thr Gly Trp Leu Leu Val Val Val Leu Leu Gly Val Thr
            105                 110                 115 ctt gca gcc aca gtg cgg aag gaa aga gat ggc acc acc gtg atc aga    500
Leu Ala Ala Thr Val Arg Lys Glu Arg Asp Gly Thr Thr Val Ile Arg
        120                 125                 130 gct gaa gga aaa gat gcg gca acc cag gtg cgt gtg gaa aat ggc acc    548
Ala Glu Gly Lys Asp Ala Ala Thr Gln Val Arg Val Glu Asn Gly Thr
135                 140                 145 tgt gtg atc ctg gcc acg gac atg gga tca tgg tgt gat gat tca cta    596
Cys Val Ile Leu Ala Thr Asp Met Gly Ser Trp Cys Asp Asp Ser Leu
150                 155                 160                 165 acc tat gag tgt gtg acc ata gac cag ggg gag gaa ccg gtt gac gtg    644
Thr Tyr Glu Cys Val Thr Ile Asp Gln Gly Glu Glu Pro Val Asp Val
                170                 175                 180 gat tgc ttt tgc agg aat gtt gat gga gtt tac ctg gag tat ggg cgg    692
Asp Cys Phe Cys Arg Asn Val Asp Gly Val Tyr Leu Glu Tyr Gly Arg
            185                 190                 195 tgt gga aaa caa gaa gga tca aga aca agg cgt tca gtg ctg atc cca    740
Cys Gly Lys Gln Glu Gly Ser Arg Thr Arg Arg Ser Val Leu Ile Pro
        200                 205                 210 tcc cac gct cag gga gat ctc aca gga agg gga cac aaa tgg tta gaa    788
Ser His Ala Gln Gly Asp Leu Thr Gly Arg Gly His Lys Trp Leu Glu
215                 220                 225 ggg gat tca tta cgg acg cac ctc act aga gtt gag gga tgg gtc tgg    836
Gly Asp Ser Leu Arg Thr His Leu Thr Arg Val Glu Gly Trp Val Trp
230                 235                 240                 245 aag aat aaa gtg ctc acc ctg gcg gtg atc gcc gtt gtg tgg ctg acc    884
Lys Asn Lys Val Leu Thr Leu Ala Val Ile Ala Val Val Trp Leu Thr
```

-continued

| | | | | | | | | | | | | |
|---|---|---|---|---|---|---|---|---|---|---|---|---|
| | | | 250 | | | | 255 | | | | 260 | |
| gtg | gaa | agt | gtg | gtg | act | cgg | gtc | gcc | gta | gtg | gtg | gtg ctc ttg tgc | 932
| Val | Glu | Ser | Val | Val | Thr | Arg | Val | Ala | Val | Val | Val | Val Leu Leu Cys |
| | | | 265 | | | | 270 | | | | 275 | |

| ctg gct ccg gtt tat gcc tca cgg tgc aca cat ttg gaa aac agg gat | 980
| Leu Ala Pro Val Tyr Ala Ser Arg Cys Thr His Leu Glu Asn Arg Asp |
| 280 285 290 |

| ttt gtt act ggc act cag ggg acc act cgt gtg act ctg gtt ttg gaa | 1028
| Phe Val Thr Gly Thr Gln Gly Thr Thr Arg Val Thr Leu Val Leu Glu |
| 295 300 305 |

| ctg gga gga tgc gtc acc ata aca gct gag ggg aag ccc tcg atg gat | 1076
| Leu Gly Gly Cys Val Thr Ile Thr Ala Glu Gly Lys Pro Ser Met Asp |
| 310 315 320 325 |

| gtg tgg ctt gac tcc atc tac cag gag aac cct gcc aag aca cgt gag | 1124
| Val Trp Leu Asp Ser Ile Tyr Gln Glu Asn Pro Ala Lys Thr Arg Glu |
| 330 335 340 |

| tac tgc ctt cac gca aaa cta tcg gat acc aaa gtc gcg gcc agg tgc | 1172
| Tyr Cys Leu His Ala Lys Leu Ser Asp Thr Lys Val Ala Ala Arg Cys |
| 345 350 355 |

| cca aca atg gga cct gcc act ttg gct gaa gag cac cag agc ggc aca | 1220
| Pro Thr Met Gly Pro Ala Thr Leu Ala Glu Glu His Gln Ser Gly Thr |
| 360 365 370 |

| gtg tgt aag aga gac cag agt gat cga ggc tgg ggc aac cat tgt gga | 1268
| Val Cys Lys Arg Asp Gln Ser Asp Arg Gly Trp Gly Asn His Cys Gly |
| 375 380 385 |

| tta ttt gga aaa ggc agc att gtg acc tgt gtc aag gcg tct tgt gag | 1316
| Leu Phe Gly Lys Gly Ser Ile Val Thr Cys Val Lys Ala Ser Cys Glu |
| 390 395 400 405 |

| gca aaa aag aaa gcc aca gga cac gtg tat gac gct aac aaa att gtg | 1364
| Ala Lys Lys Lys Ala Thr Gly His Val Tyr Asp Ala Asn Lys Ile Val |
| 410 415 420 |

| tac aca gtc aaa gta gag ccg cac acg ggg gat tac gtc gct gct aat | 1412
| Tyr Thr Val Lys Val Glu Pro His Thr Gly Asp Tyr Val Ala Ala Asn |
| 425 430 435 |

| gag act cac agt gga aga aaa acc gcg tcc ttc acg gtt tcc tcg gag | 1460
| Glu Thr His Ser Gly Arg Lys Thr Ala Ser Phe Thr Val Ser Ser Glu |
| 440 445 450 |

| agg acc atc ttg acc atg gga gac tac gga gac gtg tcc ttg tta tgc | 1508
| Arg Thr Ile Leu Thr Met Gly Asp Tyr Gly Asp Val Ser Leu Leu Cys |
| 455 460 465 |

| aga gta gcc agc ggt gtt gac ctt gct cag acc gtc atc ctg gag ctt | 1556
| Arg Val Ala Ser Gly Val Asp Leu Ala Gln Thr Val Ile Leu Glu Leu |
| 470 475 480 485 |

| gac aag acc tca gaa cac cta ccg acg gcc tgg cag gtc cac cgg gac | 1604
| Asp Lys Thr Ser Glu His Leu Pro Thr Ala Trp Gln Val His Arg Asp |
| 490 495 500 |

| tgg ttc aat gat ctg gcc cta ccg tgg aaa cat gaa ggg gca cag aat | 1652
| Trp Phe Asn Asp Leu Ala Leu Pro Trp Lys His Glu Gly Ala Gln Asn |
| 505 510 515 |

| tgg aac aac gcg gaa tgg ctg gtt gag ttt gga gct cca cat gct gtg | 1700
| Trp Asn Asn Ala Glu Trp Leu Val Glu Phe Gly Ala Pro His Ala Val |
| 520 525 530 |

| aaa atg gac gtg tac aac ctt gga gac cag act gga gtg ttg ctc aaa | 1748
| Lys Met Asp Val Tyr Asn Leu Gly Asp Gln Thr Gly Val Leu Leu Lys |
| 535 540 545 |

| tca ctt gct ggt gtt cct gtg gcg cac att gat gga acc aag tac cac | 1796
| Ser Leu Ala Gly Val Pro Val Ala His Ile Asp Gly Thr Lys Tyr His |
| 550 555 560 565 |

| ctg aaa agt ggc cac gtg aca tgc gag gta gga cta gaa aaa ctt aag | 1844

```
Leu Lys Ser Gly His Val Thr Cys Glu Val Gly Leu Glu Lys Leu Lys
                570             575                 580 atg aaa ggt ctt aca tac aca atg tgt gac aag acg aaa ttc acg tgg    1892
Met Lys Gly Leu Thr Tyr Thr Met Cys Asp Lys Thr Lys Phe Thr Trp
            585                 590                 595 gac aga att cca aca gac agt gga cat gac aca gtg gtc atg gaa gtt    1940
Asp Arg Ile Pro Thr Asp Ser Gly His Asp Thr Val Val Met Glu Val
                600                 605                 610 gcg ttc tct ggg acc aaa ccc tgc agg atc ccg gtg agg gcc gtg gca    1988
Ala Phe Ser Gly Thr Lys Pro Cys Arg Ile Pro Val Arg Ala Val Ala
        615                 620                 625 cac ggc tcc ccg gat gtg aac gtg gcc atg ttg ata aca ccc aac ccc    2036
His Gly Ser Pro Asp Val Asn Val Ala Met Leu Ile Thr Pro Asn Pro
    630                 635                 640                 645 aca atc gaa aac aat ggc ggt ggc ttc ata gaa atg cag tta cct cca    2084
Thr Ile Glu Asn Asn Gly Gly Gly Phe Ile Glu Met Gln Leu Pro Pro
                650                 655                 660 gga gat aat atc atc tat gtt ggg gaa ctg agt cac caa tgg ttc caa    2132
Gly Asp Asn Ile Ile Tyr Val Gly Glu Leu Ser His Gln Trp Phe Gln
            665                 670                 675 aaa ggg agt agc att gga agg gtt ttt caa aaa acc aga aaa ggc ata    2180
Lys Gly Ser Ser Ile Gly Arg Val Phe Gln Lys Thr Arg Lys Gly Ile
        680                 685                 690 gaa agg ctg aca gtg atc gga gaa cat gcc tgg gat ttt ggc tct act    2228
Glu Arg Leu Thr Val Ile Gly Glu His Ala Trp Asp Phe Gly Ser Thr
    695                 700                 705 ggt ggt ttc ctg acc tcg gtt ggt aag gcg ctg cac aca gtt ctt ggc    2276
Gly Gly Phe Leu Thr Ser Val Gly Lys Ala Leu His Thr Val Leu Gly
710                 715                 720                 725 ggt gcc ttt aac agc ctt ttt gga gga gtg ggg ttc ttg ccc aag atc    2324
Gly Ala Phe Asn Ser Leu Phe Gly Gly Val Gly Phe Leu Pro Lys Ile
                730                 735                 740 cta gtg gga gtg gtc ctg gcc tgg ttg ggc ctg aac tcg agg aac act    2372
Leu Val Gly Val Val Leu Ala Trp Leu Gly Leu Asn Ser Arg Asn Thr
            745                 750                 755 tca atg gct atg acg tgc ata gct gtt gga gga atc act ctg ttt ctg    2420
Ser Met Ala Met Thr Cys Ile Ala Val Gly Gly Ile Thr Leu Phe Leu
        760                 765                 770 ggc ttc aca gtt caa gca gac atg ggt tgt gtg gcg tca tgg agt ggg    2468
Gly Phe Thr Val Gln Ala Asp Met Gly Cys Val Ala Ser Trp Ser Gly
    775                 780                 785 aaa gaa ttg aag tgt gga agc gga att ttt gtg gtt gac aac gtg cac    2516
Lys Glu Leu Lys Cys Gly Ser Gly Ile Phe Val Val Asp Asn Val His
790                 795                 800                 805 act tgg aca gaa cag tac aaa ttt caa cca gag tcc cca gcg aga cta    2564
Thr Trp Thr Glu Gln Tyr Lys Phe Gln Pro Glu Ser Pro Ala Arg Leu
                810                 815                 820 gcg tct gca ata tta aat gcc cac aaa gat ggg gtc tgt gga att aga    2612
Ala Ser Ala Ile Leu Asn Ala His Lys Asp Gly Val Cys Gly Ile Arg
            825                 830                 835 tca acc acg agg ctg gaa aat gtc atg tgg aag caa ata acc aac gag    2660
Ser Thr Thr Arg Leu Glu Asn Val Met Trp Lys Gln Ile Thr Asn Glu
        840                 845                 850 cta aac tat gtt ctc tgg gaa gga gga cat gac ctc act gta gtg gct    2708
Leu Asn Tyr Val Leu Trp Glu Gly Gly His Asp Leu Thr Val Val Ala
    855                 860                 865 ggg gat gtg aag ggg gtg ttg acc aaa ggc aag aga gca ctc aca ccc    2756
Gly Asp Val Lys Gly Val Leu Thr Lys Gly Lys Arg Ala Leu Thr Pro
870                 875                 880                 885
```

|     |     |
| --- | --- |
| cca gtg agt gat ctg aaa tat tca tgg aag aca tgg gga aaa gca aaa<br>Pro Val Ser Asp Leu Lys Tyr Ser Trp Lys Thr Trp Gly Lys Ala Lys<br>            890                 895                 900 | 2804 |
| atc ttc acc cca gaa gca aga aat agc aca ttt tta ata gac gga cca<br>Ile Phe Thr Pro Glu Ala Arg Asn Ser Thr Phe Leu Ile Asp Gly Pro<br>        905                 910                 915 | 2852 |
| gac acc tct gaa tgc ccc aat gaa cga aga gca tgg aac tct ctt gag<br>Asp Thr Ser Glu Cys Pro Asn Glu Arg Arg Ala Trp Asn Ser Leu Glu<br>    920                 925                 930 | 2900 |
| gtg gaa gac tat gga ttt ggc atg ttc acg acc aac ata tgg atg aaa<br>Val Glu Asp Tyr Gly Phe Gly Met Phe Thr Thr Asn Ile Trp Met Lys<br>935                 940                 945 | 2948 |
| ttc cga gaa gga agt tca gaa gtg tgt gac cac agg tta atg tca gct<br>Phe Arg Glu Gly Ser Ser Glu Val Cys Asp His Arg Leu Met Ser Ala<br>950                 955                 960                 965 | 2996 |
| gca att aaa gat cag aaa gct gtg cat gct gac atg ggt tat tgg ata<br>Ala Ile Lys Asp Gln Lys Ala Val His Ala Asp Met Gly Tyr Trp Ile<br>            970                 975                 980 | 3044 |
| gag agc tca aaa aac cag acc tgg cag ata gag aaa gca tct ctt att<br>Glu Ser Ser Lys Asn Gln Thr Trp Gln Ile Glu Lys Ala Ser Leu Ile<br>        985                 990                 995 | 3092 |
| gaa gtg aaa aca tgt ctg tgg ccc aag acc cac aca ctg tgg agc<br>Glu Val Lys Thr Cys Leu Trp Pro Lys Thr His Thr Leu Trp Ser<br>    1000                1005                1010 | 3137 |
| aat gga gtg ctg gaa agc cag atg ctc att cca aaa tca tat gcg<br>Asn Gly Val Leu Glu Ser Gln Met Leu Ile Pro Lys Ser Tyr Ala<br>1015                1020                1025 | 3182 |
| ggc cct ttt tca cag cac aat tac cgc cag ggc tat gcc acg caa<br>Gly Pro Phe Ser Gln His Asn Tyr Arg Gln Gly Tyr Ala Thr Gln<br>1030                1035                1040 | 3227 |
| acc gtg ggc cca tgg cac tta ggc aaa tta gag ata gac ttt gga<br>Thr Val Gly Pro Trp His Leu Gly Lys Leu Glu Ile Asp Phe Gly<br>1045                1050                1055 | 3272 |
| gaa tgc ccc gga aca aca gtc aca att cag gag gat tgt gac cat<br>Glu Cys Pro Gly Thr Thr Val Thr Ile Gln Glu Asp Cys Asp His<br>1060                1065                1070 | 3317 |
| aga ggc cca tct ttg agg acc acc act gca tct gga aaa cta gtc<br>Arg Gly Pro Ser Leu Arg Thr Thr Thr Ala Ser Gly Lys Leu Val<br>1075                1080                1085 | 3362 |
| acg caa tgg tgc tgc cgc tcc tgc acg atg cct ccc tta agg ttc<br>Thr Gln Trp Cys Cys Arg Ser Cys Thr Met Pro Pro Leu Arg Phe<br>1090                1095                1100 | 3407 |
| ttg gga gaa gat ggg tgc tgg tat ggg atg gag att agg ccc ttg<br>Leu Gly Glu Asp Gly Cys Trp Tyr Gly Met Glu Ile Arg Pro Leu<br>1105                1110                1115 | 3452 |
| agt gaa aaa gaa gag aac atg gtc aaa tca cag gtg acg gcc gga<br>Ser Glu Lys Glu Glu Asn Met Val Lys Ser Gln Val Thr Ala Gly<br>1120                1125                1130 | 3497 |
| cag ggc aca tca gaa act ttt tct atg ggt ctg ttg tgc ctg acc<br>Gln Gly Thr Ser Glu Thr Phe Ser Met Gly Leu Leu Cys Leu Thr<br>1135                1140                1145 | 3542 |
| ttg ttt gtg gaa gaa tgc ttg agg aga aga gtc act agg aaa cac<br>Leu Phe Val Glu Glu Cys Leu Arg Arg Arg Val Thr Arg Lys His<br>1150                1155                1160 | 3587 |
| atg ata tta gtt gtg gtg atc act ctt tgt gct atc atc ctg gga<br>Met Ile Leu Val Val Val Ile Thr Leu Cys Ala Ile Ile Leu Gly<br>1165                1170                1175 | 3632 |
| ggc ctc aca tgg atg gac tta cta cga gcc ctc atc atg ttg ggg<br>Gly Leu Thr Trp Met Asp Leu Leu Arg Ala Leu Ile Met Leu Gly<br>1180                1185                1190 | 3677 |

-continued

| | | | | | | | | | | | | | | |
|---|---|---|---|---|---|---|---|---|---|---|---|---|---|---|
| gac | act | atg | tct | ggt | aga | ata | gga | gga | cag | atc | cac | cta | gcc | atc | 3722 |
| Asp | Thr | Met | Ser | Gly | Arg | Ile | Gly | Gly | Gln | Ile | His | Leu | Ala | Ile | |
| | | 1195 | | | | 1200 | | | | 1205 | | | | | | atg gca gtg ttc aag atg tca cca gga tac gtg ctg ggt gtg ttt      3767
Met Ala Val Phe Lys Met Ser Pro Gly Tyr Val Leu Gly Val Phe
        1210            1215            1220 tta agg aaa ctc act tca aga gag aca gca cta atg gta ata gga      3812
Leu Arg Lys Leu Thr Ser Arg Glu Thr Ala Leu Met Val Ile Gly
    1225            1230            1235 atg gcc atg aca acg gtg ctt tca att cca cat gac ctt atg gaa      3857
Met Ala Met Thr Thr Val Leu Ser Ile Pro His Asp Leu Met Glu
1240            1245            1250 ctc att gat gga ata tca ctg gga cta att ttg cta aaa ata gta      3902
Leu Ile Asp Gly Ile Ser Leu Gly Leu Ile Leu Leu Lys Ile Val
        1255            1260            1265 aca cag ttt gac aac acc caa gtg gga acc tta gct ctt tcc ttg      3947
Thr Gln Phe Asp Asn Thr Gln Val Gly Thr Leu Ala Leu Ser Leu
    1270            1275            1280 act ttc ata aga tca aca atg cca ttg gtc atg gct tgg agg acc      3992
Thr Phe Ile Arg Ser Thr Met Pro Leu Val Met Ala Trp Arg Thr
1285            1290            1295 att atg gct gtg ttg ttt gtg gtc aca ctc att cct ttg tgc agg      4037
Ile Met Ala Val Leu Phe Val Val Thr Leu Ile Pro Leu Cys Arg
        1300            1305            1310 aca agc tgt ctt caa aaa cag tct cat tgg gta gaa ata aca gca      4082
Thr Ser Cys Leu Gln Lys Gln Ser His Trp Val Glu Ile Thr Ala
    1315            1320            1325 ctc atc cta gga gcc caa gct ctg cca gtg tac cta atg act ctt      4127
Leu Ile Leu Gly Ala Gln Ala Leu Pro Val Tyr Leu Met Thr Leu
1330            1335            1340 atg aaa gga gcc tca aga aga tct tgg cct ctt aac gag ggc ata      4172
Met Lys Gly Ala Ser Arg Arg Ser Trp Pro Leu Asn Glu Gly Ile
        1345            1350            1355 atg gct gtg ggt ttg gtt agt ctc tta gga agc gct ctt tta aag      4217
Met Ala Val Gly Leu Val Ser Leu Leu Gly Ser Ala Leu Leu Lys
    1360            1365            1370 aat gat gtc cct tta gct ggc cca atg gtg gca gga ggc tta ctt      4262
Asn Asp Val Pro Leu Ala Gly Pro Met Val Ala Gly Gly Leu Leu
1375            1380            1385 ctg gcg gct tac gtg atg agt ggt agc tca gca gat ctg tca cta      4307
Leu Ala Ala Tyr Val Met Ser Gly Ser Ser Ala Asp Leu Ser Leu
        1390            1395            1400 gag aag gcc gcc aac gtg cag tgg gat gaa atg gca gac ata aca      4352
Glu Lys Ala Ala Asn Val Gln Trp Asp Glu Met Ala Asp Ile Thr
    1405            1410            1415 ggc tca agc cca atc ata gaa gtg aag cag gat gaa gat ggc tct      4397
Gly Ser Ser Pro Ile Ile Glu Val Lys Gln Asp Glu Asp Gly Ser
1420            1425            1430 ttc tcc ata cgg gac gtc gag gaa acc aat atg ata acc ctt ttg      4442
Phe Ser Ile Arg Asp Val Glu Glu Thr Asn Met Ile Thr Leu Leu
        1435            1440            1445 gtg aaa ctg gca ctg ata aca gtg tca ggt ctc tac ccc ttg gca      4487
Val Lys Leu Ala Leu Ile Thr Val Ser Gly Leu Tyr Pro Leu Ala
    1450            1455            1460 att cca gtc aca atg acc tta tgg tac atg tgg caa gtg aaa aca      4532
Ile Pro Val Thr Met Thr Leu Trp Tyr Met Trp Gln Val Lys Thr
1465            1470            1475 caa aga tca gga gcc ctg tgg gac gtc ccc tca ccc gct gcc act      4577
Gln Arg Ser Gly Ala Leu Trp Asp Val Pro Ser Pro Ala Ala Thr -continued

```
             1480                1485                1490
aaa aaa gcc gca ctg tct gaa gga gtg tac agg atc atg caa aga      4622
Lys Lys Ala Ala Leu Ser Glu Gly Val Tyr Arg Ile Met Gln Arg
            1495                1500                1505 ggg tta ttc ggg aaa act cag gtt gga gta gga ata cac atg gaa      4667
Gly Leu Phe Gly Lys Thr Gln Val Gly Val Gly Ile His Met Glu
            1510                1515                1520 ggt gta ttt cac aca atg tgg cat gta aca aga gga tca gtg atc      4712
Gly Val Phe His Thr Met Trp His Val Thr Arg Gly Ser Val Ile
            1525                1530                1535 tgc cac gag act ggg aga ttg gag cca tct tgg gct gac gtc agg      4757
Cys His Glu Thr Gly Arg Leu Glu Pro Ser Trp Ala Asp Val Arg
            1540                1545                1550 aat gac atg ata tca tac ggt ggg gga tgg agg ctt gga gac aaa      4802
Asn Asp Met Ile Ser Tyr Gly Gly Gly Trp Arg Leu Gly Asp Lys
            1555                1560                1565 tgg gac aaa gaa gaa gac gtt cag gtc ctc gcc ata gaa cca gga      4847
Trp Asp Lys Glu Glu Asp Val Gln Val Leu Ala Ile Glu Pro Gly
            1570                1575                1580 aaa aat cct aaa cat gtc caa acg aaa cct ggc ctt ttc aag acc      4892
Lys Asn Pro Lys His Val Gln Thr Lys Pro Gly Leu Phe Lys Thr
            1585                1590                1595 cta act gga gaa att gga gca gta aca tta gat ttc aaa ccc gga      4937
Leu Thr Gly Glu Ile Gly Ala Val Thr Leu Asp Phe Lys Pro Gly
            1600                1605                1610 acg tct ggt tct ccc atc atc aac agg aaa gga aaa gtc atc gga      4982
Thr Ser Gly Ser Pro Ile Ile Asn Arg Lys Gly Lys Val Ile Gly
            1615                1620                1625 ctc tat gga aat gga gta gtt acc aaa tca ggt gat tac gtc agt      5027
Leu Tyr Gly Asn Gly Val Val Thr Lys Ser Gly Asp Tyr Val Ser
            1630                1635                1640 gcc ata acg caa gcc gaa aga att gga gag cca gat tat gaa gtg      5072
Ala Ile Thr Gln Ala Glu Arg Ile Gly Glu Pro Asp Tyr Glu Val
            1645                1650                1655 gat gag gac att ttt cga aag aaa aga tta act ata atg gac tta      5117
Asp Glu Asp Ile Phe Arg Lys Lys Arg Leu Thr Ile Met Asp Leu
            1660                1665                1670 cac ccc gga gct gga aag aca aaa aga att ctt cca tca ata gtg      5162
His Pro Gly Ala Gly Lys Thr Lys Arg Ile Leu Pro Ser Ile Val
            1675                1680                1685 aga gaa gcc tta aaa agg agg cta cga act ttg att tta gct ccc      5207
Arg Glu Ala Leu Lys Arg Arg Leu Arg Thr Leu Ile Leu Ala Pro
            1690                1695                1700 acg aga gtg gtg gcg gcc gag atg gaa gag gcc cta cgt gga ctg      5252
Thr Arg Val Val Ala Ala Glu Met Glu Glu Ala Leu Arg Gly Leu
            1705                1710                1715 cca atc cgt tat cag acc cca gct gtg aaa tca gaa cac aca gga      5297
Pro Ile Arg Tyr Gln Thr Pro Ala Val Lys Ser Glu His Thr Gly
            1720                1725                1730 aga gag att gta gac ctc atg tgt cat gca acc ttc aca aca aga      5342
Arg Glu Ile Val Asp Leu Met Cys His Ala Thr Phe Thr Thr Arg
            1735                1740                1745 ctt ttg tca tca acc agg gtt cca aat tac aac ctt ata gtg atg      5387
Leu Leu Ser Ser Thr Arg Val Pro Asn Tyr Asn Leu Ile Val Met
            1750                1755                1760 gat gaa gca cat ttc acc gat cct tct agt gtc gcg gct aga gga      5432
Asp Glu Ala His Phe Thr Asp Pro Ser Ser Val Ala Ala Arg Gly
            1765                1770                1775 tac atc tcg acc agg gtg gaa atg gga gag gca gca gcc atc ttc      5477
```

```
Tyr Ile Ser Thr Arg Val Glu Met Gly Glu Ala Ala Ala Ile Phe
            1780                1785                1790 atg acc gca acc cct ccc gga gcg aca gat ccc ttt ccc cag agc       5522
Met Thr Ala Thr Pro Pro Gly Ala Thr Asp Pro Phe Pro Gln Ser
        1795                1800                1805 aac agc cca ata gaa gac atc gag agg gaa att ccg gaa agg tca       5567
Asn Ser Pro Ile Glu Asp Ile Glu Arg Glu Ile Pro Glu Arg Ser
        1810                1815                1820 tgg aac aca ggg ttc gac tgg ata aca gac tac caa ggg aaa act       5612
Trp Asn Thr Gly Phe Asp Trp Ile Thr Asp Tyr Gln Gly Lys Thr
        1825                1830                1835 gtg tgg ttt gtt ccc agc ata aaa gct gga aat gac att gca aat       5657
Val Trp Phe Val Pro Ser Ile Lys Ala Gly Asn Asp Ile Ala Asn
        1840                1845                1850 tgt ttg aga aag tcg gga aag aaa gtt atc cag ttg agt agg aaa       5702
Cys Leu Arg Lys Ser Gly Lys Lys Val Ile Gln Leu Ser Arg Lys
        1855                1860                1865 acc ttt gat aca gag tat cca aaa acg aaa ctc acg gac tgg gac       5747
Thr Phe Asp Thr Glu Tyr Pro Lys Thr Lys Leu Thr Asp Trp Asp
        1870                1875                1880 ttt gtg gtc act aca gac ata tct gaa atg ggg gcc aat ttt aga       5792
Phe Val Val Thr Thr Asp Ile Ser Glu Met Gly Ala Asn Phe Arg
        1885                1890                1895 gcc ggg aga gtg ata gac cct aga aga tgc ctc aag cca gtt atc       5837
Ala Gly Arg Val Ile Asp Pro Arg Arg Cys Leu Lys Pro Val Ile
        1900                1905                1910 cta cca gat ggg cca gag aga gtc att tta gca ggt cct att cca       5882
Leu Pro Asp Gly Pro Glu Arg Val Ile Leu Ala Gly Pro Ile Pro
        1915                1920                1925 gtg act cca gca agc gct gct cag aga aga ggg cga ata gga agg       5927
Val Thr Pro Ala Ser Ala Ala Gln Arg Arg Gly Arg Ile Gly Arg
        1930                1935                1940 aac cca gca caa gaa gac gac caa tac gtt ttc tcc gga gac cca       5972
Asn Pro Ala Gln Glu Asp Asp Gln Tyr Val Phe Ser Gly Asp Pro
        1945                1950                1955 cta aaa aat gat gaa gat cat gcc cac tgg aca gaa gca aag atg       6017
Leu Lys Asn Asp Glu Asp His Ala His Trp Thr Glu Ala Lys Met
        1960                1965                1970 ctg ctt gac aat atc tac acc cca gaa ggg atc att cca aca ttg       6062
Leu Leu Asp Asn Ile Tyr Thr Pro Glu Gly Ile Ile Pro Thr Leu
        1975                1980                1985 ttt ggt ccg gaa agg gaa aaa acc caa gcc att gat gga gag ttt       6107
Phe Gly Pro Glu Arg Glu Lys Thr Gln Ala Ile Asp Gly Glu Phe
        1990                1995                2000 cgc ctc aga ggg gaa caa agg aag act ttt gtg gaa tta atg agg       6152
Arg Leu Arg Gly Glu Gln Arg Lys Thr Phe Val Glu Leu Met Arg
        2005                2010                2015 aga gga gac ctt ccg gtg tgg ctg agc tat aag gta gct tct gct       6197
Arg Gly Asp Leu Pro Val Trp Leu Ser Tyr Lys Val Ala Ser Ala
        2020                2025                2030 ggc att tct tac aaa gat cgg gaa tgg tgc ttc aca ggg gaa aga       6242
Gly Ile Ser Tyr Lys Asp Arg Glu Trp Cys Phe Thr Gly Glu Arg
        2035                2040                2045 aat aac caa att tta gaa gaa aac atg gag gtt gaa att tgg act       6287
Asn Asn Gln Ile Leu Glu Glu Asn Met Glu Val Glu Ile Trp Thr
        2050                2055                2060 aga gag gga gaa aag aaa aag cta agg cca aga tgg tta gat gca       6332
Arg Glu Gly Glu Lys Lys Lys Leu Arg Pro Arg Trp Leu Asp Ala
        2065                2070                2075
```

| | | | | | | | | | | | | |
|---|---|---|---|---|---|---|---|---|---|---|---|---|
| cgt | gta | tac | gct | gac | ccc | atg | gct | ttg | aag | gat | ttc | aag | gag | ttt | 6377 |
| Arg | Val | Tyr | Ala | Asp | Pro | Met | Ala | Leu | Lys | Asp | Phe | Lys | Glu | Phe | |
| | 2080 | | | | 2085 | | | | 2090 | | | | | | |

| gcc | agt | gga | agg | aag | agt | ata | act | ctc | gac | atc | cta | aca | gag | att | 6422 |
| Ala | Ser | Gly | Arg | Lys | Ser | Ile | Thr | Leu | Asp | Ile | Leu | Thr | Glu | Ile | |
| | 2095 | | | | 2100 | | | | 2105 | | | | | | |

| gcc | agt | ttg | cca | act | tac | ctt | tcc | tct | agg | gcc | aag | ctc | gcc | ctt | 6467 |
| Ala | Ser | Leu | Pro | Thr | Tyr | Leu | Ser | Ser | Arg | Ala | Lys | Leu | Ala | Leu | |
| | 2110 | | | | 2115 | | | | 2120 | | | | | | |

| gat | aac | ata | gtc | atg | ctc | cac | aca | aca | gaa | aga | gga | ggg | agg | gcc | 6512 |
| Asp | Asn | Ile | Val | Met | Leu | His | Thr | Thr | Glu | Arg | Gly | Gly | Arg | Ala | |
| | 2125 | | | | 2130 | | | | 2135 | | | | | | |

| tat | caa | cac | gcc | ctg | aac | gaa | ctt | ccg | gag | tca | ctg | gaa | aca | ctc | 6557 |
| Tyr | Gln | His | Ala | Leu | Asn | Glu | Leu | Pro | Glu | Ser | Leu | Glu | Thr | Leu | |
| | 2140 | | | | 2145 | | | | 2150 | | | | | | |

| atg | ctt | gta | gct | tta | cta | ggt | gct | atg | aca | gca | ggc | atc | ttc | ctg | 6602 |
| Met | Leu | Val | Ala | Leu | Leu | Gly | Ala | Met | Thr | Ala | Gly | Ile | Phe | Leu | |
| | 2155 | | | | 2160 | | | | 2165 | | | | | | |

| ttt | ttc | atg | caa | ggg | aaa | gga | ata | ggg | aaa | ttg | tca | atg | ggt | ttg | 6647 |
| Phe | Phe | Met | Gln | Gly | Lys | Gly | Ile | Gly | Lys | Leu | Ser | Met | Gly | Leu | |
| | 2170 | | | | 2175 | | | | 2180 | | | | | | |

| ata | acc | att | gcg | gtg | gct | agt | ggc | ttg | ctc | tgg | gta | gca | gaa | att | 6692 |
| Ile | Thr | Ile | Ala | Val | Ala | Ser | Gly | Leu | Leu | Trp | Val | Ala | Glu | Ile | |
| | 2185 | | | | 2190 | | | | 2195 | | | | | | |

| caa | ccc | cag | tgg | ata | gcg | gcc | tca | atc | ata | cta | gag | ttt | ttt | ctc | 6737 |
| Gln | Pro | Gln | Trp | Ile | Ala | Ala | Ser | Ile | Ile | Leu | Glu | Phe | Phe | Leu | |
| | 2200 | | | | 2205 | | | | 2210 | | | | | | |

| atg | gta | ctg | ttg | ata | ccg | gaa | cca | gaa | aaa | caa | agg | acc | cca | caa | 6782 |
| Met | Val | Leu | Leu | Ile | Pro | Glu | Pro | Glu | Lys | Gln | Arg | Thr | Pro | Gln | |
| | 2215 | | | | 2220 | | | | 2225 | | | | | | |

| gac | aat | caa | ttg | atc | tac | gtc | ata | ttg | acc | att | ctc | acc | atc | att | 6827 |
| Asp | Asn | Gln | Leu | Ile | Tyr | Val | Ile | Leu | Thr | Ile | Leu | Thr | Ile | Ile | |
| | 2230 | | | | 2235 | | | | 2240 | | | | | | |

| ggt | cta | ata | gca | gcc | aac | gag | atg | ggg | ctg | att | gaa | aaa | aca | aaa | 6872 |
| Gly | Leu | Ile | Ala | Ala | Asn | Glu | Met | Gly | Leu | Ile | Glu | Lys | Thr | Lys | |
| | 2245 | | | | 2250 | | | | 2255 | | | | | | |

| acg | gat | ttt | ggg | ttt | tac | cag | gta | aaa | aca | gaa | acc | acc | atc | ctc | 6917 |
| Thr | Asp | Phe | Gly | Phe | Tyr | Gln | Val | Lys | Thr | Glu | Thr | Thr | Ile | Leu | |
| | 2260 | | | | 2265 | | | | 2270 | | | | | | |

| gat | gtg | gac | ttg | aga | cca | gct | tca | gca | tgg | acg | ctc | tat | gca | gta | 6962 |
| Asp | Val | Asp | Leu | Arg | Pro | Ala | Ser | Ala | Trp | Thr | Leu | Tyr | Ala | Val | |
| | 2275 | | | | 2280 | | | | 2285 | | | | | | |

| gcc | acc | aca | att | ctg | act | ccc | atg | ctg | aga | cac | acc | ata | gaa | aac | 7007 |
| Ala | Thr | Thr | Ile | Leu | Thr | Pro | Met | Leu | Arg | His | Thr | Ile | Glu | Asn | |
| | 2290 | | | | 2295 | | | | 2300 | | | | | | |

| acg | tcg | gcc | aac | cta | tct | cta | gca | gcc | att | gcc | aac | cag | gca | gcc | 7052 |
| Thr | Ser | Ala | Asn | Leu | Ser | Leu | Ala | Ala | Ile | Ala | Asn | Gln | Ala | Ala | |
| | 2305 | | | | 2310 | | | | 2315 | | | | | | |

| gtc | cta | atg | ggg | ctt | gga | aaa | gga | tgg | ccg | ctc | cac | aga | atg | gac | 7097 |
| Val | Leu | Met | Gly | Leu | Gly | Lys | Gly | Trp | Pro | Leu | His | Arg | Met | Asp | |
| | 2320 | | | | 2325 | | | | 2330 | | | | | | |

| ctc | ggt | gtg | ccg | ctg | tta | gca | atg | gga | tgc | tat | tct | caa | gtg | aac | 7142 |
| Leu | Gly | Val | Pro | Leu | Leu | Ala | Met | Gly | Cys | Tyr | Ser | Gln | Val | Asn | |
| | 2335 | | | | 2340 | | | | 2345 | | | | | | |

| cca | aca | acc | ttg | aca | gca | tcc | tta | gtc | atg | ctt | ttc | gtg | cac | tat | 7187 |
| Pro | Thr | Thr | Leu | Thr | Ala | Ser | Leu | Val | Met | Leu | Phe | Val | His | Tyr | |
| | 2350 | | | | 2355 | | | | 2360 | | | | | | |

| gca | ata | ata | ggc | cca | gga | ttg | cag | gca | aaa | gcc | aca | aga | gag | gcc | 7232 |
| Ala | Ile | Ile | Gly | Pro | Gly | Leu | Gln | Ala | Lys | Ala | Thr | Arg | Glu | Ala | |
| | 2365 | | | | 2370 | | | | 2375 | | | | | | |

| | | | | | | | | | | | |
|---|---|---|---|---|---|---|---|---|---|---|---|
| cag | aaa | agg | aca | gct | gct | ggg | atc | atg | aaa | aat | ccc | aca | gtg | gac | 7277 |
| Gln | Lys | Arg | Thr | Ala | Ala | Gly | Ile | Met | Lys | Asn | Pro | Thr | Val | Asp | |
| | | 2380 | | | | 2385 | | | | 2390 | | | | | |
| ggg | ata | aca | gta | ata | gat | cta | gaa | cca | ata | tcc | tat | gac | cca | aaa | 7322 |
| Gly | Ile | Thr | Val | Ile | Asp | Leu | Glu | Pro | Ile | Ser | Tyr | Asp | Pro | Lys | |
| | | 2395 | | | | 2400 | | | | 2405 | | | | | |
| ttt | gaa | aag | caa | tta | ggg | cag | gtc | atg | cta | cta | gtc | ttg | tgt | gct | 7367 |
| Phe | Glu | Lys | Gln | Leu | Gly | Gln | Val | Met | Leu | Leu | Val | Leu | Cys | Ala | |
| | | 2410 | | | | 2415 | | | | 2420 | | | | | |
| gga | caa | cta | ctc | ttg | atg | aga | aca | aca | tgg | gct | ttc | tgt | gaa | gtc | 7412 |
| Gly | Gln | Leu | Leu | Leu | Met | Arg | Thr | Thr | Trp | Ala | Phe | Cys | Glu | Val | |
| | | 2425 | | | | 2430 | | | | 2435 | | | | | |
| ttg | act | ttg | gcc | aca | gga | cca | atc | ttg | acc | ttg | tgg | gag | ggc | aac | 7457 |
| Leu | Thr | Leu | Ala | Thr | Gly | Pro | Ile | Leu | Thr | Leu | Trp | Glu | Gly | Asn | |
| | | 2440 | | | | 2445 | | | | 2450 | | | | | |
| ccg | gga | agg | ttt | tgg | aac | acg | acc | ata | gcc | gta | tcc | acc | gcc | aac | 7502 |
| Pro | Gly | Arg | Phe | Trp | Asn | Thr | Thr | Ile | Ala | Val | Ser | Thr | Ala | Asn | |
| | | 2455 | | | | 2460 | | | | 2465 | | | | | |
| att | ttc | agg | gga | agt | tac | ttg | gcg | gga | gct | gga | ctg | gct | ttt | tca | 7547 |
| Ile | Phe | Arg | Gly | Ser | Tyr | Leu | Ala | Gly | Ala | Gly | Leu | Ala | Phe | Ser | |
| | | 2470 | | | | 2475 | | | | 2480 | | | | | |
| ctc | ata | aag | aat | gca | caa | acc | cct | agg | agg | gga | act | ggg | acc | aca | 7592 |
| Leu | Ile | Lys | Asn | Ala | Gln | Thr | Pro | Arg | Arg | Gly | Thr | Gly | Thr | Thr | |
| | | 2485 | | | | 2490 | | | | 2495 | | | | | |
| gga | gag | aca | ctg | gga | gag | aag | tgg | aag | aga | cag | cta | aac | tca | tta | 7637 |
| Gly | Glu | Thr | Leu | Gly | Glu | Lys | Trp | Lys | Arg | Gln | Leu | Asn | Ser | Leu | |
| | | 2500 | | | | 2505 | | | | 2510 | | | | | |
| gac | aga | aaa | gag | ttt | gaa | gag | tat | aaa | aga | agt | gga | ata | cta | gaa | 7682 |
| Asp | Arg | Lys | Glu | Phe | Glu | Glu | Tyr | Lys | Arg | Ser | Gly | Ile | Leu | Glu | |
| | | 2515 | | | | 2520 | | | | 2525 | | | | | |
| gtg | gac | agg | act | gaa | gcc | aag | tct | gcc | ctg | aaa | gat | ggg | tct | aaa | 7727 |
| Val | Asp | Arg | Thr | Glu | Ala | Lys | Ser | Ala | Leu | Lys | Asp | Gly | Ser | Lys | |
| | | 2530 | | | | 2535 | | | | 2540 | | | | | |
| atc | aag | cat | gca | gta | tca | aga | ggg | tcc | agt | aag | atc | aga | tgg | att | 7772 |
| Ile | Lys | His | Ala | Val | Ser | Arg | Gly | Ser | Ser | Lys | Ile | Arg | Trp | Ile | |
| | | 2545 | | | | 2550 | | | | 2555 | | | | | |
| gtt | gag | aga | ggg | atg | gta | aag | cca | aaa | ggg | aaa | gtt | gta | gat | ctt | 7817 |
| Val | Glu | Arg | Gly | Met | Val | Lys | Pro | Lys | Gly | Lys | Val | Val | Asp | Leu | |
| | | 2560 | | | | 2565 | | | | 2570 | | | | | |
| ggc | tgt | ggg | aga | gga | gga | tgg | tct | tat | tac | atg | gcg | aca | ctc | aag | 7862 |
| Gly | Cys | Gly | Arg | Gly | Gly | Trp | Ser | Tyr | Tyr | Met | Ala | Thr | Leu | Lys | |
| | | 2575 | | | | 2580 | | | | 2585 | | | | | |
| aac | gtg | act | gaa | gtg | aaa | ggg | tat | aca | aaa | gga | ggt | cca | gga | cat | 7907 |
| Asn | Val | Thr | Glu | Val | Lys | Gly | Tyr | Thr | Lys | Gly | Gly | Pro | Gly | His | |
| | | 2590 | | | | 2595 | | | | 2600 | | | | | |
| gaa | gaa | ccg | att | ccc | atg | gct | act | tat | ggt | tgg | aat | ttg | gtc | aaa | 7952 |
| Glu | Glu | Pro | Ile | Pro | Met | Ala | Thr | Tyr | Gly | Trp | Asn | Leu | Val | Lys | |
| | | 2605 | | | | 2610 | | | | 2615 | | | | | |
| ctc | cat | tca | ggg | gtt | gac | gtg | ttc | tac | aaa | ccc | aca | gag | caa | gtg | 7997 |
| Leu | His | Ser | Gly | Val | Asp | Val | Phe | Tyr | Lys | Pro | Thr | Glu | Gln | Val | |
| | | 2620 | | | | 2625 | | | | 2630 | | | | | |
| gac | acc | ctg | ctc | tgt | gat | att | ggg | gag | tca | tct | tct | aat | cca | aca | 8042 |
| Asp | Thr | Leu | Leu | Cys | Asp | Ile | Gly | Glu | Ser | Ser | Ser | Asn | Pro | Thr | |
| | | 2635 | | | | 2640 | | | | 2645 | | | | | |
| ata | gag | gaa | gga | aga | aca | tta | aga | gtt | ttg | aag | atg | gtg | gag | cca | 8087 |
| Ile | Glu | Glu | Gly | Arg | Thr | Leu | Arg | Val | Leu | Lys | Met | Val | Glu | Pro | |
| | | 2650 | | | | 2655 | | | | 2660 | | | | | |
| tgg | ctc | tct | tca | aaa | cct | gaa | ttc | tgc | atc | aaa | gtc | ctt | aac | ccc | 8132 |
| Trp | Leu | Ser | Ser | Lys | Pro | Glu | Phe | Cys | Ile | Lys | Val | Leu | Asn | Pro | |

```
                  2665                2670                2675
tac atg cca aca gtc ata gaa gag ctg gag aaa ctg cag aga aaa        8177
Tyr Met Pro Thr Val Ile Glu Glu Leu Glu Lys Leu Gln Arg Lys
            2680                2685                2690 cat ggt ggg aac ctt gtc aga tgc ccg ctg tcc agg aac tcc acc        8222
His Gly Gly Asn Leu Val Arg Cys Pro Leu Ser Arg Asn Ser Thr
            2695                2700                2705 cat gag atg tat tgg gtg tca gga gcg tcg gga aac att gtg agc        8267
His Glu Met Tyr Trp Val Ser Gly Ala Ser Gly Asn Ile Val Ser
            2710                2715                2720 tct gtg aac aca aca tca aag atg ttg ttg aac agg ttc aca aca        8312
Ser Val Asn Thr Thr Ser Lys Met Leu Leu Asn Arg Phe Thr Thr
            2725                2730                2735 agg cat agg aaa ccc act tat gag aag gac gta gat ctt ggg gca        8357
Arg His Arg Lys Pro Thr Tyr Glu Lys Asp Val Asp Leu Gly Ala
            2740                2745                2750 gga acg aga agt gtc tcc act gaa aca gaa aaa cca gac atg aca        8402
Gly Thr Arg Ser Val Ser Thr Glu Thr Glu Lys Pro Asp Met Thr
            2755                2760                2765 atc att ggg aga agg ctt cag cga ttg caa gaa gag cac aaa gaa        8447
Ile Ile Gly Arg Arg Leu Gln Arg Leu Gln Glu Glu His Lys Glu
            2770                2775                2780 acc tgg cat tat gat cag gaa aac cca tac aga acc tgg gcg tat        8492
Thr Trp His Tyr Asp Gln Glu Asn Pro Tyr Arg Thr Trp Ala Tyr
            2785                2790                2795 cat gga agc tat gaa gct cct tcg aca ggc tct gca tcc tcc atg        8537
His Gly Ser Tyr Glu Ala Pro Ser Thr Gly Ser Ala Ser Ser Met
            2800                2805                2810 gtg aac ggg gtg gta aaa ctg cta aca aaa ccc tgg gat gtg att        8582
Val Asn Gly Val Val Lys Leu Leu Thr Lys Pro Trp Asp Val Ile
            2815                2820                2825 cca atg gtg act cag tta gcc atg aca gat aca acc cct ttt ggg        8627
Pro Met Val Thr Gln Leu Ala Met Thr Asp Thr Thr Pro Phe Gly
            2830                2835                2840 caa caa aga gtg ttc aaa gag aag gtg gat acc aga aca cca caa        8672
Gln Gln Arg Val Phe Lys Glu Lys Val Asp Thr Arg Thr Pro Gln
            2845                2850                2855 cca aaa ccc ggt aca cga atg gtt atg acc acg aca gcc aat tgg        8717
Pro Lys Pro Gly Thr Arg Met Val Met Thr Thr Thr Ala Asn Trp
            2860                2865                2870 ctg tgg gcc ctc ctt gga aag aag aaa aat ccc aga ctg tgc aca        8762
Leu Trp Ala Leu Leu Gly Lys Lys Lys Asn Pro Arg Leu Cys Thr
            2875                2880                2885 agg gaa gag ttc atc tca aaa gtt aga tca aac gca gcc ata ggc        8807
Arg Glu Glu Phe Ile Ser Lys Val Arg Ser Asn Ala Ala Ile Gly
            2890                2895                2900 gca gtc ttt cag gaa gaa cag gga tgg aca tca gcc agt gaa gct        8852
Ala Val Phe Gln Glu Glu Gln Gly Trp Thr Ser Ala Ser Glu Ala
            2905                2910                2915 gtg aat gac agc cgg ttt tgg gaa ctg gtt gac aaa gaa agg gcc        8897
Val Asn Asp Ser Arg Phe Trp Glu Leu Val Asp Lys Glu Arg Ala
            2920                2925                2930 cta cac cag gaa ggg aaa tgt gaa tcg tgt gtc tat aac atg atg        8942
Leu His Gln Glu Gly Lys Cys Glu Ser Cys Val Tyr Asn Met Met
            2935                2940                2945 gga aaa cgt gag aaa aag tta gga gag ttt ggc aga gcc aag gga        8987
Gly Lys Arg Glu Lys Lys Leu Gly Glu Phe Gly Arg Ala Lys Gly
            2950                2955                2960 agc cga gca atc tgg tac atg tgg ctg gga gcg cgg ttt ctg gaa        9032
```

-continued

| | | | | | | | | | | | | | |
|---|---|---|---|---|---|---|---|---|---|---|---|---|---|
| Ser | Arg | Ala | Ile | Trp | Tyr | Met | Trp | Leu | Gly | Ala | Arg | Phe | Leu | Glu |
| | | 2965 | | | | 2970 | | | | 2975 | | | | |

| ttt | gaa | gcc | ctg | ggt | ttt | ttg | aat | gaa | gat | cac | tgg | ttt | ggc | aga | 9077 |
|---|---|---|---|---|---|---|---|---|---|---|---|---|---|---|---|
| Phe | Glu | Ala | Leu | Gly | Phe | Leu | Asn | Glu | Asp | His | Trp | Phe | Gly | Arg | |
| | | 2980 | | | | 2985 | | | | 2990 | | | | | |

| gaa | aat | tca | tgg | agt | gga | gtg | gaa | ggg | gaa | ggt | ctg | cac | aga | ttg | 9122 |
|---|---|---|---|---|---|---|---|---|---|---|---|---|---|---|---|
| Glu | Asn | Ser | Trp | Ser | Gly | Val | Glu | Gly | Glu | Gly | Leu | His | Arg | Leu | |
| | | 2995 | | | | 3000 | | | | 3005 | | | | | |

| gga | tat | atc | ctg | gag | gag | ata | gac | aag | aag | gat | gga | gac | cta | atg | 9167 |
|---|---|---|---|---|---|---|---|---|---|---|---|---|---|---|---|
| Gly | Tyr | Ile | Leu | Glu | Glu | Ile | Asp | Lys | Lys | Asp | Gly | Asp | Leu | Met | |
| | | 3010 | | | | 3015 | | | | 3020 | | | | | |

| tat | gct | gat | gac | aca | gca | ggc | tgg | gac | aca | aga | atc | act | gag | gat | 9212 |
|---|---|---|---|---|---|---|---|---|---|---|---|---|---|---|---|
| Tyr | Ala | Asp | Asp | Thr | Ala | Gly | Trp | Asp | Thr | Arg | Ile | Thr | Glu | Asp | |
| | | 3025 | | | | 3030 | | | | 3035 | | | | | |

| gac | ctt | caa | aat | gag | gaa | ctg | atc | acg | gaa | cag | atg | gct | ccc | cac | 9257 |
|---|---|---|---|---|---|---|---|---|---|---|---|---|---|---|---|
| Asp | Leu | Gln | Asn | Glu | Glu | Leu | Ile | Thr | Glu | Gln | Met | Ala | Pro | His | |
| | | 3040 | | | | 3045 | | | | 3050 | | | | | |

| cac | aag | atc | cta | gcc | aaa | gcc | att | ttc | aaa | cta | acc | tat | caa | aac | 9302 |
|---|---|---|---|---|---|---|---|---|---|---|---|---|---|---|---|
| His | Lys | Ile | Leu | Ala | Lys | Ala | Ile | Phe | Lys | Leu | Thr | Tyr | Gln | Asn | |
| | | 3055 | | | | 3060 | | | | 3065 | | | | | |

| aaa | gtg | gtg | aaa | gtc | ctc | aga | ccc | aca | ccg | cgg | gga | gcg | gtg | atg | 9347 |
|---|---|---|---|---|---|---|---|---|---|---|---|---|---|---|---|
| Lys | Val | Val | Lys | Val | Leu | Arg | Pro | Thr | Pro | Arg | Gly | Ala | Val | Met | |
| | | 3070 | | | | 3075 | | | | 3080 | | | | | |

| gat | atc | ata | tcc | agg | aaa | gac | caa | aga | ggt | agt | gga | caa | gtt | gga | 9392 |
|---|---|---|---|---|---|---|---|---|---|---|---|---|---|---|---|
| Asp | Ile | Ile | Ser | Arg | Lys | Asp | Gln | Arg | Gly | Ser | Gly | Gln | Val | Gly | |
| | | 3085 | | | | 3090 | | | | 3095 | | | | | |

| aca | tat | ggt | ttg | aac | aca | ttc | acc | aac | atg | gaa | gtt | caa | ctc | atc | 9437 |
|---|---|---|---|---|---|---|---|---|---|---|---|---|---|---|---|
| Thr | Tyr | Gly | Leu | Asn | Thr | Phe | Thr | Asn | Met | Glu | Val | Gln | Leu | Ile | |
| | | 3100 | | | | 3105 | | | | 3110 | | | | | |

| cgc | caa | atg | gaa | gct | gaa | gga | gtc | atc | aca | caa | gat | gac | atg | cag | 9482 |
|---|---|---|---|---|---|---|---|---|---|---|---|---|---|---|---|
| Arg | Gln | Met | Glu | Ala | Glu | Gly | Val | Ile | Thr | Gln | Asp | Asp | Met | Gln | |
| | | 3115 | | | | 3120 | | | | 3125 | | | | | |

| aac | cca | aaa | ggg | ttg | aaa | gaa | aga | gtt | gag | aaa | tgg | ctg | aaa | gag | 9527 |
|---|---|---|---|---|---|---|---|---|---|---|---|---|---|---|---|
| Asn | Pro | Lys | Gly | Leu | Lys | Glu | Arg | Val | Glu | Lys | Trp | Leu | Lys | Glu | |
| | | 3130 | | | | 3135 | | | | 3140 | | | | | |

| tgt | ggt | gtc | gca | gcg | tta | aag | agg | atg | gca | atc | agt | gga | gac | gat | 9572 |
|---|---|---|---|---|---|---|---|---|---|---|---|---|---|---|---|
| Cys | Gly | Val | Ala | Ala | Leu | Lys | Arg | Met | Ala | Ile | Ser | Gly | Asp | Asp | |
| | | 3145 | | | | 3150 | | | | 3155 | | | | | |

| tgc | gtg | gtg | aag | ccc | cta | gat | gag | agg | ttt | ggc | act | tcc | ctc | ctc | 9617 |
|---|---|---|---|---|---|---|---|---|---|---|---|---|---|---|---|
| Cys | Val | Val | Lys | Pro | Leu | Asp | Glu | Arg | Phe | Gly | Thr | Ser | Leu | Leu | |
| | | 3160 | | | | 3165 | | | | 3170 | | | | | |

| ttc | ttg | aac | gac | atg | gga | aag | gtg | agg | aaa | gac | att | ccg | cag | tgg | 9662 |
|---|---|---|---|---|---|---|---|---|---|---|---|---|---|---|---|
| Phe | Leu | Asn | Asp | Met | Gly | Lys | Val | Arg | Lys | Asp | Ile | Pro | Gln | Trp | |
| | | 3175 | | | | 3180 | | | | 3185 | | | | | |

| gaa | cca | tct | aag | gga | tgg | aaa | aac | tgg | caa | gag | gtt | cct | ttt | tgc | 9707 |
|---|---|---|---|---|---|---|---|---|---|---|---|---|---|---|---|
| Glu | Pro | Ser | Lys | Gly | Trp | Lys | Asn | Trp | Gln | Glu | Val | Pro | Phe | Cys | |
| | | 3190 | | | | 3195 | | | | 3200 | | | | | |

| tcc | cac | cac | ttt | cac | aag | atc | ttt | atg | aag | gat | ggc | cgc | tca | cta | 9752 |
|---|---|---|---|---|---|---|---|---|---|---|---|---|---|---|---|
| Ser | His | His | Phe | His | Lys | Ile | Phe | Met | Lys | Asp | Gly | Arg | Ser | Leu | |
| | | 3205 | | | | 3210 | | | | 3215 | | | | | |

| gtt | gtt | cca | tgt | aga | aac | cag | gat | gaa | ctg | ata | ggg | aga | gcc | aga | 9797 |
|---|---|---|---|---|---|---|---|---|---|---|---|---|---|---|---|
| Val | Val | Pro | Cys | Arg | Asn | Gln | Asp | Glu | Leu | Ile | Gly | Arg | Ala | Arg | |
| | | 3220 | | | | 3225 | | | | 3230 | | | | | |

| atc | tcg | cag | gga | gct | gga | tgg | agc | tta | aga | gaa | aca | gcc | tgc | ctg | 9842 |
|---|---|---|---|---|---|---|---|---|---|---|---|---|---|---|---|
| Ile | Ser | Gln | Gly | Ala | Gly | Trp | Ser | Leu | Arg | Glu | Thr | Ala | Cys | Leu | |
| | | 3235 | | | | 3240 | | | | 3245 | | | | | |

| ggc | aaa | gct | tac | gcc | cag | atg | tgg | tcg | ctt | atg | tac | ttc | cac | aga | 9887 |
|---|---|---|---|---|---|---|---|---|---|---|---|---|---|---|---|
| Gly | Lys | Ala | Tyr | Ala | Gln | Met | Trp | Ser | Leu | Met | Tyr | Phe | His | Arg | |
| | | 3250 | | | | 3255 | | | | 3260 | | | | | |

```
agg gat ctg cgt tta gcc tcc atg gcc ata tgc tca gca gtt cca    9932
Arg Asp Leu Arg Leu Ala Ser Met Ala Ile Cys Ser Ala Val Pro
        3265            3270            3275 acg gaa tgg ttt cca aca agc aga aca aca tgg tca atc cac gct    9977
Thr Glu Trp Phe Pro Thr Ser Arg Thr Thr Trp Ser Ile His Ala
    3280            3285            3290 cat cac cag tgg atg acc act gaa gat atg ctc aaa gtg tgg aac   10022
His His Gln Trp Met Thr Thr Glu Asp Met Leu Lys Val Trp Asn
        3295            3300            3305 aga gtg tgg ata gaa gac aac cct aat atg act gac aag act cca   10067
Arg Val Trp Ile Glu Asp Asn Pro Asn Met Thr Asp Lys Thr Pro
        3310            3315            3320 gtc cat tcg tgg gaa gat ata cct tac cta ggg aaa aga gag gat   10112
Val His Ser Trp Glu Asp Ile Pro Tyr Leu Gly Lys Arg Glu Asp
        3325            3330            3335 ttg tgg tgt gga tcc ctg att gga ctt tct tcc aga gcc acc tgg   10157
Leu Trp Cys Gly Ser Leu Ile Gly Leu Ser Ser Arg Ala Thr Trp
        3340            3345            3350 gcg aag aac att cac acg gcc ata acc cag gtc agg aac ctg atc   10202
Ala Lys Asn Ile His Thr Ala Ile Thr Gln Val Arg Asn Leu Ile
        3355            3360            3365 gga aaa gag gaa tac gtg gat tac atg cca gta atg aaa aga tac   10247
Gly Lys Glu Glu Tyr Val Asp Tyr Met Pro Val Met Lys Arg Tyr
        3370            3375            3380 agt gct cct tca gag agt gaa gga gtt ctg taa ttaccaacaa         10290
Ser Ala Pro Ser Glu Ser Glu Gly Val Leu
        3385            3390 caaacaccaa aggctattga agtcaggcca cttgtgccac ggtttgagca aaccgtgctg   10350
cctgtagctc cgccaataat gggaggcgta ataatcccca gggaggccat gcgccacgga   10410
agctgtacgc gtggcatatt ggactagcgg ttagaggaga cccctcccat cactgacaaa   10470
acgcagcaaa agggggccca agactagagg ttagaggaga ccccccaac acaaaaacag   10530 catattgacg ctgggaaaga ccagagatcc tgctgtctct gcaacatcaa tccaggcaca   10590
gagcgccgca agatggattg gtgttgttga tccaacaggt tct                    10633

<210> SEQ ID NO 2
<211> LENGTH: 3392
<212> TYPE: PRT
<213> ORGANISM: Artificial Sequence
<220> FEATURE:
<223> OTHER INFORMATION: Synthetic Construct

<400> SEQUENCE: 2

Met Asn Gln Arg Lys Lys Val Val Arg Pro Pro Phe Asn Met Leu Lys
1               5                   10                  15

Arg Glu Arg Asn Arg Val Ser Thr Pro Gln Gly Leu Val Lys Arg Phe
            20                  25                  30

Ser Thr Gly Leu Phe Ser Gly Lys Gly Pro Leu Arg Met Val Leu Ala
        35                  40                  45

Phe Ile Thr Phe Leu Arg Val Leu Ser Ile Pro Pro Thr Ala Gly Ile
    50                  55                  60

Leu Lys Arg Trp Gly Gln Leu Lys Lys Asn Lys Ala Ile Lys Ile Leu
65                  70                  75                  80

Ile Gly Phe Arg Lys Glu Ile Gly Arg Met Leu Asn Ile Leu Asn Gly
                85                  90                  95

Arg Lys Arg Ser Ala Val Asp Thr Gly Trp Leu Val Val Val
            100                 105                 110
```

```
Leu Leu Gly Val Thr Leu Ala Ala Thr Val Arg Lys Glu Arg Asp Gly
            115                 120                 125

Thr Thr Val Ile Arg Ala Glu Gly Lys Asp Ala Ala Thr Gln Val Arg
        130                 135                 140

Val Glu Asn Gly Thr Cys Val Ile Leu Ala Thr Asp Met Gly Ser Trp
145                 150                 155                 160

Cys Asp Asp Ser Leu Thr Tyr Glu Cys Val Thr Ile Asp Gln Gly Glu
                165                 170                 175

Glu Pro Val Asp Val Asp Cys Phe Cys Arg Asn Val Asp Gly Val Tyr
            180                 185                 190

Leu Glu Tyr Gly Arg Cys Gly Lys Gln Glu Gly Ser Arg Thr Arg Arg
        195                 200                 205

Ser Val Leu Ile Pro Ser His Ala Gln Gly Asp Leu Thr Gly Arg Gly
210                 215                 220

His Lys Trp Leu Glu Gly Asp Ser Leu Arg Thr His Leu Thr Arg Val
225                 230                 235                 240

Glu Gly Trp Val Trp Lys Asn Lys Val Leu Thr Leu Ala Val Ile Ala
                245                 250                 255

Val Val Trp Leu Thr Val Glu Ser Val Val Thr Arg Val Ala Val Val
            260                 265                 270

Val Val Leu Leu Cys Leu Ala Pro Val Tyr Ala Ser Arg Cys Thr His
        275                 280                 285

Leu Glu Asn Arg Asp Phe Val Thr Gly Thr Gln Gly Thr Thr Arg Val
        290                 295                 300

Thr Leu Val Leu Glu Leu Gly Gly Cys Val Thr Ile Thr Ala Glu Gly
305                 310                 315                 320

Lys Pro Ser Met Asp Val Trp Leu Asp Ser Ile Tyr Gln Glu Asn Pro
                325                 330                 335

Ala Lys Thr Arg Glu Tyr Cys Leu His Ala Lys Leu Ser Asp Thr Lys
            340                 345                 350

Val Ala Ala Arg Cys Pro Thr Met Gly Pro Ala Thr Leu Ala Glu Glu
        355                 360                 365

His Gln Ser Gly Thr Val Cys Lys Arg Asp Gln Ser Asp Arg Gly Trp
370                 375                 380

Gly Asn His Cys Gly Leu Phe Gly Lys Gly Ser Ile Val Thr Cys Val
385                 390                 395                 400

Lys Ala Ser Cys Glu Ala Lys Lys Lys Ala Thr Gly His Val Tyr Asp
                405                 410                 415

Ala Asn Lys Ile Val Tyr Thr Val Lys Val Glu Pro His Thr Gly Asp
            420                 425                 430

Tyr Val Ala Ala Asn Glu Thr His Ser Gly Arg Lys Thr Ala Ser Phe
        435                 440                 445

Thr Val Ser Ser Glu Arg Thr Ile Leu Thr Met Gly Asp Tyr Gly Asp
450                 455                 460

Val Ser Leu Leu Cys Arg Val Ala Ser Gly Val Asp Leu Ala Gln Thr
465                 470                 475                 480

Val Ile Leu Glu Leu Asp Lys Thr Ser Glu His Leu Pro Thr Ala Trp
                485                 490                 495

Gln Val His Arg Asp Trp Phe Asn Asp Leu Ala Leu Pro Trp Lys His
            500                 505                 510

Glu Gly Ala Gln Asn Trp Asn Asn Ala Glu Trp Leu Val Glu Phe Gly
        515                 520                 525

Ala Pro His Ala Val Lys Met Asp Val Tyr Asn Leu Gly Asp Gln Thr
```

```
              530              535              540
Gly Val Leu Leu Lys Ser Leu Ala Gly Val Pro Val Ala His Ile Asp
545                 550                 555                 560

Gly Thr Lys Tyr His Leu Lys Ser Gly His Val Thr Cys Glu Val Gly
                    565                 570                 575

Leu Glu Lys Leu Lys Met Lys Gly Leu Thr Tyr Thr Met Cys Asp Lys
                580                 585                 590

Thr Lys Phe Thr Trp Asp Arg Ile Pro Thr Asp Ser Gly His Asp Thr
            595                 600                 605

Val Val Met Glu Val Ala Phe Ser Gly Thr Lys Pro Cys Arg Ile Pro
610                 615                 620

Val Arg Ala Val Ala His Gly Ser Pro Asp Val Asn Val Ala Met Leu
625                 630                 635                 640

Ile Thr Pro Asn Pro Thr Ile Glu Asn Asn Gly Gly Phe Ile Glu
                    645                 650                 655

Met Gln Leu Pro Pro Gly Asp Asn Ile Ile Tyr Val Gly Glu Leu Ser
                660                 665                 670

His Gln Trp Phe Gln Lys Gly Ser Ser Ile Gly Arg Val Phe Gln Lys
            675                 680                 685

Thr Arg Lys Gly Ile Glu Arg Leu Thr Val Ile Gly Glu His Ala Trp
690                 695                 700

Asp Phe Gly Ser Thr Gly Gly Phe Leu Thr Ser Val Gly Lys Ala Leu
705                 710                 715                 720

His Thr Val Leu Gly Gly Ala Phe Asn Ser Leu Phe Gly Gly Val Gly
                    725                 730                 735

Phe Leu Pro Lys Ile Leu Val Gly Val Val Leu Ala Trp Leu Gly Leu
                740                 745                 750

Asn Ser Arg Asn Thr Ser Met Ala Met Thr Cys Ile Ala Val Gly Gly
            755                 760                 765

Ile Thr Leu Phe Leu Gly Phe Thr Val Gln Ala Asp Met Gly Cys Val
770                 775                 780

Ala Ser Trp Ser Gly Lys Glu Leu Lys Cys Gly Ser Gly Ile Phe Val
785                 790                 795                 800

Val Asp Asn Val His Thr Trp Thr Glu Gln Tyr Lys Phe Gln Pro Glu
                    805                 810                 815

Ser Pro Ala Arg Leu Ala Ser Ala Ile Leu Asn Ala His Lys Asp Gly
                820                 825                 830

Val Cys Gly Ile Arg Ser Thr Thr Arg Leu Glu Asn Val Met Trp Lys
            835                 840                 845

Gln Ile Thr Asn Glu Leu Asn Tyr Val Leu Trp Glu Gly Gly His Asp
850                 855                 860

Leu Thr Val Val Ala Gly Asp Val Lys Gly Val Leu Thr Lys Gly Lys
865                 870                 875                 880

Arg Ala Leu Thr Pro Pro Val Ser Asp Leu Lys Tyr Ser Trp Lys Thr
                    885                 890                 895

Trp Gly Lys Ala Lys Ile Phe Thr Pro Glu Ala Arg Asn Ser Thr Phe
                900                 905                 910

Leu Ile Asp Gly Pro Asp Thr Ser Glu Cys Pro Asn Glu Arg Arg Ala
            915                 920                 925

Trp Asn Ser Leu Glu Val Glu Asp Tyr Gly Phe Gly Met Phe Thr Thr
930                 935                 940

Asn Ile Trp Met Lys Phe Arg Glu Gly Ser Ser Glu Val Cys Asp His
945                 950                 955                 960
```

```
Arg Leu Met Ser Ala Ala Ile Lys Asp Gln Lys Ala Val His Ala Asp
              965                 970                 975

Met Gly Tyr Trp Ile Glu Ser Ser Lys Asn Gln Thr Trp Gln Ile Glu
          980                 985                 990

Lys Ala Ser Leu Ile Glu Val Lys  Thr Cys Leu Trp Pro  Lys Thr His
          995                 1000                1005

Thr Leu Trp Ser Asn Gly Val  Leu Glu Ser Gln Met  Leu Ile Pro
    1010                1015                1020

Lys Ser Tyr Ala Gly Pro Phe  Ser Gln His Asn Tyr  Arg Gln Gly
    1025                1030                1035

Tyr Ala Thr Gln Thr Val Gly  Pro Trp His Leu Gly  Lys Leu Glu
    1040                1045                1050

Ile Asp Phe Gly Glu Cys Pro  Gly Thr Thr Val Thr  Ile Gln Glu
    1055                1060                1065

Asp Cys Asp His Arg Gly Pro  Ser Leu Arg Thr Thr  Thr Ala Ser
    1070                1075                1080

Gly Lys Leu Val Thr Gln Trp  Cys Cys Arg Ser Cys  Thr Met Pro
    1085                1090                1095

Pro Leu Arg Phe Leu Gly Glu  Asp Gly Cys Trp Tyr  Gly Met Glu
    1100                1105                1110

Ile Arg Pro Leu Ser Glu Lys  Glu Glu Asn Met Val  Lys Ser Gln
    1115                1120                1125

Val Thr Ala Gly Gln Gly Thr  Ser Glu Thr Phe Ser  Met Gly Leu
    1130                1135                1140

Leu Cys Leu Thr Leu Phe Val  Glu Glu Cys Leu Arg  Arg Arg Val
    1145                1150                1155

Thr Arg Lys His Met Ile Leu  Val Val Val Ile Thr  Leu Cys Ala
    1160                1165                1170

Ile Ile Leu Gly Gly Leu Thr  Trp Met Asp Leu Leu  Arg Ala Leu
    1175                1180                1185

Ile Met Leu Gly Asp Thr Met  Ser Gly Arg Ile Gly  Gly Gln Ile
    1190                1195                1200

His Leu Ala Ile Met Ala Val  Phe Lys Met Ser Pro  Gly Tyr Val
    1205                1210                1215

Leu Gly Val Phe Leu Arg Lys  Leu Thr Ser Arg Glu  Thr Ala Leu
    1220                1225                1230

Met Val Ile Gly Met Ala Met  Thr Thr Val Leu Ser  Ile Pro His
    1235                1240                1245

Asp Leu Met Glu Leu Ile Asp  Gly Ile Ser Leu Gly  Leu Ile Leu
    1250                1255                1260

Leu Lys Ile Val Thr Gln Phe  Asp Asn Thr Gln Val  Gly Thr Leu
    1265                1270                1275

Ala Leu Ser Leu Thr Phe Ile  Arg Ser Thr Met Pro  Leu Val Met
    1280                1285                1290

Ala Trp Arg Thr Ile Met Ala  Val Leu Phe Val Val  Thr Leu Ile
    1295                1300                1305

Pro Leu Cys Arg Thr Ser Cys  Leu Gln Lys Gln Ser  His Trp Val
    1310                1315                1320

Glu Ile Thr Ala Leu Ile Leu  Gly Ala Gln Ala Leu  Pro Val Tyr
    1325                1330                1335

Leu Met Thr Leu Met Lys Gly  Ala Ser Arg Arg Ser  Trp Pro Leu
    1340                1345                1350
```

-continued

```
Asn Glu Gly Ile Met Ala Val Gly Leu Val Ser Leu Leu Gly Ser
    1355                1360                1365

Ala Leu Leu Lys Asn Asp Val Pro Leu Ala Gly Pro Met Val Ala
    1370                1375                1380

Gly Gly Leu Leu Leu Ala Ala Tyr Val Met Ser Gly Ser Ser Ala
    1385                1390                1395

Asp Leu Ser Leu Glu Lys Ala Ala Asn Val Gln Trp Asp Glu Met
    1400                1405                1410

Ala Asp Ile Thr Gly Ser Ser Pro Ile Ile Glu Val Lys Gln Asp
    1415                1420                1425

Glu Asp Gly Ser Phe Ser Ile Arg Asp Val Glu Glu Thr Asn Met
    1430                1435                1440

Ile Thr Leu Leu Val Lys Leu Ala Leu Ile Thr Val Ser Gly Leu
    1445                1450                1455

Tyr Pro Leu Ala Ile Pro Val Thr Met Thr Leu Trp Tyr Met Trp
    1460                1465                1470

Gln Val Lys Thr Gln Arg Ser Gly Ala Leu Trp Asp Val Pro Ser
    1475                1480                1485

Pro Ala Ala Thr Lys Lys Ala Ala Leu Ser Glu Gly Val Tyr Arg
    1490                1495                1500

Ile Met Gln Arg Gly Leu Phe Gly Lys Thr Gln Val Gly Val Gly
    1505                1510                1515

Ile His Met Glu Gly Val Phe His Thr Met Trp His Val Thr Arg
    1520                1525                1530

Gly Ser Val Ile Cys His Glu Thr Gly Arg Leu Glu Pro Ser Trp
    1535                1540                1545

Ala Asp Val Arg Asn Asp Met Ile Ser Tyr Gly Gly Gly Trp Arg
    1550                1555                1560

Leu Gly Asp Lys Trp Asp Lys Glu Glu Asp Val Gln Val Leu Ala
    1565                1570                1575

Ile Glu Pro Gly Lys Asn Pro Lys His Val Gln Thr Lys Pro Gly
    1580                1585                1590

Leu Phe Lys Thr Leu Thr Gly Glu Ile Gly Ala Val Thr Leu Asp
    1595                1600                1605

Phe Lys Pro Gly Thr Ser Gly Ser Pro Ile Ile Asn Arg Lys Gly
    1610                1615                1620

Lys Val Ile Gly Leu Tyr Gly Asn Gly Val Val Thr Lys Ser Gly
    1625                1630                1635

Asp Tyr Val Ser Ala Ile Thr Gln Ala Glu Arg Ile Gly Glu Pro
    1640                1645                1650

Asp Tyr Glu Val Asp Glu Asp Ile Phe Arg Lys Lys Arg Leu Thr
    1655                1660                1665

Ile Met Asp Leu His Pro Gly Ala Gly Lys Thr Lys Arg Ile Leu
    1670                1675                1680

Pro Ser Ile Val Arg Glu Ala Leu Lys Arg Arg Leu Arg Thr Leu
    1685                1690                1695

Ile Leu Ala Pro Thr Arg Val Val Ala Ala Glu Met Glu Glu Ala
    1700                1705                1710

Leu Arg Gly Leu Pro Ile Arg Tyr Gln Thr Pro Ala Val Lys Ser
    1715                1720                1725

Glu His Thr Gly Arg Glu Ile Val Asp Leu Met Cys His Ala Thr
    1730                1735                1740

Phe Thr Thr Arg Leu Leu Ser Ser Thr Arg Val Pro Asn Tyr Asn
```

```
                1745                1750                1755

Leu Ile Val Met Asp Glu Ala His Phe Thr Asp Pro Ser Ser Val
        1760                1765                1770

Ala Ala Arg Gly Tyr Ile Ser Thr Arg Val Glu Met Gly Glu Ala
        1775                1780                1785

Ala Ala Ile Phe Met Thr Ala Thr Pro Pro Gly Ala Thr Asp Pro
        1790                1795                1800

Phe Pro Gln Ser Asn Ser Pro Ile Glu Asp Ile Glu Arg Glu Ile
        1805                1810                1815

Pro Glu Arg Ser Trp Asn Thr Gly Phe Asp Trp Ile Thr Asp Tyr
        1820                1825                1830

Gln Gly Lys Thr Val Trp Phe Val Pro Ser Ile Lys Ala Gly Asn
        1835                1840                1845

Asp Ile Ala Asn Cys Leu Arg Lys Ser Gly Lys Lys Val Ile Gln
        1850                1855                1860

Leu Ser Arg Lys Thr Phe Asp Thr Glu Tyr Pro Lys Thr Lys Leu
        1865                1870                1875

Thr Asp Trp Asp Phe Val Val Thr Thr Asp Ile Ser Glu Met Gly
        1880                1885                1890

Ala Asn Phe Arg Ala Gly Arg Val Ile Asp Pro Arg Arg Cys Leu
        1895                1900                1905

Lys Pro Val Ile Leu Pro Asp Gly Pro Glu Arg Val Ile Leu Ala
        1910                1915                1920

Gly Pro Ile Pro Val Thr Pro Ala Ser Ala Ala Gln Arg Arg Gly
        1925                1930                1935

Arg Ile Gly Arg Asn Pro Ala Gln Glu Asp Asp Gln Tyr Val Phe
        1940                1945                1950

Ser Gly Asp Pro Leu Lys Asn Asp Glu Asp His Ala His Trp Thr
        1955                1960                1965

Glu Ala Lys Met Leu Leu Asp Asn Ile Tyr Thr Pro Glu Gly Ile
        1970                1975                1980

Ile Pro Thr Leu Phe Gly Pro Glu Arg Glu Lys Thr Gln Ala Ile
        1985                1990                1995

Asp Gly Glu Phe Arg Leu Arg Gly Glu Gln Arg Lys Thr Phe Val
        2000                2005                2010

Glu Leu Met Arg Arg Gly Asp Leu Pro Val Trp Leu Ser Tyr Lys
        2015                2020                2025

Val Ala Ser Ala Gly Ile Ser Tyr Lys Asp Arg Glu Trp Cys Phe
        2030                2035                2040

Thr Gly Glu Arg Asn Asn Gln Ile Leu Glu Glu Asn Met Glu Val
        2045                2050                2055

Glu Ile Trp Thr Arg Glu Gly Glu Lys Lys Lys Leu Arg Pro Arg
        2060                2065                2070

Trp Leu Asp Ala Arg Val Tyr Ala Asp Pro Met Ala Leu Lys Asp
        2075                2080                2085

Phe Lys Glu Phe Ala Ser Gly Arg Lys Ser Ile Thr Leu Asp Ile
        2090                2095                2100

Leu Thr Glu Ile Ala Ser Leu Pro Thr Tyr Leu Ser Ser Arg Ala
        2105                2110                2115

Lys Leu Ala Leu Asp Asn Ile Val Met Leu His Thr Thr Glu Arg
        2120                2125                2130

Gly Gly Arg Ala Tyr Gln His Ala Leu Asn Glu Leu Pro Glu Ser
        2135                2140                2145
```

```
Leu Glu Thr Leu Met Leu Val Ala Leu Leu Gly Ala Met Thr Ala
2150                2155                2160

Gly Ile Phe Leu Phe Phe Met Gln Gly Lys Gly Ile Gly Lys Leu
    2165                2170                2175

Ser Met Gly Leu Ile Thr Ile Ala Val Ala Ser Gly Leu Leu Trp
    2180                2185                2190

Val Ala Glu Ile Gln Pro Gln Trp Ile Ala Ala Ser Ile Ile Leu
    2195                2200                2205

Glu Phe Phe Leu Met Val Leu Leu Ile Pro Glu Pro Glu Lys Gln
    2210                2215                2220

Arg Thr Pro Gln Asp Asn Gln Leu Ile Tyr Val Ile Leu Thr Ile
    2225                2230                2235

Leu Thr Ile Ile Gly Leu Ile Ala Ala Asn Glu Met Gly Leu Ile
    2240                2245                2250

Glu Lys Thr Lys Thr Asp Phe Gly Phe Tyr Gln Val Lys Thr Glu
    2255                2260                2265

Thr Thr Ile Leu Asp Val Asp Leu Arg Pro Ala Ser Ala Trp Thr
    2270                2275                2280

Leu Tyr Ala Val Ala Thr Thr Ile Leu Thr Pro Met Leu Arg His
    2285                2290                2295

Thr Ile Glu Asn Thr Ser Ala Asn Leu Ser Leu Ala Ala Ile Ala
    2300                2305                2310

Asn Gln Ala Ala Val Leu Met Gly Leu Gly Lys Gly Trp Pro Leu
    2315                2320                2325

His Arg Met Asp Leu Gly Val Pro Leu Leu Ala Met Gly Cys Tyr
    2330                2335                2340

Ser Gln Val Asn Pro Thr Thr Leu Thr Ala Ser Leu Val Met Leu
    2345                2350                2355

Phe Val His Tyr Ala Ile Ile Gly Pro Gly Leu Gln Ala Lys Ala
    2360                2365                2370

Thr Arg Glu Ala Gln Lys Arg Thr Ala Ala Gly Ile Met Lys Asn
    2375                2380                2385

Pro Thr Val Asp Gly Ile Thr Val Ile Asp Leu Glu Pro Ile Ser
    2390                2395                2400

Tyr Asp Pro Lys Phe Glu Lys Gln Leu Gly Gln Val Met Leu Leu
    2405                2410                2415

Val Leu Cys Ala Gly Gln Leu Leu Leu Met Arg Thr Thr Trp Ala
    2420                2425                2430

Phe Cys Glu Val Leu Thr Leu Ala Thr Gly Pro Ile Leu Thr Leu
    2435                2440                2445

Trp Glu Gly Asn Pro Gly Arg Phe Trp Asn Thr Thr Ile Ala Val
    2450                2455                2460

Ser Thr Ala Asn Ile Phe Arg Gly Ser Tyr Leu Ala Gly Ala Gly
    2465                2470                2475

Leu Ala Phe Ser Leu Ile Lys Asn Ala Gln Thr Pro Arg Arg Gly
    2480                2485                2490

Thr Gly Thr Thr Gly Glu Thr Leu Gly Glu Lys Trp Lys Arg Gln
    2495                2500                2505

Leu Asn Ser Leu Asp Arg Lys Glu Phe Glu Glu Tyr Lys Arg Ser
    2510                2515                2520

Gly Ile Leu Glu Val Asp Arg Thr Glu Ala Lys Ser Ala Leu Lys
    2525                2530                2535
```

```
Asp Gly Ser Lys Ile Lys His Ala Val Ser Arg Gly Ser Ser Lys
    2540                2545                2550

Ile Arg Trp Ile Val Glu Arg Gly Met Val Lys Pro Lys Gly Lys
    2555                2560                2565

Val Val Asp Leu Gly Cys Gly Arg Gly Gly Trp Ser Tyr Tyr Met
    2570                2575                2580

Ala Thr Leu Lys Asn Val Thr Glu Val Lys Gly Tyr Thr Lys Gly
    2585                2590                2595

Gly Pro Gly His Glu Glu Pro Ile Pro Met Ala Thr Tyr Gly Trp
    2600                2605                2610

Asn Leu Val Lys Leu His Ser Gly Val Asp Val Phe Tyr Lys Pro
    2615                2620                2625

Thr Glu Gln Val Asp Thr Leu Leu Cys Asp Ile Gly Glu Ser Ser
    2630                2635                2640

Ser Asn Pro Thr Ile Glu Glu Gly Arg Thr Leu Arg Val Leu Lys
    2645                2650                2655

Met Val Glu Pro Trp Leu Ser Ser Lys Pro Glu Phe Cys Ile Lys
    2660                2665                2670

Val Leu Asn Pro Tyr Met Pro Thr Val Ile Glu Glu Leu Glu Lys
    2675                2680                2685

Leu Gln Arg Lys His Gly Gly Asn Leu Val Arg Cys Pro Leu Ser
    2690                2695                2700

Arg Asn Ser Thr His Glu Met Tyr Trp Val Ser Gly Ala Ser Gly
    2705                2710                2715

Asn Ile Val Ser Ser Val Asn Thr Thr Ser Lys Met Leu Leu Asn
    2720                2725                2730

Arg Phe Thr Thr Arg His Arg Lys Pro Thr Tyr Glu Lys Asp Val
    2735                2740                2745

Asp Leu Gly Ala Gly Thr Arg Ser Val Ser Thr Glu Thr Glu Lys
    2750                2755                2760

Pro Asp Met Thr Ile Ile Gly Arg Arg Leu Gln Arg Leu Gln Glu
    2765                2770                2775

Glu His Lys Glu Thr Trp His Tyr Asp Gln Glu Asn Pro Tyr Arg
    2780                2785                2790

Thr Trp Ala Tyr His Gly Ser Tyr Glu Ala Pro Ser Thr Gly Ser
    2795                2800                2805

Ala Ser Ser Met Val Asn Gly Val Val Lys Leu Leu Thr Lys Pro
    2810                2815                2820

Trp Asp Val Ile Pro Met Val Thr Gln Leu Ala Met Thr Asp Thr
    2825                2830                2835

Thr Pro Phe Gly Gln Gln Arg Val Phe Lys Glu Lys Val Asp Thr
    2840                2845                2850

Arg Thr Pro Gln Pro Lys Pro Gly Thr Arg Met Val Met Thr Thr
    2855                2860                2865

Thr Ala Asn Trp Leu Trp Ala Leu Leu Gly Lys Lys Lys Asn Pro
    2870                2875                2880

Arg Leu Cys Thr Arg Glu Glu Phe Ile Ser Lys Val Arg Ser Asn
    2885                2890                2895

Ala Ala Ile Gly Ala Val Phe Gln Glu Glu Gln Gly Trp Thr Ser
    2900                2905                2910

Ala Ser Glu Ala Val Asn Asp Ser Arg Phe Trp Glu Leu Val Asp
    2915                2920                2925

Lys Glu Arg Ala Leu His Gln Glu Gly Lys Cys Glu Ser Cys Val
```

-continued

```
            2930                  2935                  2940
Tyr Asn Met Met Gly Lys Arg Glu Lys Leu Gly Glu Phe Gly
            2945                  2950                  2955
Arg Ala Lys Gly Ser Arg Ala Ile Trp Tyr Met Trp Leu Gly Ala
            2960                  2965                  2970
Arg Phe Leu Glu Phe Glu Ala Leu Gly Phe Leu Asn Glu Asp His
            2975                  2980                  2985
Trp Phe Gly Arg Glu Asn Ser Trp Ser Gly Val Glu Gly Glu Gly
            2990                  2995                  3000
Leu His Arg Leu Gly Tyr Ile Leu Glu Glu Ile Asp Lys Lys Asp
            3005                  3010                  3015
Gly Asp Leu Met Tyr Ala Asp Thr Ala Gly Trp Asp Thr Arg
            3020                  3025                  3030
Ile Thr Glu Asp Asp Leu Gln Asn Glu Glu Leu Ile Thr Glu Gln
            3035                  3040                  3045
Met Ala Pro His His Lys Ile Leu Ala Lys Ala Ile Phe Lys Leu
            3050                  3055                  3060
Thr Tyr Gln Asn Lys Val Val Lys Val Leu Arg Pro Thr Pro Arg
            3065                  3070                  3075
Gly Ala Val Met Asp Ile Ile Ser Arg Lys Asp Gln Arg Gly Ser
            3080                  3085                  3090
Gly Gln Val Gly Thr Tyr Gly Leu Asn Thr Phe Thr Asn Met Glu
            3095                  3100                  3105
Val Gln Leu Ile Arg Gln Met Glu Ala Glu Gly Val Ile Thr Gln
            3110                  3115                  3120
Asp Asp Met Gln Asn Pro Lys Gly Leu Lys Glu Arg Val Glu Lys
            3125                  3130                  3135
Trp Leu Lys Glu Cys Gly Val Ala Ala Leu Lys Arg Met Ala Ile
            3140                  3145                  3150
Ser Gly Asp Asp Cys Val Val Lys Pro Leu Asp Glu Arg Phe Gly
            3155                  3160                  3165
Thr Ser Leu Leu Phe Leu Asn Asp Met Gly Lys Val Arg Lys Asp
            3170                  3175                  3180
Ile Pro Gln Trp Glu Pro Ser Lys Gly Trp Lys Asn Trp Gln Glu
            3185                  3190                  3195
Val Pro Phe Cys Ser His His Phe His Lys Ile Phe Met Lys Asp
            3200                  3205                  3210
Gly Arg Ser Leu Val Val Pro Cys Arg Asn Gln Asp Glu Leu Ile
            3215                  3220                  3225
Gly Arg Ala Arg Ile Ser Gln Gly Ala Gly Trp Ser Leu Arg Glu
            3230                  3235                  3240
Thr Ala Cys Leu Gly Lys Ala Tyr Ala Gln Met Trp Ser Leu Met
            3245                  3250                  3255
Tyr Phe His Arg Arg Asp Leu Arg Leu Ala Ser Met Ala Ile Cys
            3260                  3265                  3270
Ser Ala Val Pro Thr Glu Trp Phe Pro Thr Ser Arg Thr Thr Trp
            3275                  3280                  3285
Ser Ile His Ala His His Gln Trp Met Thr Thr Glu Asp Met Leu
            3290                  3295                  3300
Lys Val Trp Asn Arg Val Trp Ile Glu Asp Asn Pro Asn Met Thr
            3305                  3310                  3315
Asp Lys Thr Pro Val His Ser Trp Glu Asp Ile Pro Tyr Leu Gly
            3320                  3325                  3330
```

```
Lys Arg Glu Asp Leu Trp Cys Gly Ser Leu Ile Gly Leu Ser Ser
    3335                3340                3345

Arg Ala Thr Trp Ala Lys Asn Ile His Thr Ala Ile Thr Gln Val
    3350                3355                3360

Arg Asn Leu Ile Gly Lys Glu Glu Tyr Val Asp Tyr Met Pro Val
    3365                3370                3375

Met Lys Arg Tyr Ser Ala Pro Ser Glu Ser Glu Gly Val Leu
    3380                3385                3390

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide primer 5' Den4

<400> SEQUENCE: 3
agttgttagt ctgtgtggac cgaca                                        25

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide primer 2546R

<400> SEQUENCE: 4
tctcgctggg gactctggtt gaaat                                        25

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide primer 2420F

<400> SEQUENCE: 5
agcagacatg ggttgtgtgg cgtc                                         24

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide primer 4588R

<400> SEQUENCE: 6
actccttcag acagtgcggc tttt                                         24

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide primer 4420F

<400> SEQUENCE: 7
cccttttggt gaaactggca ctga                                         24

<210> SEQ ID NO 8
<211> LENGTH: 24
<212> TYPE: DNA
<213> ORGANISM: Artificial Sequence
<220> FEATURE:
```

<223> OTHER INFORMATION: Synthetic oligonucleotide primer 6776R

<400> SEQUENCE: 8
ttgattgtct tgtggggtcc tttg                                            24

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide primer 6497F

<400> SEQUENCE: 9
ctatcaacac gccctgaacg aact                                            24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide primer 8989R

<400> SEQUENCE: 10
taccagattg ctcggcttcc cttg                                            24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide primer 8520F

<400> SEQUENCE: 11
atggtgaacg gggtggtaaa actg                                            24

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide primer 10610R

<400> SEQUENCE: 12
gctctgtgcc tggattgatg ttg                                             23

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide primer - DEN4 +
      strand 5'

<400> SEQUENCE: 13
ccagagtccc cagcgagact ag                                              22

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide primer - DEN4 +
      strand 3'

<400> SEQUENCE: 14
gccaaggggt agagacctga c                                               21

<210> SEQ ID NO 15
<211> LENGTH: 26
<212> TYPE: DNA
<213> ORGANISM: Artificial Sequence
<220> FEATURE:
<223> OTHER INFORMATION: Synthetic oligonulceotide primer - DEN4 -
      strand 5'

<400> SEQUENCE: 15
ctccatgacg ccacacaacc catgtc                                          26

<210> SEQ ID NO 16
<211> LENGTH: 28
<212> TYPE: DNA
<213> ORGANISM: Artificial Sequence
<220> FEATURE:
<223> OTHER INFORMATION: Synthetic oligonucleotide primer - DEN4 -
      strand 3'

<400> SEQUENCE: 16
ctcagaaacc caggattcgc gctcttgg                                        28

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide primer - TBE +
      strand 5'

<400> SEQUENCE: 17
gccacagtgc ggaaggaaag ag                                              22

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide primer - TBE +
      strand 3'

<400> SEQUENCE: 18
ggatcttggg caagaacccc actc                                            24

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer - TBE -
      strand 5'

<400> SEQUENCE: 19
caccgccaag aactgtgtgc a                                               21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer - TBE -
      strand 3'

<400> SEQUENCE: 20
gaccgtggaa agtgtggtga c                                               21

<210> SEQ ID NO 21
<211> LENGTH: 24
<212> TYPE: DNA
<213> ORGANISM: Artificial Sequence
<220> FEATURE:
<223> OTHER INFORMATION: Synthetic oligonucleotide primer - LGT +
      strand 5'

<400> SEQUENCE: 21
cagcgactgt gattgtggat attc                                          24

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide primer - LGT +
      strand 3'

<400> SEQUENCE: 22
aaggttgggt tcctcatgtt caagc                                         25

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide primer - LGT -
      strand 5'

<400> SEQUENCE: 23
actggccggt agaaacagct t                                             21

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide primer - LGT -
      strand 3'

<400> SEQUENCE: 24
aaggttgggt tcctcatgtt caagc                                         25

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide pimer - LGT/DEN -
      strand 5'

<400> SEQUENCE: 25
cgctcctccc aggacggtgt gc                                            22

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonulceotide primer - LGT/DEN -
      strand 3'

<400> SEQUENCE: 26
gcgtcgagat gcacccacct gga                                           23

<210> SEQ ID NO 27
<211> LENGTH: 10649
<212> TYPE: DNA
<213> ORGANISM: Dengue virus type 4

<400> SEQUENCE: 27

```
agttgttagt ctgtgtggac cgacaaggac agttccaaat cggaagcttg cttaacacag     60
ttctaacagt ttgtttgaat agagagcaga tctctggaaa aatgaaccaa cgaaaaaagg    120
tggttagacc acctttcaat atgctgaaac gcgagagaaa ccgcgtatca acccctcaag    180
ggttggtgaa gagattctca accggacttt tttctgggaa aggaccctta cggatggtgc    240
tagcattcat cacgtttttg cgagtccttt ccatcccacc aacagcaggg attctgaaga    300
gatggggaca gttgaagaaa aataaggcca tcaagatact gattggattc aggaaggaga    360
taggccgcat gctgaacatc ttgaacggga gaaaaaggtc aacgataaca ttgctgtgct    420
tgattcccac cgtaatggcg ttttccctca gcacaagaga tggcgaaccc ctcatgatag    480
tggcaaaaca tgaaaggggg agacctctct tgtttaagac aacagagggg atcaacaaat    540
gcactctcat tgccatggac ttgggtgaaa tgtgtgagga cactgtcacg tataaatgcc    600
ccctactggt caataccgaa cctgaagaca ttgattgctg gtgcaacctc acgtctacct    660
gggtcatgta tgggacatgc acccagagcg gagaacggag acgagagaag cgctcagtag    720
ctttaacacc acattcagga atgggattgg aaacaagagc tgagacatgg atgtcatcgg    780
aaggggcttg gaagcatgct cagagagtag agagctggat actcagaaac ccaggattcg    840
cgctcttggc aggatttatg gcttatatga ttgggcaaac aggaatccag cgaactgtct    900
tctttgtcct aatgatgctg gtcgccccat cctacggaat gcgatgcgta ggagtaggaa    960
acagagactt tgtggaagga gtctcaggtg gagcatgggt cgacctggtg ctagaacatg   1020
gaggatgcgt cacaaccatg gcccagggaa aaccaacctt ggattttgaa ctgactaaga   1080
caacagccaa ggaagtggct ctgttaagaa cctattgcat tgaagcctca atatcaaaca   1140
taactacggc aacaagatgt ccaacgcaag gagagcctta tctgaaagag gaacaggacc   1200
aacagtacat ttgccggaga gatgtggtag acagagggtg gggcaatggc tgtggcttgt   1260
ttggaaaagg aggagttgtg acatgtgcga agttttcatg ttcggggaag ataacaggca   1320
atttggtcca aattgagaac cttgaataca cagtggttgt aacagtccac aatggagaca   1380
cccatgcagt aggaaatgac acatccaatc atggagttac agccatgata actcccaggt   1440
caccatcggt ggaagtcaaa ttgccggact atggagaact aacactcgat tgtgaaccca   1500
ggtctggaat tgactttaat gagatgattc tgatgaaaat gaaaaagaaa acatggctcg   1560
tgcataagca atggtttttg gatctgcctc ttccatggac agcaggagca gacacatcag   1620
aggttcactg gaattacaaa gagagaatgg tgacatttaa ggttcctcat gccaagagac   1680
aggatgtgac agtgctggga tctcaggaag gagccatgca ttctgccctc gctggagcca   1740
cagaagtgga ctccggtgat ggaaatcaca tgtttgcagg acatcttaag tgcaaagtcc   1800
gtatggagaa attgagaatc aagggaatgt catacacgat gtgttcagga aagttttcaa   1860
ttgacaaaga gatggcagaa acacagcatg ggacaacagt ggtgaaagtc aagtatgaag   1920
gtgctggagc tccgtgtaaa gtccccatag agataagaga tgtaaacaag gaaaaagtgg   1980
ttgggcgtat catctcatcc accccttttgg ctgagaatac caacagtgta accaacatag   2040
aattagaacc cccctttggg gacagctaca tagtgatagg tgttggaaac agcgcattaa   2100
cactccattg gttcaggaaa gggagttcca ttggcaagat gtttgagtcc acatacagag   2160
```

```
gtgcaaaacg aatggccatt ctaggtgaaa cagcttggga ttttggttcc gttggtggac    2220
tgttcacatc attgggaaag gctgtgcacc aggttttttgg aagtgtgtat acaaccatgt   2280
ttggaggagt ctcatggatg attagaatcc taattgggtt cttagtgttg tggattggca    2340
cgaactcgag gaacacttca atggctatga cgtgcatagc tgttggagga atcactctgt    2400
ttctgggctt cacagttcaa gcagacatgg gttgtgtggc gtcatggagt gggaaagaat    2460
tgaagtgtgg aagcggaatt tttgtggttg acaacgtgca cacttggaca gaacagtaca    2520
aatttcaacc agagtcccca gcgagactag cgtctgcaat attaaatgcc cacaaagatg    2580
gggtctgtgg aattagatca accacgaggc tggaaaatgt catgtggaag caaataacca    2640
acgagctaaa ctatgttctc tgggaaggag gacatgacct cactgtagtg gctggggatg    2700
tgaagggggt gttgaccaaa ggcaagagag cactcacacc cccagtgagt gatctgaaat    2760
attcatggaa gacatgggga aaagcaaaaa tcttcacccc agaagcaaga aatagcacat    2820
ttttaataga cggaccagac acctctgaat gccccaatga acgaagagca tggaactctc    2880
ttgaggtgga agactatgga tttggcatgt tcacgaccaa catatggatg aaattccgag    2940
aaggaagttc agaagtgtgt gaccacaggt taatgtcagc tgcaattaaa gatcagaaag    3000
ctgtgcatgc tgacatgggt tattggatag agagctcaaa aaaccagacc tggcagatag    3060
agaaagcatc tcttattgaa gtgaaaacat gtctgtggcc caagacccac acactgtgga    3120
gcaatggagt gctggaaagc cagatgctca ttccaaaatc atatgcgggc ccttttttcac    3180 agcacaatta ccgccagggc tatgccacgc aaaccgtggg cccatggcac ttaggcaaat    3240
tagagataga ctttgagaa tgcccccggaa caacagtcac aattcaggag gattgtgacc    3300
atagaggccc atctttgagg accaccactg catctggaaa actagtcacg caatggtgct    3360
gccgctcctg cacgatgcct cccttaaggt tcttgggaga agatgggtgc tggtatggga    3420
tggagattag gccttgagt gaaaagaag agaacatggt caaatcacag gtgacggccg    3480
gacagggcac atcagaaact ttttctatgg gtctgttgtg cctgaccttg tttgtggaag    3540
aatgcttgag gagaagagtc actaggaaac acatgatatt agttgtggtg atcactcttt    3600
gtgctatcat cctgggaggc ctcacatgga tggacttact acgagccctc atcatgttgg    3660
gggacactat gtctggtaga ataggaggac agatccacct agccatcatg gcagtgttca    3720
agatgtcacc aggatacgtg ctgggtgtgt tttaaggaa actcacttca agagagacag    3780
cactaatggt aataggaatg ccatgacaa cggtgctttc aattccacat gaccttatgg    3840
aactcattga tggaatatca ctgggactaa ttttgctaaa aatagtaaca cagttttgaca    3900 acacccaagt gggaacctta gctctttcct tgactttcat aagatcaaca atgccattgg    3960
tcatggcttg gaggaccatt atggctgtgt tgtttgtggt cacactcatt cctttgtgca    4020
ggacaagctg tcttcaaaaa cagtctcatt gggtagaaat aacagcactc atcctaggag    4080
cccaagctct gccagtgtac ctaatgactc ttatgaaagg agcctcaaga agatcttggc    4140
ctcttaacga gggcataatg gctgtgggtt tggttagtct cttaggaagc gctctttttaa    4200 agaatgatgt cccctttagct ggcccaatgg tggcaggagg cttacttctg gcggcttacg    4260
tgatgagtgg tagctcagca gatctgtcac tagagaaggc cgccaacgtg cagtgggatg    4320
aaatggcaga cataacaggc tcaagcccaa tcgtagaagt gaagcaggat gaagatggct    4380
ctttctccat acgggacgtc gaggaaacca atatgataac cttttggtg aaactggcac    4440 tgataacagt gtcaggtctc taccccttgg caattccagt cacaatgacc ttatggtaca    4500
tgtggcaagt gaaaacacaa agatcaggag ccctgtggga cgtcccctca cccgctgcca    4560
```

```
ctaaaaaagc cgcactgtct gaaggagtgt acaggatcat gcaaagaggg ttattcggga   4620
aaactcaggt tggagtaggg atacacatgg aaggtgtatt tcacacaatg tggcatgtaa   4680
caagaggatc agtgatctgc cacgagactg ggagattgga gccatcttgg gctgacgtca   4740
ggaatgacat gatatcatac ggtgggggat ggaggcttgg agacaaatgg gacaaagaag   4800
aagacgttca ggtcctcgcc atagaaccag gaaaaaatcc taaacatgtc caaacgaaac   4860
ctggcctttt caagacccta actggagaaa ttggagcagt aacattagat ttcaaacccg   4920
gaacgtctgg ttctcccatc atcaacagga aggaaaagt catcggactc tatggaaatg   4980
gagtagttac caaatcaggt gattacgtca gtgccataac gcaagccgaa agaattggag   5040
agccagatta tgaagtggat gaggacattt tcgaaagaa aagattaact ataatggact   5100
tacaccccgg agctggaaag acaaaaagaa ttcttccatc aatagtgaga gaagccttaa   5160
aaaggaggct acgaactttg attttagctc ccacgagagt ggtggcggcc gagatggaag   5220
aggccctacg tggactgcca atccgttatc agacccccagc tgtgaaatca gaacacacag   5280
gaagagagat tgtagacctc atgtgtcatg caaccttcac aacaagactt ttgtcatcaa   5340
ccagggttcc aaattacaac cttatagtga tggatgaagc acatttcacc gatccttcta   5400
gtgtcgcggc tagaggatac atctcgacca gggtggaaat gggagaggca gcagccatct   5460
tcatgaccgc aaccccctccc ggagcgacag atccctttcc ccagagcaac agcccaatag   5520
aagacatcga gagggaaatt ccggaaaggt catggaacac agggttcgac tggataacag   5580
actaccaagg gaaaactgtg tggtttgttc ccagcataaa agctggaaat gacattgcaa   5640
attgtttgag aaagtcggga aagaaagtta tccagttgag taggaaaacc tttgatacag   5700
agtatccaaa aacgaaactc acggactggg actttgtggt cactacagac atatctgaaa   5760
tgggggccaa ttttagagcc gggagagtga tagaccctag aagatgcctc aagccagtta   5820
tcctaccaga tgggccagag agagtcattt tagcaggtcc tattccagtg actccagcaa   5880
gcgctgctca gagaagaggg cgaataggaa ggaacccagc acaagaagac gaccaatacg   5940
ttttctccgg agacccacta aaaaatgatg aagatcatgc ccactggaca gaagcaaaga   6000
tgctgcttga caatatctac acccccagaag ggatcattcc aacattgttt ggtccggaaa   6060
gggaaaaaac ccaagccatt gatggagagt ttcgcctcag aggggaacaa aggaagactt   6120
ttgtggaatt aatgaggaga ggagacctcc cggtgtggct gagctataag gtagcttctg   6180
ctggcatttc ttacgaagat cgggaatggt gcttcacagg ggaaagaaat aaccaaattt   6240
tagaagaaaa catggaggtt gaaatttgga ctagagaggg agaaaagaaa agctaaggc   6300 caagatggtt agatgcacgt gtatacgctg accccatggc tttgaaggat tcaaggagt   6360 ttgccagtgg aagaagagt ataactctcg acatcctaac agagattgcc agtttgccaa   6420
cttacctttc ctctagggcc aagctcgccc ttgataacat agtcatgctc cacacaacag   6480
aaagaggagg gagggcctat caacacgccc tgaacgaact tccggagtca ctggaaacac   6540
tcatgcttgt agctttacta ggtgctatga cagcaggcat cttcctgttt ttcatgcaag   6600
ggaaaggaat agggaaattg tcaatgggtt tgataaccat tgcggtggct agtggcttgc   6660
tctgggtagc agaaattcaa ccccagtgga tagcggcctc aatcatacta gagttttttc   6720
tcatggtact gttgataccg gaaccagaaa acaaaggac cccacaagac aatcaattga   6780
tctacgtcat attgaccatt ctcaccatca ttggtctaat agcagccaac gagatggggc   6840
tgattgaaaa aacaaaacg gattttgggt tttaccaggt aaaaacagaa accaccatcc   6900
```

```
tcgatgtgga cttgagacca gcttcagcat ggacgctcta tgcagtagcc accacaattc    6960
tgactcccat gctgagacac accatagaaa acacgtcggc caacctatct ctagcagcca    7020
ttgccaacca ggcagccgtc ctaatggggc ttggaaaagg atggccgctc cacagaatgg    7080
acctcggtgt gccgctgtta gcaatgggat gctattctca agtgaaccca acaaccttga    7140
cagcatcctt agtcatgctt ttagtccatt atgcaataat aggcccagga ttgcaggcaa    7200
aagccacaag agaggcccag aaaaggacag ctgctgggat catgaaaaat cccacagtgg    7260
acgggataac agtaatagat ctagaaccaa tatcctatga cccaaaattt gaaaagcaat    7320
tagggcaggt catgctacta gtcttgtgtg ctggacaact actcttgatg agaacaacat    7380
gggctttctg tgaagtcttg actttggcca caggaccaat cttgaccttg tgggagggca    7440
acccgggaag gttttggaac acgaccatag ccgtatccac cgccaacatt ttcaggggaa    7500
gttacttggc gggagctgga ctggcttttt cactcataaa gaatgcacaa cccctagga    7560 ggggaactgg gaccacagga gagacactgg gagagaagtg gaagagacag ctaaactcat    7620
tagacagaaa agagtttgaa gagtataaaa gaagtggaat actagaagtg gacaggactg    7680
aagccaagtc tgccctgaaa gatgggtcta aaatcaagca tgcagtatca agagggtcca    7740
gtaagatcag atggattgtt gagagaggga tggtaaagcc aaaagggaaa gttgtagatc    7800
ttggctgtgg gagaggagga tggtcttatt acatggcgac actcaagaac gtgactgaag    7860
tgaaagggta tacaaaagga ggtccaggac atgaagaacc gattcccatg ctacttatg    7920 gttggaattt ggtcaaactc cattcagggg ttgacgtgtt ctacaaaccc acagagcaag    7980
tggacaccct gctctgtgat attggggagt catcttctaa tccaacaata gaggaaggaa    8040
gaacattaag agttttgaag atggtggagc catggctctc ttcaaaacct gaattctgca    8100
tcaaagtcct taaccctac atgccaacag tcatagaaga gctggagaaa ctgcagagaa    8160
aacatggtgg gaaccttgtc agatgcccgc tgtccaggaa ctccaccat gagatgtatt    8220 gggtgtcagg agcgtcggga acattgtga gctctgtgaa cacaacatca aagatgttgt    8280
tgaacaggtt cacaacaagg cataggaaac ccacttatga aaggacgta gatcttgggg    8340 caggaacgag aagtgtctcc actgaaacag aaaaaccaga catgacaatc attgggagaa    8400
ggcttcagcg attgcaagaa gagcacaaag aaacctggca ttatgatcag gaaaacccat    8460
acagaacctg gcgtatcat ggaagctatg aagctccttc gacaggctct gcatcctcca    8520
tggtgaacgg ggtggtaaaa ctgctaacaa accctgggga tgtgattcca atggtgactc    8580
agttagccat gacagataca accccttttg ggcaacaaag agtgttcaaa gagaaggtgg    8640
ataccagaac accacaacca aaacccggta cacgaatggt tatgaccacg acagccaatt    8700
ggctgtgggc cctccttgga aagaagaaaa atcccagact gtgcacaagg gaagagttca    8760
tctcaaaagt tagatcaaac gcagccatag cgcagtctt tcaggaagaa cagggatgga    8820
catcagccag tgaagctgtg aatgacagcc ggttttggga actggttgac aaagaaaggg    8880
ccctacacca ggaagggaaa tgtgaatcgt gtgtctataa catgatggga aaacgtgaga    8940
aaaagttagg agagtttggc agagccaagg gaagccgagc aatctggtac atgtggctgg    9000
gagcgcggtt tctggaattt gaagccctgg ttttttgaa tgaagatcac tggtttggca    9060
gagaaaattc atggagtgga gtggaagggg aaggtctgca cagattggga tatatcctgg    9120
aggagataga caagaaggat ggagacctaa tgtatgctga tgacacagca ggctgggaca    9180
caagaatcac tgaggatgac cttcaaaatg aggaactgat cacggaacag atggctcccc    9240
accacaagat cctagccaaa gccatttca aactaaccta tcaaaacaaa gtggtgaaag    9300
```

```
tcctcagacc cacaccgcgg ggagcggtga tggatatcat atccaggaaa gaccaaagag     9360
gtagtggaca agttggaaca tatggtttga acacattcac caacatggaa gttcaactca     9420
tccgccaaat ggaagctgaa ggagtcatca cacaagatga catgcagaac ccaaaagggt     9480
tgaaagaaag agttgagaaa tggctgaaag agtgtggtgt cgacaggtta aagaggatgg     9540
caatcagtgg agacgattgc gtggtgaagc ccctagatga gaggtttggc acttccctcc     9600
tcttcttgaa cgacatggga aaggtgagga agacattcc gcagtgggaa ccatctaagg      9660
gatggaaaaa ctggcaagag gttccttttt gctcccacca ctttcacaag atctttatga     9720
aggatggccg ctcactagtt gttccatgta gaaaccagga tgaactgata gggagagcca    9780
gaatctcgca gggagctgga tggagcttaa gagaaacagc ctgcctgggc aaagcttacg     9840
cccagatgtg gtcgcttatg tacttccaca gaagggatct gcgtttagcc tccatggcca    9900
tatgctcagc agttccaacg gaatggtttc caacaagcag aacaacatgg tcaatccacg    9960
ctcatcacca gtggatgacc actgaagata tgctcaaagt gtggaacaga gtgtggatag   10020
aagacaaccc taatatgact gacaagactc cagtccattc gtgggaagat ataccttacc   10080
tagggaaaag agaggatttg tggtgtggat ccctgattgg actttcttcc agagccacct   10140
gggcgaagaa cattcatacg gccataaccc aggtcaggaa cctgatcgga aaagaggaat   10200
acgtggatta catgccagta atgaaaagat acagtgctcc ttcagagagt gaaggagttc   10260
tgtaattacc aacaacaaac accaaaggct attgaagtca ggccacttgt gccacggttt   10320
gagcaaaccg tgctgcctgt agctccgcca ataatgggag gcgtaataat ccccagggag   10380
gccatgcgcc acggaagctg tacgcgtggc atattggact agcggttaga ggagacccct   10440
cccatcactg ataaaacgca gcaaaagggg gcccgaagcc aggaggaagc tgtactcctg   10500
gtggaaggac tagaggttag aggagacccc cccaacacaa aaacagcata ttgacgctgg   10560
gaaagaccag agatcctgct gtctctgcaa catcaatcca ggcacagagc gccgcaagat   10620
ggattggtgt tgttgatcca acaggttct                                     10649
```

ANTIGENIC CHIMERIC TICK-BORNE ENCEPHALITIS VIRUS/DENGUE VIRUS TYPE 4 RECOMBINANT VIRUSES

CROSS-REFERENCE TO RELATED APPLICATIONS

This is a divisional of U.S. patent application Ser. No. 13/322,317, filed Nov. 23, 2011, which is the U.S. National Stage of International Application No. PCT/US2010/036678, filed May 28, 2010, which was published in English under PCT Article 21(2), which in turn claims the benefit of U.S. Provisional Patent Application No. 61/181,982, filed May 28, 2009, all of which are incorporated herein by reference in their entirety.

FIELD OF THE DISCLOSURE

This disclosure relates to chimeric flaviviruses, particularly chimeric tick-borne encephalitis virus/dengue virus type 4 chimeras. Further, it relates to methods of eliciting an immune response to tick-borne encephalitis virus in a host utilizing the disclosed chimeric flaviviruses.

BACKGROUND

The tick-borne encephalitis virus (TBEV) complex is a group of viruses that cause severe neurotropic disease and up to 30% mortality. While these viruses can be found in many parts of the world, the largest impact of disease occurs in Europe and Russia, where approximately 14,000 hospitalized TBEV cases occur annually. Furthermore, the majority of TBEV cases are considered to be subclinical, indicating a higher incidence of TBEV infection than is generally recognized. The tick-borne encephalitis complex includes TBEV (e.g., European, Siberian, and Far Eastern subtypes), as well as Omsk hemorrhagic fever, Kyasanur forest disease, Langat, Louping ill, Negishi, and Powassan viruses.

TBEV is in the family Flaviviridae, genus *Flavivirus* and is composed of a positive-sense single stranded RNA genome that contains 5' and 3' non-coding regions (NCR) and a single open reading frame encoding 10 proteins. The proteins are co- and post-translationally cleaved by viral and host proteins to derive three structural proteins (capsid (C), membrane (M), and envelope (E)), and seven non-structural proteins (NS1, NS2A, NS2B, NS3, NS4A, NS4B, and NS5). The non-structural proteins regulate viral transcription and replication and attenuate antiviral responses, while the structural proteins compose the outer shell of the virus and are, therefore, significant effectors of host immunogenicity.

SUMMARY OF THE DISCLOSURE

Disclosed herein are recombinant chimeric TBEV/DEN4 flaviviruses including 5' and 3' non-coding regions, a C protein, and non-structural proteins from DEN4 virus, and a prM protein and E protein from TBEV. In particular examples, the chimeric TBEV/DEN4 virus includes a first nucleic acid molecule including a 5' non-coding region from a DEN4 virus, a nucleic acid encoding a C protein from a DEN4 virus, non-structural proteins from a DEN4 virus, and a 3' non-coding region from a DEN4 virus, wherein nonstructural protein NS4B includes a phenylalanine at amino acid position 112, nonstructural protein NS5 includes an alanine at amino acid position 654 and an alanine at amino acid position 655, and the 3' non-coding region includes a deletion of nucleotides 10478-10507 (Δ30). The chimeric TBEV/DEN4 virus also includes a second nucleic acid molecule which is operably linked to the first nucleic acid molecule, the second nucleic acid molecule encoding a prM protein from a TBEV and an E protein from a TBEV, and wherein the E protein includes an amino acid substitution that differs from the wild type TBEV at amino acid position 315 and a tryptophan at amino acid position 240. In one example, the chimeric TBEV/DEN4 flavivirus construct includes aspartic acid at amino acid 315 of the TBEV E protein. In particular examples, the chimeric TBEV/DEN4 flavivirus encodes a polypeptide at least 95% identical to SEQ ID NO: 2 or includes a nucleic acid molecule at least 95% identical to SEQ ID NO: 1. In further examples, the chimeric TBEV/DEN4 flavivirus construct includes additional amino acid substitutions, such as at amino acid 84 of the TBEV E protein and/or amino acid 6 of the NS1 protein of DEN4.

Further disclosed herein is a recombinant TBEV/DEN4 chimeric virus that can be used to produce pseudoinfectious or replication-deficient TBEV/DEN4 viruses. In some examples, the TBEV/DEN4 chimera lacks at least one structural protein, such as the C protein, prM protein, and/or E protein. The deleted structural proteins are provided in a separate construct. In one example, the chimeric virus includes a first nucleic acid molecule including a 5' non-coding region from a DEN 4 virus; a nucleic acid encoding non-structural proteins from a DEN 4 virus, wherein non-structural protein NS4B comprises a phenylalanine at amino acid position 112, and nonstructural protein NS5 comprises an alanine at amino acid position 654 and an alanine at amino acid position 655; and a 3' non-coding region from a DEN 4 virus, wherein the 3' non-coding region comprises a deletion of nucleotides 10478-10507; and a second nucleic acid molecule operably linked to the first nucleic acid molecule, the second nucleic acid molecule encoding a prM protein from a TBEV; and an E protein from a TBEV, wherein the E protein comprises an amino acid substitution from wild-type at amino acid position 315 and a tryptophan at amino acid position 240, wherein the chimeric virus does not encode a C protein.

Also disclosed herein are methods of eliciting an immune response to TBEV in a subject, including administering a disclosed recombinant TBEV/DEN4 virus or a disclosed recombinant pseudoinfectious or replication-deficient TBEV/DEN4 virus to the subject. In addition, an immunogenic composition is disclosed, the composition including a recombinant TBEV/DEN4 virus including the disclosed nucleic acid chimeras and a pharmaceutically acceptable carrier. Methods of eliciting an immune response to TBEV or members of the TBEV complex, including administering a therapeutically effective amount of the immunogenic composition to a subject are also disclosed.

The foregoing and other features will become more apparent from the following detailed description, which proceeds with reference to the accompanying figures.

BRIEF DESCRIPTION OF THE FIGURES

FIG. 1 is a series of graphs showing replication of TBEV/DEN4Δ30 chimeras in Vero cells, human neuroblastoma SH-SY5Y cells, or human glioblastoma LN-18 cells at various temperatures. TBEV/DENΔ30, TBEV/DEN4Δ30 chimera; TBEV/DENΔ30/E-315, TBEV/DEN4Δ30/E-K$_{315}$D chimera; TBEV/DENΔ30/NS5-654,655, TBEV/DEN4Δ30/NS5-DR$_{654,655}$AA chimera; TBEV/DENΔ30/E-315/NS5-654,655, TBEV/DEN4Δ30/E-K$_{315}$D/NS5-DR$_{654,655}$AA chimera.

FIG. 2A is a graph showing viral replication kinetics of TBEV/DEN4Δ30 chimeras in the brains of 3 day-old Swiss mice inoculated intracerebrally (ic) with $10^3$ pfu of the indicated chimeric virus and harvested at the indicated days post-inoculation. TBEV/DEN4Δ30, TBEV/DEN4Δ30 chimera; TBEV/DEN4Δ30/E-315, TBEV/DEN4Δ30/E-$K_{315}$D chimera; TBEV/DEN4Δ30/NS5-654,655, TBEV/DEN4Δ30/NS5-$DR_{654,655}$AA chimera; TBEV/DEN4Δ30/E-315/NS5-654,655, TBEV/DEN4Δ30/E-$K_{315}$D/NS5-$DR_{654,655}$AA chimera FIG. 2B is a graph showing viral replication kinetics of TBEV/DEN4Δ30 chimeras in the brains of 5 day-old Swiss mice inoculated ic with $10^3$ pfu of the indicated chimeric virus and harvested at the indicated days post-inoculation. TBEV/DEN4Δ30, TBEV/DEN4Δ30 chimera; TBEV/DEN4Δ30/E-315, TBEV/DEN4Δ30/E-$K_{315}$D chimera; TBEV/DEN4Δ30/NS5-654,655, TBEV/DEN4Δ30/NS5-$DR_{654,655}$AA chimera; TBEV/DEN4Δ30/E-315/NS5-654,655, TBEV/DEN4Δ30/E-$K_{315}$D/NS5-$DR_{654,655}$AA chimera.

FIG. 3 is a series of digital images showing neuroinflammation in the brain of mice infected with chimeras TBEV/DEN4 (A, D, and G); TBEV/DEN4Δ30 (B, E, and H), or TBEV/DEN4Δ30/E-$K_{315}$D/NS5-$DR_{654,655}$AA (vΔ30/$E_{315}$/NS5; C, F, and I). Representative images of neuroinflammation in the brain on day 6 from mice ic inoculated with each virus (H&E staining). The boxed areas in A-C (20× magnification) are shown in D-F at higher magnification (40× magnification) and G-I show the boxed areas in D-F at higher magnification (100× magnification). Inflammatory foci are indicated by arrows and the dashed circle. Abbreviations: Cx, cortex; CA1, hippocampus; DG, dentate gyrus; Th, thalamus; Or, oriens layer of the hippocampus; Py, pyramidal layer of the hippocampus; rad, radiatum layer of the hippocampus.

FIG. 4 is a bar graph showing replication of the indicated viruses in the brains of 3-week-old SCID mice following intraperitoneal (ip) inoculation with $10^5$ pfu of virus. On the indicated days, three mouse brains per group were harvested and the virus titer of each mouse brain homogenate was determined by immunofocus assay on Vero cells. Mean virus titers±SE are indicated. The limit of detection of the assay was 1.7 $\log_{10}$ pfu/g.

FIG. 5A is a graph showing percent survival of adult Swiss mice inoculated intraperitoneally (ip) with the indicated TBEV/DEN4 chimeras followed by intracerebral (ic) challenge with 100 $icLD_{50}$ (1000 pfu) of TBEV/DEN4 virus four weeks later. TBEV/DEN4, TBEV/DEN4 chimera; TBEV/DEN4/E-315, TBEV/DEN4/E-$K_{315}$D chimera; TBEV/DEN4/NS5-654,655, TBEV/DEN4/NS5-$DR_{654,655}$AA chimera; TBEV/DEN4/E-315/NS5-654,655, TBEV/DEN4/E-$K_{315}$D/NS5-$DR_{654,655}$AA chimera; mock, vehicle.

FIG. 5B is a graph showing percent survival of adult Swiss mice inoculated ip with the indicated TBEV/DEN4Δ30 chimeras followed by ic challenge with 100 $icLD_{50}$ of TBEV/DEN4 virus four weeks later. TBEV/DEN4Δ30, TBEV/DEN4Δ30 chimera; TBEV/DEN4Δ30/E-315, TBEV/DEN4Δ30/E-$K_{315}$D chimera; TBEV/DEN4Δ30/NS5-654,655, TBEV/DEN4Δ30/NS5-$DR_{654,655}$AA chimera; TBEV/DEN4Δ30/E-315/NS5-654,655, TBEV/DEN4Δ30/E-$K_{315}$D/NS5-$DR_{654,655}$AA chimera; mock, vehicle.

FIG. 7 is a pair of graphs showing viral replication in simian Vero (A) or mosquito C6/36 (B) cells. Cells were infected with TBEV/DEN4Δ30 (♦), its derived mutant viruses (TBEV/DEN4Δ30/E-$K_{315}$D (□), TBEV/DEN4Δ30/NS5-DR-654,655AA (▲), TBEV/DEN4Δ30/E-$K_{315}$D/NS5-DR-654,655AA (x)), LGT (*), or DEN4 (Δ) viruses at an MOI of 1. Viral supernatants were taken every 24 hours post-infection for eight days, and were quantitated for viral titers. Each time point represents the mean viral titer from three replicates. Limit of detection was 2.0 $\log_{10}$ pfu/ml.

FIG. 8 is a graph showing virus titer in *Ae. aegypti* mosquitoes after 14 or 21 days incubation. The limit of detection was 0.4 $\log_{10}$/mosquito.

FIG. 9 is a series of digital images of agarose gel electrophoresis of RT-PCR amplified cDNA from virus, showing presence of viral RNA in ticks following infection. Total RNA was isolated from a group of 25 *I. scapularis* larvae at 21 days post immersion with media or the various viruses. Viral RNA was detected using primers specific for the (A) positive or (B) negative sense RNA. To detect TBEV/DEN4Δ30 and its derivatives (E-$K_{315}$D, NS5-$DR_{654,655}$AA and E-$K_{315}$D/NS5-$DR_{654,655}$AA), TBEV specific primers were used, whereas LGT- and DEN4-specific primers were used to detect LGT and DEN4 virus, respectively. Positive controls (+CNTRL) were total RNA isolated from virus infection in Vero cells. Molecular weight markers are displayed in the far left lanes. TBEV/DEN4Δ30, TBEV/DEN4Δ30 chimera; vΔ30/E315, TBEV/DEN4Δ30/E-$K_{315}$D chimera; vΔ30/NS5$_{654,655}$, TBEV/DEN4Δ30/NS5-$DR_{654,655}$AA chimera; vΔ30/E315/NS5$_{654,655}$, TBEV/DEN4Δ30/E-$K_{315}$D/NS5-$DR_{654,655}$AA chimera; mock, uninfected.

SEQUENCE LISTING

Figure 6:
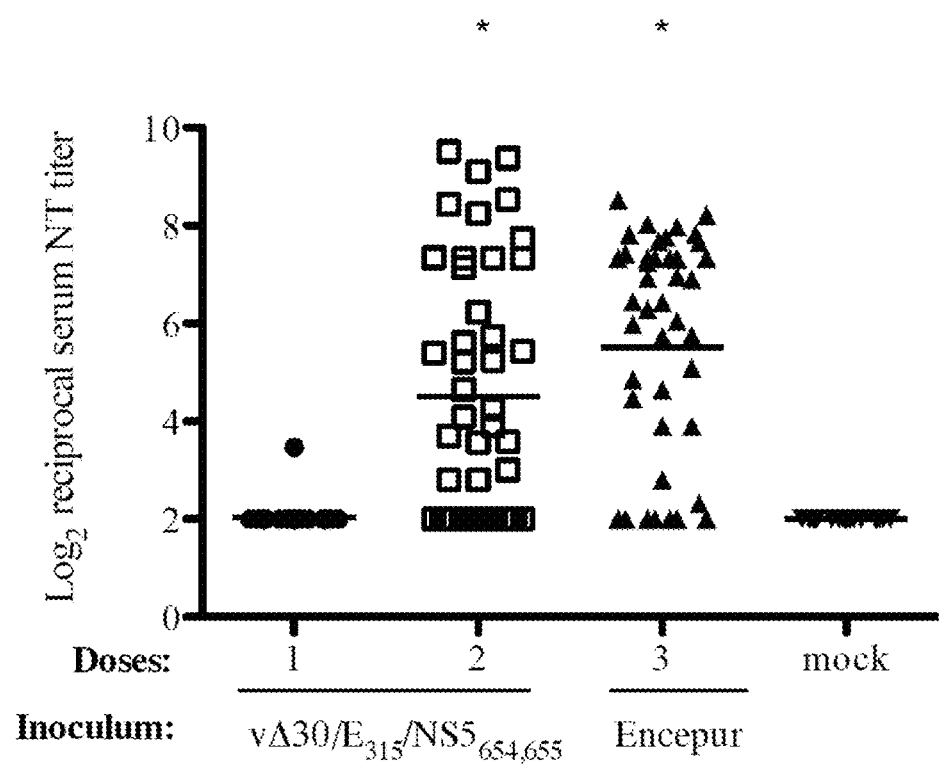
FIG. 6 is a scatter plot showing immunogenic response of mice inoculated with the indicated vaccines prior to challenge with wild-type TBEV strains. Mice were immunized with one or two doses ($10^5$ pfu) of live attenuated TBEV/DEN4Δ30/E315/NS5$_{654,655}$, three doses of inactivated Encepur® vaccine, or mock vaccinated. Serum neutralizing antibody titers were measured against TBEV/DEN4Δ30. Significant differences (designated by asterisks) were observed between one and two doses of TBEV/DEN4Δ30/E-$K_{315}$D/NS5-DR-654, 655AA (TBEV/DEN4Δ30/E315/NS5$_{654,655}$; p<0.05), whereas no significant differences were observed between two doses of TBEV/DEN4Δ30/E315/NS5$_{654,655}$ and three doses of Encepur® for neutralizing titers (p>0.05, one-way ANOVA followed by Tukey post-hoc or unpaired t test). Reciprocal mean titers are indicated by the bars.

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jul. 29, 2015, and is 101,791 bytes, which is incorporated by reference herein.

SEQ ID NO: 1 and 2 show the nucleic acid and amino acid sequence, respectively of a TBEV/DEN4Δ30 chimera including deletion of nucleotides 10478-10507 in the 3' NCR, R240W and $K_{315}$D mutations in the E protein, L112F mutation in the NS4B protein, and D654A and R655A mutations in the NS5 protein. The start and stop positions of the particular genes and proteins of the chimera are shown in Table 1.

TABLE 1

Start and stop positions of NCRs, structural proteins and nonstructural proteins in SEQ ID NOs: 1 and 2.

| Region | SEQ ID NO: 1 nucleotide start/stop position | SEQ ID NO: 2 amino acid start/stop position |
| --- | --- | --- |
| 5' NCR | 1-101 | — |
| C | 102-458 | 1-119 |
| prM | 459-950 | 120-283 |
| M | 726-950 | 209-283 |
| E | 951-2438 | 284-779 |
| NS1 | 2439-3494 | 780-1131 |
| NS2A | 3495-4148 | 1132-1349 |
| NS2B | 4149-4538 | 1350-1479 |
| NS3 | 4539-6392 | 1480-2097 |
| NS4A | 6393-6842 | 2098-2247 |
| NS4B | 6843-7577 | 2248-2492 |
| NS5 | 7578-10280 | 2493-3393 |
| 3' NCR | 10281-10633 | — |

SEQ ID NOs: 3-12 are primers used to amplify and sequence TBEV/DEN4 chimeric virus sequences.

SEQ ID NOs: 13 and 14 are forward and reverse primers, respectively, used to detect DEN4 positive-sense strand RNA.

SEQ ID NOs: 15 and 16 are forward and reverse primers, respectively, used to detect DEN4 negative-sense strand RNA.

SEQ ID NOs: 17 and 18 are forward and reverse primers, respectively, used to detect TBE positive-sense strand RNA.

SEQ ID NOs: 19 and 20 are forward and reverse primers, respectively, used to detect TBE negative-sense strand RNA.

SEQ ID NOs: 21 and 22 are forward and reverse primers, respectively, used to detect Langat positive-sense strand RNA.

SEQ ID NOs: 23 and 24 are forward and reverse primers, respectively, used to detect Langat negative-sense strand RNA.

SEQ ID NOs: 25 and 26 are forward and reverse primers, respectively, used to detect Langat/DEN negative-sense strand RNA.

SEQ ID NO: 27 is the nucleic acid sequence of an exemplary DEN4 virus.

DETAILED DESCRIPTION OF SEVERAL EMBODIMENTS

I. Abbreviations

AST: average survival time

DEN4: dengue virus type 4 dpi: days post-inoculation dpc: days post-challenge

EOP: efficiency of plaque formation hr: host range restriction ic: intracerebral ip: intraperitoneal $LD_{50}$: 50% lethal dose LGT: Langat virus NCR: non-coding region pfu: plaque forming units sc: subcutaneous TBEV: tick-borne encephalitis virus TBEV/DEN4: virus with prM and E genes (or proteins) from TBEV and remaining genome (genes, proteins, or NCRs) from DEN4

TBEV/DEN4Δ30: virus with prM and E genes (or proteins) from TBEV and remaining genome (genes, proteins, or NCRs) from DEN4 with a 30 nucleotide deletion in the DEN4 3' NCR ts: temperature sensitive

II. Terms

Unless otherwise explained, all technical and scientific terms used herein have the same meaning as commonly understood by one of ordinary skill in the art to which this disclosure belongs. The singular terms “a,” “an,” and “the” include plural referents unless the context clearly indicates otherwise. Similarly, the word “or” is intended to include “and” unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term “comprises” means “includes.” All publications, patent applications, patents, and other references mentioned herein are incorporated by reference in their entirety for all purposes. All GenBank Accession Nos. mentioned herein are incorporated by reference in their entirety as of May 28, 2009. In case of conflict, the present specification, including explanations of terms, will control. In addition, the materials, methods, and examples are illustrative only and not intended to be limiting.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one “light” (about 25 kDa) and one “heavy” (about 50-70 kDa) chain. The N-terminus of each chain defines a variable region of about 100 to 110 or more amino acids primarily responsible for antigen recognition. The terms “variable light chain” ($V_L$) and “variable heavy chain” ($V_H$) refer, respectively, to these light and heavy chains.

As used herein, the term “antibodies” includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a virus antigen, such as a flavivirus prM or E protein.

Attenuated: In the context of a live virus, such as a TBEV or DEN4 virus, the virus is attenuated if its ability to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection. In particular examples, an attenuated flavivirus exhibits reduced neurovirulence and/or neuroinvasiveness in a host (such as a mouse, non-human primate, or human).

Capsid protein (C): One of three flavivirus structural proteins. The C protein forms the viral capsid, which contains the viral nucleic acid.

Chimera: A molecule (e.g., gene, transcript, or protein) composed of parts that are of different origin (such as at least two nucleic acid or amino acid sequences) that, while typically unjoined in their native state, are joined or linked to form a single continuous molecule. A chimera may include nucleic acid or amino acid molecules that are joined end-to-end (for example, the amino-terminus of one molecule is joined to the carboxyl-terminus of a second molecule) or may include one molecule that is embedded within another molecule (for example, the amino-terminus and carboxyl-terminus of the chimera are from one molecule, while an intervening sequence comes from another molecule).

A chimera may include a chimeric protein, for example a protein that is composed of amino acid sequences from more than one protein. A chimera may also include a chimeric nucleic acid composed of nucleic acid molecules from more than one source, such as a chimeric nucleic acid which encodes a chimeric protein. In some examples, a chimera may include a chimeric genome, such as a flavivirus genome, which is composed of sequences from two or more flaviviruses. For example, a chimeric flavivirus genome may comprise nucleic acid molecules from more than one flavivirus genome, such as dengue virus (such as DEN4) and tick-borne encephalitis virus (such as Far Eastern, Central European, or Siberian TBEV subtypes). In some examples, a chimeric flavivirus includes one or more nucleic acids encoding one or more proteins from a first flavivirus and one or more nucleic acids encoding one or more proteins from a second flavivirus. In particular examples, a chimeric flavivirus includes a nucleic acid molecule encoding the non-structural proteins and C protein from a DEN4 virus genome linked to a nucleic acid molecule encoding a prM protein and E protein from a TBEV genome.

Conservative substitution: A substitution of one amino acid residue in a protein for a different amino acid residue having similar biochemical properties. Typically, conservative substitutions have little to no impact on the activity of a resulting polypeptide. For example, ideally, a flavivirus protein (such as a C, prM, E, or non-structural protein) including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleic acid that encodes that polypeptide using, for example, standard procedures such as site-directed mutagenesis or PCR. In one example, such variants can be readily selected for additional testing by infecting cells with a virus containing a variant protein and determining ability to replicate (for example as described in Example 1) or by producing virus containing a variant protein and determining its neurovirulence or neuroinvasion properties (for example, as described in Example 2).

Dengue virus: A member of the virus family Flaviviridae which is transmitted through the bite of the mosquitoes *Aedes aegypti* and *Aedes albopictus*. There are four antigenically distinct subtypes of dengue virus: dengue 1, dengue 2, dengue 3, and dengue 4. In particular examples, the dengue virus is dengue 4 virus.

The most common symptoms of dengue are high fever, severe headache, backache, joint pains, nausea and vomiting, eye pain, and rash. Dengue hemorrhagic fever is characterized by a fever that lasts from 2 to 7 days, with symptoms such as nausea, vomiting, abdominal pain, and headache. This stage is followed by hemorrhagic manifestations, such as tendency to bruise easily, nose bleed, and possibly internal bleeding. The capillaries become excessively permeable, allowing the fluid component to escape from the blood vessels. Dengue hemorrhagic fever or Dengue shock syndrome can be fatal (about 5% fatality rate).

Envelope protein (E): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface.

Host: A cell or organism which harbors another organism or biological entity, for example a parasite or a virus. In some examples, a host is a small mammal (e.g., a rodent), human, or non-human primate that can be or is infected by a tick-borne encephalitis virus (such as Far Eastern, Central European, or Siberian TBEV subtypes) or a dengue virus (such as DEN1, DEN2, DEN3, or DEN4).

Immune response: A response of a cell of the immune system, such as a B-cell, T-cell, macrophage or polymorphonucleocyte, to a stimulus such as an antigen. An immune response can include any cell of the body involved in a host defense response, for example, an epithelial cell that secretes an interferon or a cytokine. An immune response includes, but is not limited to, an innate immune response or inflammation.

Immunize: To render a subject protected from an infectious disease, such as by vaccination.

Immunogen: A compound, composition, or substance that is capable, under appropriate conditions, of stimulating an immune response, such as the production of antibodies or a T-cell response in an animal, including compositions that are injected or absorbed into an animal. As used herein, an "immunogenic composition" is a composition comprising an immunogen.

Isolated: An "isolated" or "purified" biological component (such as a nucleic acid, peptide, protein, protein complex, virus, or particle) has been substantially separated, produced apart from, or purified away from other biological components in the cell of the organism in which the component naturally occurs, for example, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Non-structural protein: One of the non-structural (NS) proteins of a flavivirus, which are designated NS1, NS2A, NS2B, NS3, NS4A, NS4B, and NS5. The non-structural proteins are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222:159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). The function of NS2A is unknown. NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and immune modulation (Lindenbach and Rice, In: *Fields Virology*, Knipe and Howley, eds., Lippincott, Williams, and Wilkins, 991-1041, 2001; Muñoz-Jordán et al., *Proc. Natl. Acad. Sci. USA* 100:14333-14338, 2003; Muñoz-Jordán et al., *J. Virol.* 79:8004-8013, 2005). Finally, the NS5 protein is an RNA-dependent RNA polymerase involved in genome replication (Rice et al., *Science* 229:726-733, 1985). NS5 also shows methyltransferase activity commonly found in RNA capping enzymes and modulates the antiviral response through interferon antagonism (Koonin, *J. Gen. Virol.* 74:733-740, 1993; Best et al., *J. Virol.* 79:12828-12839, 2005).

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxyribonucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of nucleic acids. A polynucleotide may include either or both naturally occurring and modified nucleotides linked together by naturally occurring and/or non-naturally occurring nucleotide linkages.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Pharmaceutically acceptable carrier: The pharmaceutically acceptable carriers (vehicles) useful in this disclosure are conventional. *Remington: The Science and Practice of Pharmacy*, University of the Sciences in Philadelphia, Lippincott Williams & Wilkins, Philadelphia, Pa., 21$^{st}$ Edition (2005), describes compositions and formulations suitable for pharmaceutical delivery of one or more therapeutic compounds or molecules, such as one or more peptide conjugate, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a carrier. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Premembrane protein (prM): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Recombinant: A recombinant nucleic acid, protein, or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques such as those described in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (Gene, 73:237-44, 1988); Higgins and Sharp (CABIOS, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons. ALIGN compares entire sequences against one another, while LFASTA compares regions of local similarity. These alignment tools and their respective tutorials are available on the Internet. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266: 131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of a specific protein using ALIGN set to default parameters. Proteins with even greater similarity to a reference sequence will show increasing percentage identities when assessed by this method, such as at least 80%, at least 85%, at least 90%, at least 92%, at least 95%, at least 98%, or at least 99% sequence identity.

When significantly less than the entire sequence is being compared for sequence identity, homologous sequences will typically possess at least 80% sequence identity over short windows of 10-20, and may possess sequence identities of at least 85%, at least 90%, at least 95%, 96%, 97%, 98%, or at least 99%, depending on their similarity to the reference sequence. Sequence identity over such short windows can be determined using LFASTA. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope. The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Subject: Living multi-cellular vertebrate organisms, a category that includes both human and non-human mammals (such as mice, rats, sheep, horses, cows, and non-human primates).

Therapeutically effective amount: A quantity of a specified agent sufficient to achieve a desired effect in a subject being treated with that agent. For example, this may be the amount of a recombinant flavivirus useful for eliciting an immune response in a subject and/or for preventing infection by TBEV. Ideally, in the context of the present disclosure, a therapeutically effective amount of a recombinant flavivirus is an amount sufficient to increase resistance to, prevent, ameliorate, and/or treat infection caused by TBEV in a subject without causing a substantial cytotoxic effect in the subject. The effective amount of a recombinant flavivirus useful for increasing resistance to, preventing, ameliorating, and/or treating infection in a subject will be dependent on, for example, the subject being treated, the manner of administration of the therapeutic composition and other factors.

Tick-borne encephalitis virus (TBEV): A complex of related viruses that cause neurotropic disease. The TBEV complex includes Far Eastern, Siberian, and Central European TBEV subtypes, as well as Omsk hemorrhagic fever, Kyasanur forest disease, Langat, Louping ill, Negishi, and Powassan viruses. TBEV is transmitted through the bite of an infected ticks, mainly by *Ixodes ricinus, I. persculatus* ticks, or *Dermacentor* and *Hyalomma* species of ticks.

TBEV is endemic to many regions of the world (including Europe, Siberia, India, Japan, and North America); however the majority of cases occur in Russia. TBEV symptoms include a characteristic biphasic illness, with an initial phase of symptoms including fever, malaise, anorexia, muscle aches, headache, nausea and/or vomiting that lasts 2 to 4 days and corresponds to the viremic phase. After about 8 days of remission, the second phase of the disease occurs in 20 to 30% of patients and involves the central nervous system with symptoms of meningitis (e.g., fever, headache, and a stiff neck) or encephalitis (e.g., drowsiness, confusion, sensory disturbances, and/or motor abnormalities such as paralysis) or meningoencephalitis. In some patients infected with TBEV long-term or even permanent neurological sequelae occur.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or nucleic acids derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

III. TBEV/DEN4 Chimeric Viruses

Disclosed herein are chimeric TBEV/DEN4 flaviviruses including 5' and 3' non-coding regions, a C protein, and non-structural proteins from DEN4 virus, and a prM protein and E protein from TBEV. These chimeric viruses are designated TBEV/DEN4 chimeras. In particular examples, the chimeric TBEV/DEN4 virus includes a first nucleic acid molecule including a 5' non-coding region from a DEN4 virus, a nucleic acid encoding a C protein from DEN4 virus, non-structural proteins from a DEN4 virus, and a 3' non-coding region from a DEN4 virus, wherein nonstructural protein NS4B includes a phenylalanine at amino acid position 112, nonstructural protein NS5 includes an alanine at amino acid position 654 and an alanine at amino acid position 655, and the 3' non-coding region includes a deletion of nucleotides 10478-10507 (Δ30). The chimeric TBEV/DEN4 virus also includes a second nucleic acid molecule which is operably linked to the first nucleic acid molecule, the second nucleic acid molecule encoding a prM protein from a TBEV and an E protein from a TBEV, wherein the E protein includes an amino acid substitution that differs from the wild type TBEV at amino acid position 315 and a tryptophan at amino acid position 240.

In some embodiments, the disclosed chimeric TBEV/DEN4 viruses are utilized in a replication-defective virus system or pseudoinfectious virus system. In these systems, the TBEV/DEN4 chimera includes one or more alterations that make the virus incapable of replicating its genome or incapable of assembling and releasing progeny virus particles. In particular examples, the chimeric TBEV/DEN4 viruses disclosed herein are provided in two separate components. When both components infect the same cell, genome replication or production of infectious progeny does not occur; however infectious progeny are limited following subsequent infection because one component is missing from the viral genome. However, after subsequent infection, viral gene expression occurs, producing viral antigens that can elicit an immunogenic response in a subject. See, e.g., U.S. Pat. Publication Nos. 2009/0155301 and 2009/0324623; Widman et al., *Adv. Virus Res.* 72:77-126, 2008; Widman et al., *Vaccine* 26:2762-2771, 2008; Ishikawa et al., *Vaccine* 26:2772-2781, 2008; Suzuki et al., *J. Virol.* 83:1870-1880, 2009, each of which is incorporated by reference herein.

In some embodiments, the disclosed chimeric TBEV/DEN4 viruses are modified to delete at least a portion of the nucleic acid encoding at least one structural protein, for example, the C protein, the prM protein and/or the E protein. In some examples a portion or all of the nucleic acid encoding the DEN4 C protein is removed from the chimeric virus. In other examples, the nucleic acids encoding the TBEV prM protein and/or E protein are removed from the chimeric virus. In a further example, the nucleic acids encoding the DEN4 C protein and the TBEV prM and E proteins are removed from the chimeric virus. In one non-limiting example the TBEV/DEN4 flavivirus includes 5' and 3' non-coding regions and non-structural proteins from DEN4 virus, and a prM protein and E protein from TBEV. In particular examples, the chimeric TBEV/DEN4 virus includes a first nucleic acid molecule including a 5' non-coding region from a DEN4 virus, a nucleic acid encoding non-structural proteins from a DEN4 virus, and a 3' non-coding region from a DEN4 virus, wherein nonstructural protein NS4B includes a phenylalanine at amino acid position 112, nonstructural protein NS5 includes an alanine at amino acid position 654 and an alanine at amino acid position 655, and the 3' non-coding region includes a deletion of nucleotides 10478-10507 (430) and also includes a second nucleic acid molecule which is operably linked to the first nucleic acid molecule, the second nucleic acid molecule encoding a prM protein from a TBEV and an E protein from a TBEV, and wherein the E protein includes an amino acid substitution that differs from the wild type TBEV at amino acid position 315 and a tryptophan at amino acid position 240, wherein the chimeric virus does not encode a C protein. In one example, the chimeric TBEV/DEN4 flavivirus construct includes aspartic acid at amino acid 315 of the TBEV E protein. The nucleic acid encoding the at least one deleted structural protein is provided in a separate nucleic acid. For example a nucleic acid molecule including a nucleic acid encoding a DEN4 C protein, a TBEV prM protein and/or a TBEV E protein is provided in a separate construct.

In some examples disclosed herein, the TBEV prM and E protein-encoding nucleic acid is derived from a particular TBEV subtype, such as Far Eastern, Central European, or Siberian subtypes. In a particular example, the TBEV subtype includes Far Eastern subtype, Sofjin strain (e.g., GenBank Accession No. AB062064, incorporated by reference as present in GenBank on May 28, 2009). In other examples, the TBEV subtype includes European subtype, such as Hypr strain (e.g., GenBank Accession No. U39292) or Absettarov strain (e.g., GenBank Accession No. AF091005), both of which are incorporated by reference as in GenBank on May 28, 2009. In additional examples, the TBEV prM and/or E protein-encoding nucleic acid is derived from a member of the TBEV complex, such as Kyasanur forest disease, Langat, Louping ill, Negishi, Omsk hemorrhagic fever, or Powassan virus.

Nucleic acid and protein sequences for TBEV prM and E protein are publicly available. For example, GenBank Accession Nos.: NC_001672 (nucleotides 469-972) and X03870 (nucleotides 339-890) disclose TBEV prM nucleic acid sequences, and GenBank Accession Nos.: NP_775501, CAA27502, and X07755 (amino acids 466-963) disclose TBEV prM protein sequences, all of which are incorporated by reference as present in GenBank on May 28, 2009. In addition, GenBank Accession Nos.: NC_001672 (nucleotides 973-2460) and X03870 (nucleotides 891-2100) disclose TBEV E nucleic acid sequences, and GenBank Accession Nos.: NP_775503, CAA27504, and X07755 (amino acids 964-2457) disclose TBEV E protein sequences, all of which are incorporated by reference as present in GenBank on May 28, 2009. In certain examples, a TBEV prM and/or E sequence has at least 80% sequence identity, for example at least 85%, 90%, 95%, or 98% sequence identity to a publicly available TBEV prM and/or E sequence, such as those present in GenBank.

In further examples, the TBEV nucleic acid encoding the prM and/or E protein is at least 95%, at least 96%, at least 97%, at least 98%, or at least 99% identical to the prM or E protein-encoding nucleic acid sequence disclosed in SEQ ID NO: 1. In other examples, the TBEV prM and/or E proteins are at least 95%, at least 96%, at least 97%, at least 98%, or at least 99% identical to the prM or E protein amino acid sequence disclosed in SEQ ID NO: 2.

In some examples disclosed herein, the DEN4 5' non-coding region, C protein, non-structural proteins, and 3' non-coding region nucleic acid is derived from a particular DEN4 strain, such as wild type DEN4 1036 or attenuated DEN4 PDK-48. Additional DEN4 strains are known in the art (see e.g., U.S. Pat. Nos. 5,939,254 and 6,793,488). In a particular example, the DEN4 virus strain is DEN4 814669, Dominica 1981 (e.g., GenBank Accession Nos. AF375822 and AY376438, incorporated by reference as present in GenBank on May 28, 2009).

Nucleic acid and protein sequences for DEN4 viruses are publicly available. For example, GenBank Accession Nos.: NC_002640 and AF326825 disclose DEN4 genomic nucleic acid sequences, and GenBank Accession Nos.: NP_073286 and AAG45435 disclose DEN4 protein sequences, all of which are incorporated by reference as present in GenBank on May 28, 2009. In certain examples, a DEN4 5' non-coding region, C protein, non-structural proteins, and/or 3' non-coding region sequence has at least 80% sequence identity, for example at least 85%, 90%, 95%, or 98% sequence identity to a publicly available DEN4 sequences, such as those present in GenBank.

In further examples, the DEN4 5' non-coding region, C protein, non-structural proteins, and 3' non-coding region nucleic acid is at least 95%, at least 96%, at least 97%, at least 98%, or at least 99% identical to the 5' non-coding region, C protein, non-structural proteins, and 3' non-coding region nucleic acid sequence disclosed in SEQ ID NO: 1. In other examples, the DEN4 C protein and non-structural proteins are at least 95%, at least 96%, at least 97%, at least 98%, or at least 99% identical to the C protein and non-structural protein amino acid sequence disclosed in SEQ ID NO: 2.

In particular embodiments, the chimeric TBEV/DEN4 virus includes amino acid substitutions at least at amino acid positions 240 and 315 of the TBEV E protein. An arginine residue at amino acid position 240 of the TBEV E protein is replaced with tryptophan. A lysine residue at amino acid position 315 of the TBEV E protein is replaced with a different amino acid (e.g., aspartic acid, alanine, phenylalanine, leucine, serine, arginine, threonine, tryptophan, valine, or tyrosine). In one example, the TBEV E protein includes tryptophan at amino acid 240 and aspartic acid at amino acid 315. The disclosed TBEV/DEN4 chimera may optionally include an amino acid substitution at position 84 of the TBEV E protein (such as glycine, leucine, valine, arginine, serine, alanine, tryptophan, or phenylalanine). In a particular example, the TBEV E protein includes a glycine at amino acid position 84.

In particular embodiments, the chimeric TBEV/DEN4 virus also includes amino acid substitutions at least at amino acid position 112 of the DEN4 NS4B protein, amino acid position 654 of the DEN4 NS5 protein, and amino acid position 655 of the DEN4 NS5 protein. A leucine residue at amino acid 112 of the DEN4 NS4B protein is replaced with phenylalanine, an aspartic acid at amino acid position 654 of the DEN4 NS5 protein is replaced with alanine, and an arginine at amino acid position 655 of the DEN4 NS5 protein is replaced with an alanine. In addition, the TBEV/DEN4 chimera includes a deletion of 30 base pairs in the 3' NCR at position 10478-10507 of the wild-type virus. The disclosed TBEV/DEN4 chimera may optionally include an amino acid substitution at position 6 of the DEN4 NS1 protein (such as valine, cysteine, histidine, tryptophan, or tyrosine). In a particular example, the DEN4 NS1 protein includes a valine at amino acid position 6. The TBEV/DEN4 chimera may optionally include an amino acid substitution at position 642, 643, 878, 879, or combinations thereof, of the DEN4 NS5 protein. In particular examples, one or more of amino acid positions 642, 643, 878, and/or 879 of the DEN4 NS5 protein includes an alanine.

In a particular embodiment, a chimeric TBEV/DEN4 virus has the nucleic acid or amino acid sequence disclosed herein as SEQ ID NOs: 1 and 2, respectively. In some examples, the chimeric TBEV/DEN4 virus encodes a polypeptide at least 95% (such as at least 96%, 97%, 98%, or 99%) identical to SEQ ID NO: 2. In other examples, the chimeric TBEV/DEN4 virus encodes a polypeptide that comprises or consists of SEQ ID NO: 2. In further examples, the chimeric TBEV/DEN4 virus includes a nucleic acid molecule at least 95% (such as at least 96%, 97%, 98%, or 99%) identical to SEQ ID NO: 1. In other examples, the chimeric TBEV/DEN4 virus comprises or consists of SEQ ID NO: 1.

In one embodiment, a chimeric TBEV/DEN4 virus includes a nucleic acid encoding the virus that is represented by ATCC Accession number PTA-9968 (which is an E. coli strain BD1528 containing plasmid pBR322 including the chimeric TBEV/DEN4 genome TBE/DEN4Δ30/E-315D/NS5-654AA, provided to the ATCC on Apr. 17, 2009 and acknowledged as viable on May 28, 2009).

The disclosure also provides TBEV/DEN4 chimeras further including one or more nucleic acid or amino acid substitutions, such that the resulting chimera has improved characteristics. In some examples, the improved characteristic of the chimera with one or more substitutions includes, but is not limited to, decreased plaque size, temperature sensitivity, host range restriction, and increased stability in cell culture. In some examples, an improved characteristic includes reduced viral replication in neuronal cells. In additional examples, the improved characteristic of the chimera with one or more substitution includes decreased neurovirulence or neuroinvasiveness in a subject (such as mice or non-human primates).

Manipulation of the nucleic acid molecule of the disclosed TBEV/DEN4 chimeras (e.g. SEQ ID NO: 1) by standard procedures, including for instance site-directed mutagenesis or PCR and M13 primer mutagenesis, can be used to produce variants with improved characteristics (such as increased stability in cell culture, decreased neurovirulence or decreased neuroinvasiveness). Chemical mutagenesis may also be used to produce variants. Details of these techniques are well known. For instances, protocols are provided in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989. The simplest modifications involve the substitution of one or more amino acids for amino acids having similar physiochemical and/or structural properties. These so-called conservative substitutions are likely to have minimal impact on the activity and/or structure of the resultant protein. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

In addition to targeted mutagenesis to produce variants of the disclosed TBEV/DEN4 chimeras, naturally occurring variants may accrue upon passage in cell culture that result in variants, some with desirable characteristics. Nucleic acid and amino acid substitutions that accrue in chimeric viruses during cell culture passages are readily determined by sequence analysis of the virus amplified from isolated plaques of the virus seed, and can be engineered into infectious clones to generate TBEV/DEN4 chimera variants that have improved characteristics (such as decreased neurovirulence or neuroinvasiveness). Consistent variants identified from multiple seeds or isolated plaques indicate the desired substitutions of the chimera in the cell type.

In some embodiments, the TBEV/DEN4 chimera encodes a polypeptide that includes one or more amino acid substitutions of one or more residues of the TBEV prM or E protein, such that the chimera has improved characteristics. In other examples, the chimeric flavivirus encodes a polypeptide that includes one or more amino acid substitutions of one or more residues of the DEN4 non-structural proteins and/or C protein, such that the resulting chimera has improved characteristics. In additional examples, the chimeric flavivirus includes one or more nucleic acid substitutions in the DEN4 5' and/or 3' non-coding region, such that the chimera has improved characteristics.

The disclosed TBEV/DEN4 chimeras are produced by replication in host cells in culture. Methods of producing viruses are well known in the art (see e.g. *Fields Virology*, Knipe and Howley, eds., Lippincott, Williams, and Wilkins, 2001; Flint et al., *Principles of Virology*, ASM Press, 2000). Host cell lines should be easy to infect with virus or transfect with viral genomic RNA, be capable of stably maintaining foreign RNA with an unarranged sequence, and have the necessary cellular components for efficient transcription, translation, post-translation modification, virus assembly, and secretion of the protein or virus particle. Preferably, cells are those having simple media component requirements which can be adapted for growth in suspension culture. In some examples, the host cell line is a mammalian cell line that can be adapted to growth in low serum or serum-free medium. Suitable host cell lines include Vero (monkey), SH-SY5Y cells (human), and LN-18 cells (human), and C6/36 cells (mosquito). Suitable cell lines can be obtained from the American Type Culture Collection (ATCC), Manassas, Va.

The neurovirulence and neuroinvasiveness of the disclosed TBEV/DEN4 chimeric viruses can be assessed by methods well known to one of skill in the art. For example, neurovirulence may be assessed in animal models (such as mice or non-human primates) by ic inoculation with serial dilutions of virus and monitoring for morbidity and mortality. The ic 50% lethal dose (icLD$_{50}$) can be determined as a measure of neurovirulence. Neuroinvasiveness may be assessed by ip inoculation of individuals with virus and determining the ipLD$_{50}$ by monitoring animals for morbidity (such as neuroinflammation) and mortality, and measuring the presence of virus in the central nervous system at various time points post-inoculation.

IV. Methods of Eliciting an Immune Response

Provided herein are methods of eliciting an immune response in a subject by administering one or more of the disclosed nucleic acid chimeras, or a recombinant flavivirus comprising a nucleic acid chimera described herein, to the subject. In a particular example, the subject is a human. The recombinant flavivirus comprising a nucleic acid chimera disclosed herein can be used to produce an immune response that prevents infection with TBEV (such as Far Eastern, Central European, or Siberian TBEV subtypes), and can also be used to treat or inhibit infection with TBEV.

The E protein of members of the tick-borne encephalitis virus complex share significant sequence identity (approximately 85% or more). Thus, the TBEV/DEN4 chimeric viruses disclosed herein may also be used to produce an immune response that prevents or treats or inhibits infection with other members of the tick-borne encephalitis virus complex, including, but not limited to Omsk hemorrhagic fever, Kyasanur forest disease, Langat, Louping ill, Negishi, and Powassan viruses.

In some examples, the method further includes selecting a subject in need of enhanced immunity to TBEV (such as Far Eastern, Central European, or Siberian TBEV subtypes). Subjects in need of enhanced immunity to TBEV include subjects who are at risk of TBEV infection, subjects who have been exposed to one or more TBEV, and subjects who are infected with TBEV. Residents of, or travelers to, countries or regions where TBEV is endemic are at risk of contracting TBEV, such as TBEV caused by infection with Far Eastern, Central European, or Siberian TBEV subtypes. Additional factors that contribute to risk of infection with TBEV include the characteristics of the area, presence of TBEV in the area, exposure to ticks, and lack of preventive measures (such as insect repellant). The risk of TBEV is generally higher in rural areas and among those with recreational or occupational exposure to outdoor settings (such as farm or forest workers, hunters, and campers).

A relatively recent development in the field of immune stimulatory compounds (for example, vaccines) is the direct injection of nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid encoding a virus polypeptide comprising at least one virus epitope may be utilized in such DNA vaccination methods.

One approach to administration of nucleic acids is direct immunization with vector DNA. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, which are negatively charged cage-like structures of 30-40 nm in size formed spontaneously on mixing cholesterol and saponin (see, e.g., Sjolander et al., *J. Leukoc. Biol.* 64:713-723, 1998). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

The disclosed nucleic acid chimeras or recombinant flaviviruses comprising the nucleic acid chimeras can be administered to a subject by any of the routes normally used for introducing a composition into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Administration can be accomplished by single or multiple doses. The dose administered to a subject in the context of the present disclosure should be sufficient to induce a beneficial therapeutic response in a subject over time, or to inhibit or prevent infection. The dose required will vary from subject to subject depending on the species, age, weight and general condition of the subject, the particular immunogenic composition being used, and its mode of administration. An appropriate dose can be determined by one of ordinary skill in the art using only routine experimentation. In some examples, the dose administered to the subject is about 1 μg to about 1000 μg (such as about 1 μg to about 500 μg, about 10 μg to about 500 μg, or about 50 μg to about 500 μg) of the disclosed chimeric viruses. In other examples, the dose administered to the subject is about 10 pfu to about $10^5$ pfu (such as about 10 pfu to about $10^4$ pfu, about $10^2$ pfu to about $10^4$ pfu, or about $10^3$ pfu to about $10^5$ pfu). Repeated immunizations may be necessary to produce an immune response in a subject. Immunization protocols (such as amount of immunogen, number of doses and timing of administration) can be determined experimentally, for example by using animal models (such as mice or non-human primates), followed by clinical testing in humans.

In some examples, the disclosed TBEV/DEN4 chimeric nucleic acid or virus is administered to a subject as a two-component genome or as a pseudoinfectious virus. See, e.g., U.S. Pat. Publication Nos. 2009/0155301 and 2009/0324623; Widman et al., *Adv. Virus Res.* 72:77-126, 2008; Widman et al., *Vaccine* 26:2762-2771, 2008; Ishikawa et al., *Vaccine* 26:2772-2781, 2008; Suzuki et al., *J. Virol.* 83:1870-1880, 2009, each of which is incorporated by reference herein.

In one example, the method includes administering a therapeutically effective amount of a pseudoinfectious TBEV/DEN4 chimeric virus to a subject. The pseudoinfectious TBEV/DEN4 can be produced by transfecting cells with a disclosed chimeric TBEV/DEN4 virus modified to delete at least a portion of the nucleic acid encoding at least one structural protein (for example, the C protein, prM protein and/or E protein), and also transfecting the same cells with a second viral genome capable of producing the deleted structural proteins (such as the C protein, prM protein and/or E protein). The resulting infectious particles can be administered to a subject to elicit an immune response to expressed viral proteins, such as the prM and E proteins.

In another example, the method includes administering a therapeutically effective amount of a two-component TBEV/DEN4 genome including a TBEV/DEN4 viral genome including a disclosed chimeric TBEV/DEN4 virus with deletion of the C protein, prM protein and/or E protein, and a complementing genome that includes a nucleic acid encoding the deleted structural protein (such as a DEN4 C protein, TBEV prM protein and/or TBEV E protein).

In additional examples, the disclosed nucleic acid chimeras, recombinant flaviviruses comprising the nucleic acid chimeras, or immunogenic compositions can be administered to a subject prior to, concurrent with or subsequent to one or more additional immunogenic compositions, such as one or more vaccines for TBEV, other flaviviruses (such as Dengue viruses, St. Louis encephalitis virus, Japanese encephalitis virus, West Nile virus, or yellow fever virus), or other pathogens. In a particular example, the additional immunogenic composition includes a Langat virus/DEN4 chimera (see, e.g., Pletnev et al., *J. Virol.* 75:8259-8267, 2001). In another particular example, the additional immunogenic composition includes a West Nile virus/DEN4 chimera (see, e.g., Pletnev et al., *Proc. Natl. Acad. Sci. USA* 99:3036-3041, 2002).

Provided herein are pharmaceutical compositions (also referred to as immunogenic compositions) which include a therapeutically effective amount of the disclosed recombinant TBEV/DEN4 viruses alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The immunogenic compositions disclosed herein can additionally employ adjuvants conventionally found in pharmaceutical compositions in their art-established fashion and at their art-established levels. Thus, for example, the compositions can contain materials useful in physically formulating various dosage forms of the preferred embodiments. Adjuvants are commonly combined with vaccines for the purpose of improving immune response. Suitable adjuvants include aluminum hydroxide, aluminum phosphate, aluminum oxide, monophosphenyl lipid A, muramyl dipeptide, glucans, Quil A, Freund's incomplete adjuvant, or Freund's complete adjuvant.

V. Methods of Assessing Immunogenic Response

The compositions and methods disclosed herein are useful for generating an immunogenic (immunological) response in a host or subject. Methods of assessing an immune response to a composition are well known to one of skill in the art.

In some examples, an immune response to a recombinant TBEV/DEN4 chimeric virus, such as one of the disclosed chimeras, is determined by assessing the production of antibodies to the specific viral proteins included in the chimeric virus (such as TBEV prM and E proteins). The method of detecting antibodies to the disclosed recombinant TBEV/DEN4 chimeric viruses in a sample can be performed, for example, by a plaque reduction neutralization test. In some examples, TBEV/DEN4 virus is incubated with serial dilutions of fluid sample specimens. The neutralizing antibody titer is identified as the highest serum dilution that reduces the number of virus plaques in the test by 60% or greater. A fluid sample of this method can comprise any biological fluid which could contain the antibody, such as cerebrospinal fluid, blood, bile plasma, serum, saliva, and urine. Other possible examples of body fluids include sputum, mucus and the like. The durability of the neutralizing antibody response can be assessed by determining neutralizing antibody titer at various time points post-inoculation (such as about one month, two months, three months, six months, nine months, twelve months, or more post-inoculation).

Enzyme immunoassays such as IFA, ELISA and immunoblotting can be readily adapted to accomplish the detection of antibodies according to the methods of this disclosure. An ELISA method effective for the detection of the antibodies can, for example, be as follows: 1) bind a polypeptide (such as TBEV prM or E protein) to a substrate; 2) contact the bound polypeptide with a fluid or tissue sample containing the antibody; 3) contact the above with a secondary antibody bound to a detectable moiety which is reactive with the bound antibody (for example, horseradish peroxidase enzyme or alkaline phosphatase enzyme); 4) contact the above with the substrate for the enzyme; 5) contact the above with a color reagent; and 6) observe/measure color change or development.

Another immunologic technique that can be useful in the detection of antibodies uses monoclonal antibodies (mAbs) for detection of antibodies specifically reactive with the disclosed TBEV/DEN4 chimera (such as TBEV prM or E protein) in a competitive inhibition assay. Briefly, a sample is contacted with a polypeptide which is bound to a substrate (for example, a 96-well plate). Excess sample is thoroughly washed away. A labeled (for example, enzyme-linked, fluorescent, radioactive, etc.) mAb is then contacted with any previously formed polypeptide-antibody complexes and the amount of mAb binding is measured. The amount of inhibition of mAb binding is measured relative to a control (no antibody), allowing for detection and measurement of antibody in the sample.

As a further example, a micro-agglutination test can be used to detect the presence of antibodies to the disclosed TBEV/DEN4 chimeras in a sample. Briefly, latex beads, red blood cells or other agglutinable particles are coated with a polypeptide of the TBEV/DEN4 chimera (such as TBEV prM or E protein) and mixed with a sample, such that antibodies in the sample which are specifically reactive with the antigen crosslink with the antigen, causing agglutination. The agglutinated polypeptide-antibody complexes form a precipitate, visible with the naked eye or measurable by spectrophotometer.

In yet another example, a microsphere-based immunoassay can be used to detect the presence of antibodies in a sample. Briefly, microsphere beads are coated with a component of the disclosed TBEV/DEN4 chimeras (such as TBEV prM or E protein) and mixed with a sample, such that antibodies in the sample which are specifically reactive with the antigen bind the antigen. The bead-bound polypeptide-antibody complexes are allowed to react with fluorescent-dye labeled anti-species antibody (such as FITC-labeled goat anti-human IgM), and are measured using a microsphere reader (such as a Luminex instrument).

In additional examples, an immune response to a TBEV/DEN4 chimera (such as TBEV prM or E protein) is determined by assessing the protective effect against infection produced by immunization with the disclosed TBEV/DEN4 chimeras. Briefly, a host (such as a mouse or a non-human primate, for example rhesus monkey) is immunized with one or more of the disclosed TBEV/DEN4 chimeric viruses. Following a sufficient period of time to allow development of an immune response, the host is challenged with TBEV or unmodified TBEV/DEN4 chimera. The infection is monitored by examination of blood samples for the presence of virus in the blood. A reduction in the viral titer in immunized hosts as compared to control hosts and/or an increase in TBEV-specific neutralizing antibody titers indicates that an immune response developed to the composition. Protective immunity is assessed by absence of viremia, absence of clinical symptoms of infection, and measurement of host anamnestic response following challenge with TBEV or unmodified TBEV/DEN4 chimera.

The efficacy of the disclosed TBEV/DEN4 chimeras to protect against infection with other members of the TBEV complex (such as Omsk hemorrhagic fever, Kyasanur forest disease, Langat, Louping ill, Negishi, and Powassan virus) can be similarly assessed, except the challenge is with the appropriate TBEV complex virus, rather than TBEV or unmodified TBEV/DEN4 virus.

The present disclosure is illustrated by the following non-limiting Examples.

EXAMPLES

Example 1

Construction of TBEV/DEN4 Chimeras and Characterization in Cell Culture

This example describes the construction of TBEV/DEN4 nucleic acid chimeras and their in vitro characterization.

Methods

Cell Culture and Viruses. Simian Vero cells (World Health Organization seed, passages 143-149) were maintained in Opti-Pro Serum Free Medium (Invitrogen, Carlsbad, Calif.), supplemented with 4 mM L-glutamine (Invitrogen). Human neuroblastoma SH-SY5Y cells (American Type Culture Collection, Manassas, Va.) were maintained in 1:1 Minimal Essential and F12 media (Invitrogen), supplemented with 10% heat-inactivated fetal bovine serum (FBS; BioWhittaker, Basel, Switzerland). Human glioblastoma LN-18 cells (American Type Culture Collection, Manassas, Va.) were maintained in Dulbecco's Modified Eagle Medium (DMEM) (Invitrogen), supplemented with 5% heat-inactivated FBS, 4 mM L-glutamine, and 1.5 g/L sodium bicarbonate (Invitrogen).

Construction of Full-Length cDNA Clones and Recovery of Chimeric Viruses. Chimeric TBEV/DEN4 virus contained the prM and E protein genes of TBEV Far-Eastern subtype strain Sofjin and the remaining sequence derived from recombinant DEN4 virus. Chimeric TBEV/DEN4Δ30 virus also contained a 30 nucleotide deletion (nucleotides 10478-10507) within the 3' non-coding region of the DEN4 genome. Construction of both viruses has been described previously (Pletnev et al., *Proc. Natl. Acad. Sci. USA* 89:10532-10536, 1992; Rumyantsev et al., *Vaccine* 24:133-143, 2006). The full-length infectious cDNA clones TBEV/DEN4 and TBEV/DEN4Δ30 (GenBank Accession Nos. FJ828986 and FJ828987, respectively; incorporated herein by reference on May 28, 2009) were used in these studies to generate recombinant viruses containing amino acid substitutions of aspartic acid at amino acid position 315 of the TBEV E protein (E-$K_{315}D$) and alanine at amino acid positions 654 and 655 of the DEN4 NS5 protein (NS5-$DR_{654,655}AA$). Each amino acid substitution was introduced singly or in combination by site-directed mutagenesis.

DNA fragments encompassing either DEN4 or TBEV specific sequences were sub-cloned into the pUC18 vector and each amino acid substitution was introduced through site-directed mutagenesis of the plasmid, as previously described (Rumyantsev et al., *J. Virol.* 80:1427-1439, 2006; Hanley et al., *J. Virol.* 76:525-531, 2002). Mutagenic primers introducing Asp (codon GAC) at amino acid residue 315 (nucleotides 1893 and 1895) of the TBEV E protein in pUC-TBEV and Ala/Ala (codons GCA & GCG) at amino acid residues 654 and 655 (nucleotides 9538, 9539, 9540, 9541) of the DEN4 NS5 protein in pUC-DEN4c were used to engineer these mutations. The pUC18-TBEV fragment contained unique NheI and XhoI restriction sites that corresponded to TBEV/DEN4 nucleotides 240-2361, while the pUC-DEN4c fragment contained unique SacII and MluI sites that corresponded to TBEV/DEN4 nucleotides 9334-10418. Fragments containing the desired mutations were excised from pUC-TBEV or pUC-DEN4c by restriction digestion and introduced into the TBEV/DEN4 or TBEV/DEN4Δ30 infectious clones containing an SP6 promoter (Lai et al., *Proc. Natl. Acad. Sci. USA* 88:5139-5143, 1991; Pletnev et al., *Proc. Natl. Acad. Sci. USA* 89:10532-10536, 1992; Rumyantsev et al., *Vaccine* 24:133-143, 2006).

Full-length infectious chimeric RNA derived from the modified TBEV/DEN4 or TBEV/DEN4Δ30 DNA plasmids were generated by transcription with SP6 polymerase (Epi-Centre Biotechnologies, Madison, Wis.) and transfected into Vero cells using Lipofectamine™ (Invitrogen, Carlsbad, Calif.), according to the manufacturer's protocol. Since mutations at these positions previously resulted in temperature sensitivity in either LGTV or DEN4V, all viruses were grown at 32° C. The rescued TBEV/DEN4 and TBEV/DEN4Δ30 mutant viruses were biologically cloned by two terminal dilutions and then amplified by two passages in Vero cells before experimental stocks were obtained. Titers for all viruses obtained were between 6.4 and 7.2 $\log_{10}$ pfu/ml.

Titration of Chimeric Viruses. Confluent monolayers of Vero cells in 24-well plates were infected with 10-fold serial dilutions of virus, incubated at 37° C. for one hour, and then overlaid with 1 ml of Opti-MEM I containing 1% methylcellulose (Invitrogen), 2% heat-inactivated FBS, 4 mM L-glutamine, and 0.05 mg/ml of gentamicin. After incubation for 6 days at 32° C., the cells were fixed in 100% methanol for 20 minutes, and plaques were visualized by immunostaining with TBEV-specific hyperimmune mouse ascitic fluid (ATCC, Catalog No. VR-1264 AF) and peroxidase-labeled polymer conjugated to anti-mouse immunoglobulin (Dako Co., Carpinteria, Calif.)

Sequencing of cDNA Clones and Chimeric Viruses. Viral RNA was extracted from virus suspension using the QiaAmp® Viral RNA mini kit (Qiagen, Valencia, Calif.) according to the manufacturer's protocol. One-step RT-PCR was performed on the viral RNA using Superscript® One-Step kit (Invitrogen), and primers specific for the DEN4 virus or TBEV genome (Table 2). The nucleotide consensus sequences were determined through direct sequence analysis of the PCR fragments on a 3730 Genetic Analyzer using TBEV- or DEN4-specific primers in a BigDye® cycle sequencing reaction (Applied Biosystems, Foster City, Calif.) and were analyzed using Sequencher® 4.7 software (Gene Codes Corporation, Ann Arbor, Mich.) as described previously (Rumyantsev et al., *Vaccine* 24:133-143, 2006).

TABLE 2

Primers used to derive cDNA amplicons

| Primer name | Primer sequence | Nucleotide position in TBEV/DEN4 genome (SEQ ID NO: 1) |
|---|---|---|
| 5'DEN4 | AGTTGTTAGTCTGTGTGGACCGACA (SEQ ID NO: 3) | 1-24 |
| 2546R | TCTCGCTGGGGACTCTGGTTGAAAT (SEQ ID NO: 4) | 2536-2560 |
| 2420F | AGCAGACATGGGTTGTGTGGCGTC (SEQ ID NO: 5) | 2434-2457 |
| 4588R | ACTCCTTCAGACAGTGCGGCTTTT (SEQ ID NO: 6) | 4579-4602 |
| 4420F | CCCTTTTGGTGAAACTGGCACTGA (SEQ ID NO: 7) | 4434-4457 |
| 6776R | TTGATTGTCTTGTGGGGTCCTTTG (SEQ ID NO: 8) | 6767-6790 |
| 6497F | CTATCAACACGCCCTGAACGAACT (SEQ ID NO: 9) | 6511-6534 |
| 8989R | TACCAGATTGCTCGGCTTCCCTTG (SEQ ID NO: 10) | 8980-9003 |
| 8520F | ATGGTGAACGGGGTGGTAAAACTG (SEQ ID NO: 11) | 8534-8557 |
| 10610R | GCTCTGTGCCTGGATTGATGTTG (SEQ ID NO: 12) | 10571-10593 |

In Vitro Characterization of Mutant Viruses in Cell Culture. All mutant viruses were evaluated in a comparative study for temperature sensitivity (ts), host range restriction (hs) and small plaque (sp) phenotypes by assessing virus titers at 32° C., 35° C., 37° C., and 39° C. in simian kidney Vero, human neuroblastoma SHSY-5Y, or human glioblastoma LN-18 cells. The efficiency of plaque (EOP) formation was determined by infecting confluent monolayers of Vero, LN-18, or SHSY-5Y cells with 10-fold serially diluted virus for 1 hr at 37° C., after which Opti-MEM I overlay containing methylcellulose, FBS, and gentamicin was added to each well. Cells were incubated for 6 days at the indicated temperature and plaques were visualized by immunostaining, as described above. Mutant viruses that exhibited 100-fold or greater reduction in titer at a given temperature relative to its titer at 32° C. were considered to be ts, while viruses that demonstrated 100-fold or greater reduction of titer in neuronal cells at 32° C. compared to that in Vero cells were designated as having a hr phenotype. Mutant viruses with mean plaque diameters that were ≤50% of the size of the parental TBEV/DEN4 or TBEV/DEN4Δ30 virus on the given cell line were designated as being sp. The EOP assays were undertaken on three separate occasions and the mean data point for each sample was measured.

Results

Derivation of Attenuated TBE/DEN4 and TBEV/DEN4Δ30 Chimeric Viruses. Full-length chimeric viruses containing the structural prM and E protein genes of the TBEV Far Eastern strain Sofjin and the remaining protein genes and NCRs of DEN4 virus, with or without the Δ30 mutation in the 3' NCR were derived as previously described (Pletnev et al., *Proc. Natl. Acad. Sci. USA* 89:10532-10536, 1992; Pletnev et al., *J. Virol.* 67:4956-4963, 1993; Rumyantsev et al., *Vaccine* 24:133-143, 2006). Additional substitutions within the E glycoprotein and NS5 protein genes (E-K$_{315}$D and NS5-DR$_{654,655}$AA) were introduced, singly or in combination, into either the TBEV/DEN4 or TBEV/DEN4Δ30 infectious cDNA clones. Chimeric viruses containing these substitutions were generated and recovered from Vero cells. All terminally diluted viruses were sequenced throughout the structural and NS5-3' NCR regions following expansion in Vero cells and were found to contain the desired mutations. All viruses maintained at least 6.0 log$_{10}$ pfu/ml titers at 32° C. in Vero cells (FIG. 1).

Full-length virus was also sequenced following expansion in Vero cells and found to include amino acid substitutions at position 240 of the TBEV E protein (E-R240W) and at position 112 of the DEN4 NS4B protein (NS4B-L112F). The nucleotide and amino acid sequence of the full-length TBEV/DEN4Δ30/E-K$_{315}$D/NS5-DR$_{654,655}$AA chimera, including the mutations arising in Vero cells is included herein as SEQ ID NOs: 1 and 2, respectively.

In Vitro Characterization of Chimeric Viruses. Host range restriction (hr) and temperature sensitivities (ts) of all chimeric TBEV/DEN4 or TBEV/DEN4Δ30 viruses were measured by infecting Vero or human neuronal cells (SH-SY5Y cells and LN-18 cells) at various temperatures and investigating viral titers and plaque morphology. All mutant viruses utilizing the unmodified TBEV/DEN4 backbone replicated well in all cell lines and at all temperatures, with the exception of TBEV/DEN4/E-K$_{315}$D/NS5-DR$_{654,655}$AA. This virus was ts in Vero, LN-18, and SHSY-5Y cells at 37° C. and 39° C., and replicated approximately 320-fold to 125,000-fold less at these temperatures than at 32° C.

TBEV/DEN4Δ30 virus was not hr or ts, as it replicated well up to 39° C. in all three cell lines investigated (FIG. 1). All viruses with the TBEV/DEN4Δ30 backbone demonstrated similar replication phenotypes whether they were grown in Vero or SH-SY5Y cells (FIG. 1). TBEV/DEN4Δ30 and TBEV/DEN4Δ30/E-K$_{315}$D viruses demonstrated stable replication phenotypes in both cell lines and replicated well up to 39° C. (≥5.7 log$_{10}$ pfu/ml), while TBEV/DEN4Δ30/NS5-DR$_{654,655}$AA demonstrated a 40,000-fold reduction in replication up to 39° C. in either cell line (FIG. 1). The triple mutant virus, TBEV/DEN4Δ30/E-K$_{315}$D/NS5-DR$_{654,655}$AA, was the most attenuated and demonstrated a 400,000-fold reduction in replication at 39° C. At 35° C., all viruses still replicated well in these cell lines; however, TBEV/DEN4Δ30/E-K$_{315}$D/NS5-DR$_{654,655}$AA replicated less well at 37° C. compared to the other three viruses in both cell lines, and was ts at the higher temperatures (FIG. 1).

While all viruses replicated well (between 6.4 and 7.8 $\log_{10}$ pfu/ml) at 32° C. in Vero and SH-SY5Y cells, only TBEV/DEN4Δ30 and TBEV/DEN4Δ30/NS5-DR$_{654,655}$AA viruses replicated to similar titers in human glioblastoma LN-18 cells at 32° C. (FIG. 1). TBEV/DEN4Δ30/E-K$_{315}$D virus demonstrated a borderline hr phenotype in LN-18 cells compared to Vero cells at 32° C.; however, it was not ts up to 39° C. in any of the cell lines. TBEV/DEN4Δ30/NS5-DR$_{654,655}$AA virus was not hr, although it was ts in LN-18 cells at 37° C. and 39° C., as shown by a 320-fold to 160,000-fold reduction in replication at these temperatures (FIG. 1). The triple mutant virus, (TBEV/DEN4Δ30/E-K$_{315}$D/NS5-DR$_{654,655}$AA) was both ts and hr, as it demonstrated 100-fold to >400,000-fold reduction in titer at 37° C. and 39° C. compared to the permissive temperature in all three cell lines measured and approximately a 400-fold reduction of titer in LN-18 cells compared to its titer in Vero cells at the same temperature (4.0 $\log_{10}$ vs. 6.6 $\log_{10}$ pfu) (FIG. 1). Furthermore, the triple mutant virus always exhibited 50-75% smaller-sized plaques compared to the TBEV/DEN4Δ30 parental virus, regardless of which cell line or temperature was analyzed (Table 3). Therefore, while E-K$_{315}$D and NS5-DR$_{654,655}$AA mutations exerted various attenuating effects on the property of the virus, the hr, ts, and small plaque phenotypes of TBEV/DEN4Δ30/E-K$_{315}$D/NS5-DR$_{654,655}$AA virus indicated that it was more attenuated in vitro compared to its parental or individually mutated viruses.

Example 2

Neurovirulence and Neuroinvasiveness of Chimeric Viruses in Mice

This example describes the characterization of the neurovirulence and neuroinvasiveness of the TBEV/DEN4 chimeras in mice.

Methods

To determine the neurovirulence of the TBEV/DEN4 chimeric viruses, litters of approximately ten 3 day-old Swiss mice (Taconic Farms, Hudson, N.Y.) were inoculated with 10-fold serial dilutions of virus via the intracerebral (ic) route and monitored for morbidity and mortality up to 21 days post-inoculation (dpi). Moribund mice were euthanized by $CO_2$. The ic 50% lethal dose (icLD$_{50}$) was determined by the method of Reed and Muench (*Am. J. Hyg.* 27:493-497, 1938).

Further studies were undertaken in litters of 3 day-old or 5 day-old suckling Swiss mice to investigate the replication of the chimeric viruses in mouse brain. The mice were ic inoculated with $10^3$ pfu of virus and at least three mouse brains per group were harvested on odd dpi, up to 21 dpi. Mouse brains were individually homogenized as a 10% solution (w/v) using homogenization buffer (1× Hank's Balanced Salt Solution (Invitrogen), 40 mg/ml ciprofloxacin (Bayer), 150 mg/ml clindamycin (Pharmacia & Upjohn), 250 µg/ml amphotericin B (Quality Biologicals)), as previously described (Blaney et

TABLE 3

Efficiency of plaquing of TBEV/DEN4Δ30 Chimeras

| | 32° C. | | 35° C. | | 37° C. | | 39° C. | |
|---|---|---|---|---|---|---|---|---|
| | Titer[a] | Plaque size[b] | Titer | Plaque size | Titer | Plaque size | Titer | Plaque size |
| Vero Cells | | | | | | | | |
| TBEV/DENΔ30 | 7.8 | 1.0 | 7.5 | 1.0 | 7.1 | 1.0 | 6.0 | 0.5 |
| TBEV/DENΔ30/E-K$_{315}$D | 6.7 | 0.5 | 6.7 | 0.5 | 6.3 | 0.5 | 5.7 | 0.5 |
| TBEV/DENΔ30/NS5-DR$_{654,655}$AA | 7.4 | 0.5 | 6.9 | 0.3 | 4.0 | ~0.2 | 2.8 | ~0.2 |
| TBEV/DENΔ30/E-K$_{315}$D/NS5-DR$_{654,655}$AA | 6.6 | ~0.3 | 5.8 | ~0.2 | 3.0 | <0.2 | <1.0 | ND |
| LN18 Cells | | | | | | | | |
| TBEV/DENΔ30 | 6.9 | ~0.3 | 6.7 | 1.0 | 6.3 | 1.0 | 5.0 | ~0.2 |
| TBEV/DENΔ30/E-K$_{315}$D | 4.8 | ~0.2 | 5.3 | 0.5 | 4.9 | 0.5 | 3.0 | <0.2 |
| TBEV/DENΔ30/NS5-DR$_{654,655}$AA | 6.5 | <0.2 | 6.1 | ~0.3 | 4.0 | <0.2 | 1.3 | <0.2 |
| TBEV/DENΔ30/E-K$_{315}$D/NS5-DR$_{654,655}$AA | 4.0 | <0.1 | 3.0 | <0.1 | 2.0 | <0.1 | <1.0 | ND |
| SH-SY5Y Cells | | | | | | | | |
| TBEV/DENΔ30 | 7.8 | 2.0 | 7.9 | 3.0 | 7.3 | 3.0 | 6.5 | 1.0 |
| TBEV/DENΔ30/E-K$_{315}$D | 6.8 | 1.5 | 6.5 | 2.0 | 6.4 | 3.0 | 5.8 | 2.0 |
| TBEV/DENΔ30/NS5-DR$_{654,655}$AA | 7.2 | 1.5 | 6.7 | 2.0 | 6.7 | 1.0 | 2.6 | 1.0 |
| TBEV/DENΔ30/E-K$_{315}$D/NS5-DR$_{654,655}$AA | 6.4 | 1.0 | 6.0 | 1.0 | 3.7 | ~0.3 | <1.0 | ND |

[a]Titer is calculated as $\log_{10}$ pfu/ml
[b]Plaque size calculated in mm
ND, not determined.
Bold font indicates 100-fold or greater reduction in viral replication compared to the permissive temperature (32° C.) in that particular cell line.

al., Vaccine, 26:4150-4159, 2008). Clarified viral supernatants were titrated for viral loads in Vero cells. To investigate the stability of the engineered mutations within the chimeric viruses after their replication in brain, virus RNA was extracted from brain homogenates obtained on the last days they were positive for virus and consensus sequences of the genomic regions encompassing the engineered mutations from each group were directly determined.

To investigate virus-induced pathology of the viruses in brains, 3-week-old female C57BL/6 mice (Taconic Farms) in groups of three were inoculated ic with $10^4$ pfu of either TBEV/DEN4, TBEV/DEN4Δ30, or TBEV/DEN4Δ30/E-$K_{315}$D/NS5-$DR_{654,655}$AA, whereas three control mice were mock-inoculated with Leibovitz's L-15 medium (Invitrogen). All mice were observed daily and euthanized on day 6, when TBEV/DEN4-infected mice developed paralysis. Mice were euthanized and perfused transcardially with PBS, and each mouse brain was dissected sagitally. The left hemisphere was frozen and stored at −80° C. for virus quantitation. The right hemisphere was fixed in 4% paraformaldehyde for 72 hours and processed according to standard histological methods. Twenty-five sections (30 μm thick) from each hemisphere were stained with hematoxylin and eosin (H&E), and analyzed for the presence and severity of virus-induced histopathology.

The neuroinvasive phenotype of the chimeric viruses was investigated in 3-week old SCID (ICRSC-M) mice (Taconic Farms, Hudson, N.Y.). To measure neuroinvasiveness, 10 mice were inoculated ip with $10^5$ pfu of TBEV/DEN4 virus, while separate groups of 33 to 56 mice were inoculated ip with $10^5$ pfu of TBEV/DEN4Δ30 virus or its derivatives. Mice were observed for 49 days for signs of morbidity typical of CNS involvement, including paralysis. Moribund mice were humanely euthanized upon signs neurologic disease. Kaplan-Meier survival curves followed by Tukey post-hoc tests were performed for statistical analysis (p<0.05) (Graph-Pad Prism 5 software, La Jolla, Calif.). Separately, groups of 35 SCID mice were inoculated ip with $10^5$ pfu of TBEV/DEN4 or TBEV/DEN4Δ30 virus, and the brains of three mice per group were harvested on odd days, for 21 days, to assess the level of virus replication. In addition, SCID mice in groups of 12 were inoculated ip with $10^5$ pfu of TBEV/DEN4Δ30-derived mutant viruses. The brains of three mice from each of these groups were harvested on days 13, 15, 17, and 19 to assess the level of virus replication as described above.

Results

Intracerebral $LD_{50}$ ($icLD_{50}$) values of TBEV/DEN4 or TBEV/DEN4Δ30 mutant viruses were measured in 3-day old Swiss mice to assess neurovirulence attenuation phenotypes of the mutant chimeric viruses in vivo. Introduction of the Δ30 deletion into the TBEV/DEN4 backbone did not alter the ability of the virus to infect the CNS, as $icLD_{50}$ values and average survival times (ASTs) were no different between TBEV/DEN4 and TBEV/DEN4Δ30 viruses in 3 day-old mice (Table 4). However, mutation of the E-$K_{315}$D or NS5-$DR_{654,655}$AA residues within the viral backbone alone decreased the overall mouse neurovirulence by 8-fold and 20-fold, respectively, and introduction of both substitutions concurrently into the parental backbone reduced mouse neurovirulence up to 50-fold (Table 4). Furthermore, the ASTs of these mice increased incrementally by the addition of E-$K_{315}$D, NS5-$DR_{654,655}$AA, and E-$K_{315}$D/NS5-$DR_{654,655}$AA, from 8.6 dpi to >21 dpi. Decreases in neurovirulence were also noted in TBEV/DEN4Δ30 viruses containing the single substitutions at E-$K_{315}$D or NS5-$DR_{654,655}$AA, or both substitutions as demonstrated by 4-fold to 487-fold increases in $icLD_{50}$ values. Although no difference in $icLD_{50}$ value was noted between TBEV/DEN4 and TBEV/DEN4Δ30 viruses, mice inoculated with TBEV/DEN4Δ30/E-$K_{315}$D or TBEV/DEN4Δ30/NS5-$DR_{654,655}$AA succumbed to infection approximately two to four days later than mice inoculated with TBEV/DEN4/E-$K_{315}$D or TBEV/DEN4/NS5-$DR_{654,655}$AA (Table 4).

TABLE 4

Neurovirulence phenotypes of chimeric viruses in suckling Swiss mice

| Virus | $LD_{50}$ (pfu) | Fold reduction in neurovirulence compared to parental[a] | AST (days)[b] |
|---|---|---|---|
| TBEV/DEN4 | 0.8 | — | 7.4 |
| TBEV/DEN4/E-$K_{315}$D | 6.6 | 8 | 8.6 |
| TBEV/DEN4/NS5-$DR_{654,655}$AA | 16.2 | 20 | 12.2 |
| TBEV/DEN4/E-$K_{315}$D/NS5-$DR_{654,655}$AA | 40.8 | 51 | >21 |
| TBEV/DEN4Δ30 | 1.0 | — | 7.0 |
| TBEV/DEN4Δ30/E-$K_{315}$D | 4.1 | 4 | 10.3 |
| TBEV/DEN4Δ30/NS5-$DR_{654,655}$AA | 40.7 | 41 | 16 |
| TBEV/DEN4Δ30/E-$K_{315}$D/NS5-$DR_{654,655}$AA | 487 | 487 | >21 |

[a]Parental virus is TBEV/DEN4 for the first set of chimeras or TBEV/DEN4Δ30 for the second set of chimeras.
[b]Average survival times of mice that died after ic inoculation of 10 pfu of indicated virus.

Further analysis of neurovirulence in these mice revealed that introduction of the substitutions at NS5-$DR_{654,655}$AA attenuated the virus for mouse neurovirulence to a greater extent than either the substitution at E-$K_{315}$D or Δ30 alone. While $icLD_{50}$ values of E-$K_{315}$D increased between 4-fold and 8-fold compared to the parental viruses, introduction of NS5-$DR_{654,655}$AA into either the TBEV/DEN4 or TBEV/DEN4Δ30 backbone resulted in a decrease of mouse neurovirulence by 20-fold and 41-fold, respectively (Table 4). In addition, introduction of both Δ30 and NS5-$DR_{654,655}$AA into the TBEV/DEN4 backbone decreased the mouse neurovirulence phenotype compared to TBEV/DEN4/NS5-$DR_{654,655}$AA virus alone by 2.5-fold (40.7 vs. 16.2 pfu) and increased the AST by 4.5 days. Addition of both sets of amino acid substitutions led to an increase in AST by at least 3-fold compared to their parental viruses. While the Δ30 mutation did not alter the mouse neurovirulence phenotype by itself, it acted synergistically with the substitutions at E-$K_{315}$D and NS5-$DR_{654,655}$AA residues to increase the $icLD_{50}$ from 40.8 pfu to 487 pfu, and subsequently decrease mouse neurovirulence by 12-fold (Table 4).

The TBEV/DEN4Δ30 mutant viruses were also assayed for replication in 3- or 5-day-old suckling mouse brains (FIG. 2). Parental unmodified TBEV/DEN4Δ30 virus rapidly reached high viral titers in both sets of mice (between 7.6 and 8.7 $\log_{10}$ PFU) by 5 dpi after ic inoculation. After ic inoculation of 3-day-old mice, TBEV/DEN4Δ30/NS5-$DR_{654,655}$AA and TBEV/DEN4Δ30/E-$K_{315}$D/NS5-$DR_{654,655}$AA chimeric viruses replicated approximately 100-fold less than either the TBEV/DEN4Δ30 parent or TBEV/DEN4Δ30/E-$K_{315}$D virus and attained peak viral titers six days later (FIG. 2A). TBEV/DEN4Δ30/E-$K_{315}$D virus was slightly less attenuated in this age of mice, demonstrating approximately a 10-fold decrease in replication compared to the parental virus.

When the mutant viruses were inoculated ic into brain of 5-day-old mice, they replicated to lower viral titers and attained peak viral titers later than the TBEV/DEN4Δ30 parent. TBEV/DEN4Δ30/E-$K_{315}$D and TBEV/DEN4Δ30/NS5-$DR_{654,655}$AA viruses were similar to each other, as they replicated between 25- and 32-fold less than the TBEV/DEN4Δ30 parental virus, respectively (FIG. 2B). However, TBEV/DEN4Δ30/E-K$_{315}$D/NS5-DR$_{654,655}$AA virus was highly attenuated, as it replicated 20,000-fold less than TBEV/DEN4Δ30 virus, and attained its peak viral titer 12 days later (FIG. 2B). Sequence analysis of mouse brain isolates demonstrated that all of the designed mutations (E-K$_{315}$D, NS5-DR$_{654,655}$AA, and E-K$_{315}$D/NS5-DR$_{654,655}$AA) that were introduced in the chimeric genome were highly stable throughout the time course of the study in 5-day old mice (Table 5).

TABLE 5

Genetic stability of introduced mutations in TBEV/DEN4Δ30 viruses in brains of 5-day-old mice

| Virus[a] | Day of isola-tion[b] | No. tested | No. mutations changed/No. tested[c] | | |
|---|---|---|---|---|---|
| | | | Δ30 | E$_{315}$ | NS5$_{654,655}$ |
| TBEV/DEN4Δ30/E-K$_{315}$D | 8 | 10 | 0/10 | 0/10 | -- |
| | 9 | 2 | 0/2 | 0/2 | -- |
| TBEV/DEN4Δ30/NS5-DR$_{654,655}$AA | 13 | 7 | 0/7 | -- | 0/7 |
| TBEV/DEN4Δ30/E-K$_{315}$D/NS5-DR$_{654,655}$AA | 15 | 2 | 0/2 | 0/2 | 0/2 |
| | 17 | 4 | 0/4 | 0/4 | 0/4 |

[a]Five-day-old mice were inoculated IC with 10$^3$ PFU of indicated virus.
[b]Brains of mice were harvested on indicated day, and virus RNA was isolated from brain homogenate to determine virus genomic sequence.
[c]The virus genome regions encompassing the introduced Δ30, E$_{315}$, or NS5$_{654,655}$ mutations were directly sequenced from brain homogenates to determine stability of the mutations. Dashed lines indicate that no mutation was originally introduced at this position.

In addition to highly reduced neurovirulence in suckling mice, as shown by H&E staining, TBEV/DEN4Δ30/E-K$_{315}$D/NS5-DR$_{654,655}$AA did not cause neuroinflammation in the brains of mice inoculated intracerebrally, unlike TBEV/DEN4 and TBEV/DEN4Δ30 (FIG. 3).

Figure 4:
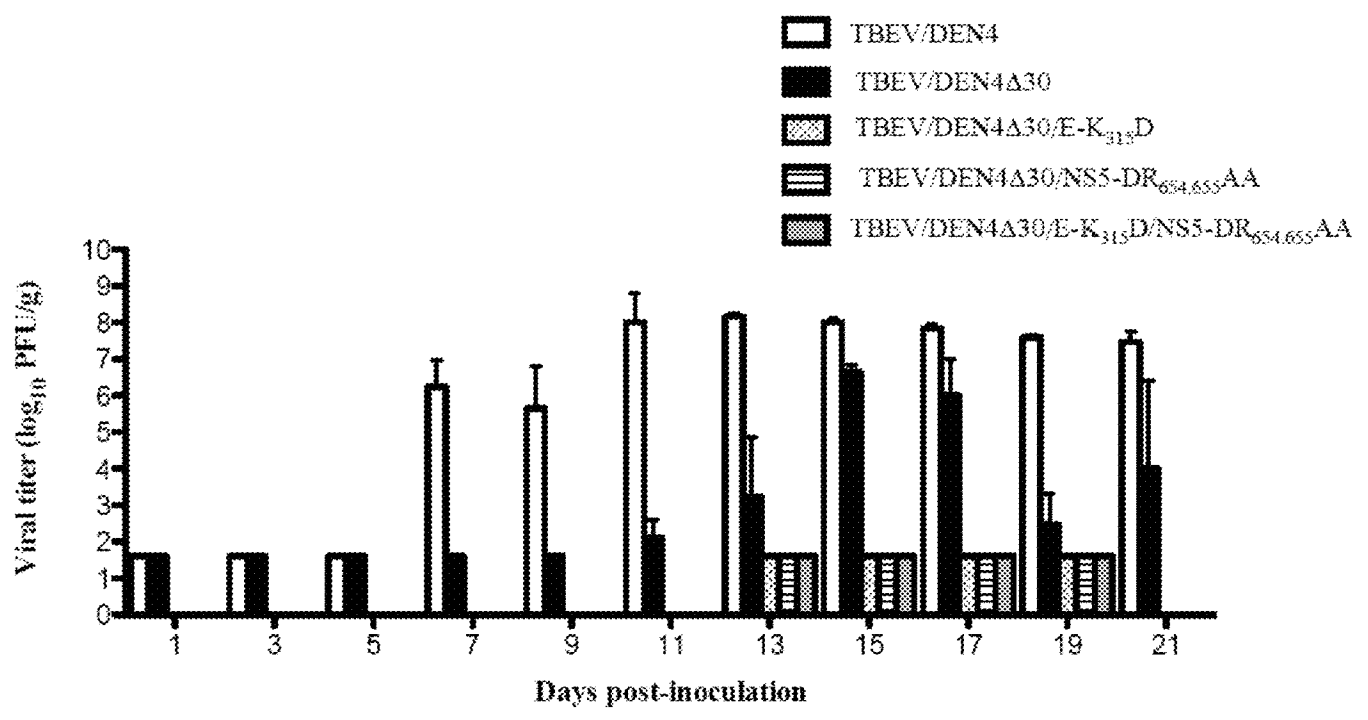

Since the parental TBEV/DEN4 virus is highly attenuated for the ability to travel to the CNS by the ip route in immunocompetent mice (Pletnev et al., *J. Virol.* 67:4956-4963, 1993), the neuroinvasive properties of the modified TBEV/DEN4 viruses was investigated in immunocompromised mice. Groups of at least 10 SCID mice were ip inoculated with 10$^5$ pfu of chimeric virus and AST, morbidity, and viral titers in the brains were assessed. Although introduction of the Δ30 deletion into the TBEV/DEN4 backbone demonstrated little effect on mouse neurovirulence, a decrease in mouse neuroinvasiveness was observed with TBEV/DEN4Δ30 virus, as shown by a reduction of virus-induced encephalitis or mortality (from 60% to 18%) compared to TBEV/DEN4 virus (Table 6). Since addition of the Δ30 mutation significantly reduced TBEV/DEN4 neuroinvasion in immunocompromised mice, the ability of Δ30 in combination with E-K$_{315}$D and/or NS5-DR$_{654,655}$AA substitutions to further reduce this property was investigated. While the combination of E-K$_{315}$D with Δ30 increased the AST and decreased morbidity, introduction of both NS5-DR$_{654,655}$AA and Δ30 in TBEV/DEN4 completely abrogated the ability of the chimeric virus to invade the CNS from the peripheral inoculation site (Table 6). Infectious TBEV/DEN4Δ30/E-K$_{315}$D, TBEV/DEN4Δ30/NS5-DR$_{654,655}$AA, or TBEV/DEN4Δ30/E-K$_{315}$D/NS5-DR$_{654,655}$AA virus could not be recovered from brains of mice that were harvested at 13, 15, or 17 dpi, days at which the unmodified TBEV/DEN4 virus reached a peak virus replication in brains of SCID mice inoculated ic (FIG. 4). These studies demonstrate the neurological safety profile of TBEV/DEN4Δ30/E-K$_{315}$D, TBEV/DEN4Δ30/NS5-DR$_{654,655}$AA, and TBEV/DEN4Δ30/E-K$_{315}$D/NS5-DR$_{654,655}$AA virus.

TABLE 6

Neuroinvasiveness of chimeric viruses in SCID adult mice

| Virus | Dose (pfu) | AST | % mortality |
|---|---|---|---|
| TBEV/DEN4 | 10$^5$ | 23 | 60 |
| TBEV/DEN4Δ30 | 10$^5$ | 22 | 18 |
| TBEV/DEN4Δ30/E-K$_{315}$D | 10$^5$ | 32 | 9 |
| TBEV/DEN4Δ30/NS5-DR$_{654,655}$AA | 10$^5$ | >49 | 0 |
| TBEV/DEN4Δ30/E-K$_{315}$D/NS5-DR$_{654,655}$AA | 10$^5$ | >49 | 0 |

Example 3

Demonstration of Immunoprotective Effect of TBEV/DEN4 Chimeras in Mice

This example demonstrates that TBEV/DEN4 chimeras are immunoprotective for TBEV/DEN4 infection in mice.
Methods In the first experiment, adult Swiss mice were ip inoculated with 10$^5$ pfu of TBEV/DEN4, TBEV/DEN4Δ30, or their respective mutant viruses and challenged via the ic route with 100 icLD$_{50}$ of TBEV/DEN4 28 days later. In the second experiment, six groups of 10 3-week-old Swiss mice were ip inoculated with one or two doses of 10$^5$ pfu of TBEV/DEN4Δ30/E-K$_{315}$D/NS5-DR$_{654,655}$AA or with three doses of the inactivated TBEV vaccine, Encepur® (30 μl per dose, or approximately one mouse protective dose). Three groups of mice were inoculated with two doses of TBEV/DEN4Δ30/E-K$_{315}$D/NS5-DR$_{654,655}$AA on 0 and 21 dpi, whereas another three groups of mice were administered one dose of TBEV/DEN4Δ30/E-K$_{315}$D/NS5-DR$_{654,655}$AA on 21 dpi. The remaining three groups of mice were inoculated with three doses of Encepur® on 0, 7, and 21 dpi, in a schedule comparable to the rapid vaccination schedule in humans. An additional group of 20 mice were ip inoculated with Leibovitz's L-15 medium (Invitrogen) and separated into challenge control groups. On day 48 post-inoculation, all mice were ip inoculated with 100 LD$_{50}$ (10$^2$ pfu) of homologous TBEV strain Sofjin, or heterologous TBEV strain Hypr.

In both sets of experiments, serum was measured for neutralizing antibody titers by the plaque reduction neutralization test (PRNT) 25 days following the last immunization. Briefly, 4-fold serially diluted heat-inactivated sera were combined with TBEV/DEN4Δ30 virus and 10% guinea pig complement (Lonza Inc., Allendale, N.J.), incubated for 1 hour at 37° C., and then added to monolayers of Vero cells in two replicates. Antibody titers were defined as the dilution of serum that neutralized 60% of the virus (PRNT$_{60}$). Seroconversion was defined as a 4-fold increase in serum neutralizing antibody titers compared to the negative controls.

Figures 5A, 5B:
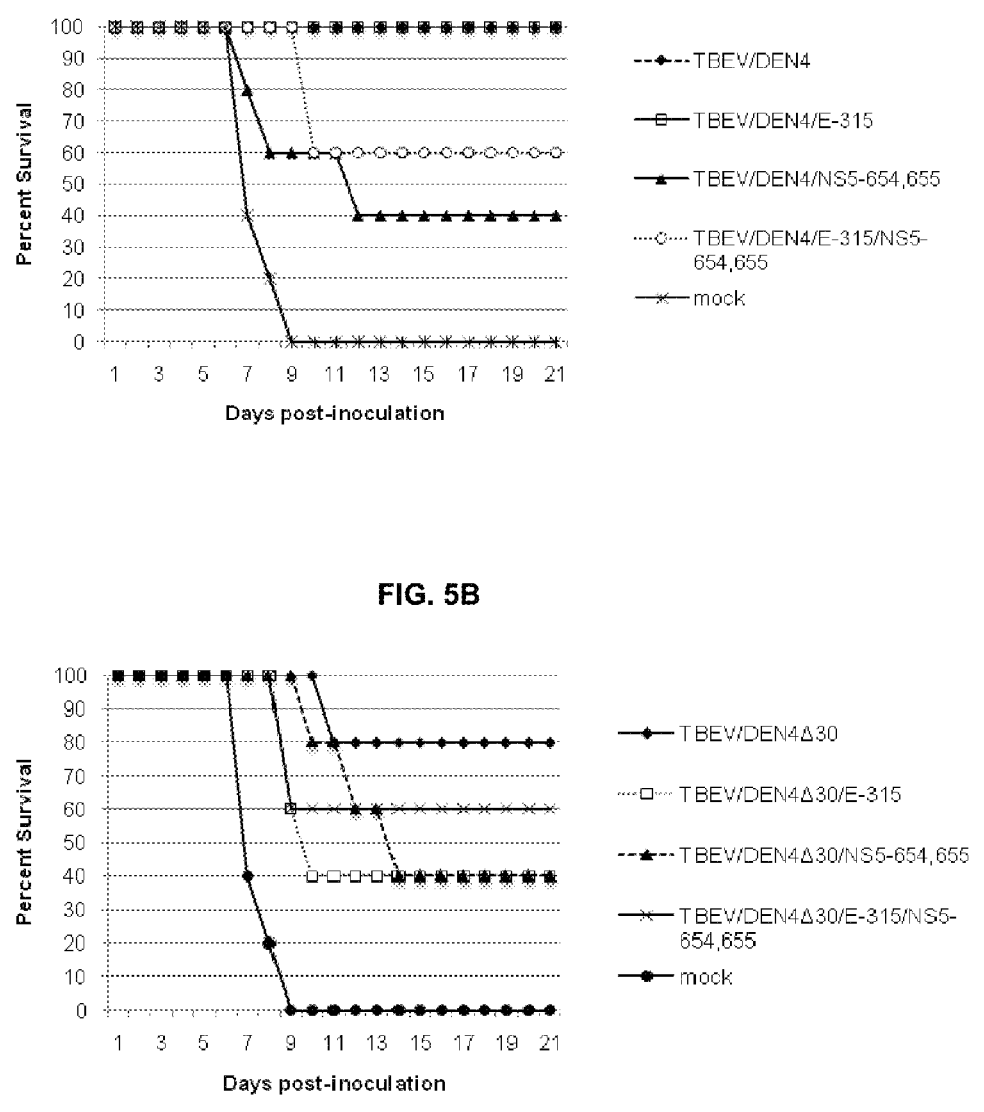

All mice were monitored for signs of morbidity and mortality for 21 days post-challenge (dpc). Moribund mice were euthanized upon observation of symptoms, including paralysis and hemorrhaging. Average survival times (ASTs) were determined by measuring mean survival time of mice that succumbed to infection within 21 dpc.
Results In the first experiment, all control mice succumbed to infection by day 9 post-inoculation following a severe is challenge with TBEV/DEN4 virus. However, TBEV/DEN4 and TBEV/DEN4/E-K$_{315}$D inoculated mice were completely protected against challenge with the lethal dose of TBEV/DEN4 virus, while TBEV/DEN4/NS5-DR$_{654,655}$AA and TBEV/DEN4/E-K$_{315}$D/NS5-DR$_{654,655}$AA viruses induced between 40% and 60% protection for the mice (FIG. 5A). Furthermore, 80% of TBEV/DEN4Δ30 inoculated mice were protected against severe challenge with TBEV/DEN4 virus, while viruses containing E-$K_{315}D$, NS5-$DR_{654,655}AA$, or both substitutions within the TBEV/DEN4Δ30 backbone also provided protection in 40-60% of the mice (FIG. 5B). Mice inoculated with either TBEV/DEN4 or TBEV/DEN4Δ30 mutants exhibited slight delays in death compared to the control groups (FIGS. 5A and 5B). Although these studies demonstrated moderate protection from severe challenge with TBEV/DEN4, neutralizing antibody titers in all groups of mice were low (≤1:20 geometric mean titer) but were similar to each other.

In the second experiment, adult Swiss mice inoculated intraperitoneally also showed that two doses ($10^5$ pfu) of TBEV/DEN4Δ30/E-$K_{315}D$/NS5-$DR_{654,655}AA$ induced (1) comparable levels of TBEV-specific serum neutralizing antibodies to three doses of the inactivated Encepur® vaccine (Novartis) (FIG. 6). Furthermore, similar levels of animals seroconverted when vaccinated either with two doses of TBEV/DEN4Δ30/E-$K_{315}D$/NS5-$DR_{654,655}AA$ or with three doses of Encepur® (50% vs, 68% respectively. Two doses of TBEV/DEN4Δ30/E-$K_{315}D$/NS5-$DR_{654,655}AA$ also demonstrated similar levels of protection compared to three doses of Encepur® after challenge with wild-type homologous TBEV strain Sofjin or heterologous TBEV strain Hypr viruses (Table 7). Overall, these studies demonstrate that the immunogenicity and/or protection of TBEV/DEN4Δ30/E-$K_{315}D$/NS5-$DR_{654,655}AA$ is comparable to that of the inactivated Encepur® vaccine in mice.

TABLE 7

Protection of inoculated mice challenged with wild-type TBEV strains

| Immunizing virus[a] | No. doses | No. animals | Challenge virus[b] | % Survival | AST[d] |
|---|---|---|---|---|---|
| TBEV/DEN4Δ30/E-$K_{315}D$/ | 1 | 10 | Sofjin | 10 | 9.9 |
| NS5-$DR_{654,655}AA$ | 2 | 10 | | 60[§] | 9.8 |
| Encepur ® | 3 | 10 | | 80[§] | 17.0 |
| Mock | | 5 | | 0 | 10.0 |
| TBEV/DEN4Δ30/E-$K_{315}D$/ | 1 | 10 | Hypr | 0 | 10.8 |
| NS5-$DR_{654,655}AA$ | 2 | 10 | | 70[§] | 12.3 |
| Encepur ® | 3 | 10 | | 80[§] | 11.0 |
| Mock | | 5 | | 0 | 10.8 |

[a]Groups of mice were inoculated with one or two doses of $10^5$ pfu TBEV/DEN4Δ30/E-$K_{315}D$/NS5-$DR_{654,655}AA$ virus, or three doses of inactivated Encepur ® vaccine.
[b]Mice were challenged with 100 ip $LD_{50}$ of wild-type viruses on day 48 pi.
[c]Seroconversion was defined as 4-fold increase in neutralizing antibody titer compared to original dilution.
[d]Average survival times of mice that succumbed to disease following challenge with wild-type TBEV.
[§]Significantly different from other groups (Kaplan-Meier, log-rank p < 0.05), but not from each other.
50% animals seroconverted with 2 doses of LA vaccine, 68% animals seroconverted with 3 doses of Encepur ® (no significant difference between the two groups).

Example 4

Demonstration of Protective Effect of Chimeric Viruses in Rhesus Macaques

This example demonstrates that the chimeric TBEV/DEN4 viruses are immunogenic in rhesus macaques and provide a protective effect following challenge.

Methods

The studies in monkeys with the chimeric TBEV vaccine candidates were carried out in the BSL-3 facility at Bioqual, Inc. (Rockville, Md.), in accordance with all state and federal guidelines. All monkeys were seronegative for neutralizing antibodies to TBEV or DEN4 prior to immunization. Groups of 4 rhesus macaques (*Macaca mulatta*) were immunized subcutaneously (sc) with one dose of $10^5$ pfu of chimeric TBEV/DEN4Δ30 virus or its derivatives. One group of 4 monkeys received 3 human doses of an inactivated TBEV vaccine (ENCEPUR®, Chiron/Behring, Germany) in an immunization schedule that is similarly used for humans. One dose was administered on day 0, and monkeys were boosted with inactivated TBEV vaccine on days 7 and 21. Monkeys inoculated with live virus were bled daily under ketamine anesthesia for 9 days to detect and quantitate levels of viremia. Blood was collected from monkeys on 42 dpi to measure levels of TBEV-specific neutralizing antibodies against TBEV/DEN4Δ30, wild-type Far-Eastern TBEV subtype Sofjin, or wild-type Central European TBEV subtype Hypr. All monkeys were challenged sc with $10^5$ pfu of unmodified TBEV/DEN4 virus the following day. Monkeys were bled daily on days 0 to 7 post-challenge (43-50 dpi) to determine levels of viremia and on 21 dpc (64 dpi) for measurement of serum neutralizing antibodies against TBEV/DEN4Δ30. $PRNT_{60}$ assays against TBEV/DEN4Δ30 were done according to the protocol described in Example 3, whereas $PRNT_{60}$ assays against wild-type TBEV were performed using 4-fold serially diluted sera combined with either Sofjin or Hypr virus. The serum:virus mix was incubated at 37° C. for one hour, and then added to confluent monolayers of BHK cells in replicates of two.

Results

Since the TBEV/DEN4Δ30 mutant viruses demonstrated the lowest values for neurovirulence and neuroinvasion compared to TBEV/DEN4 and still provided protection in mice against severe challenge with TBEV/DEN4 virus, these viruses were analyzed for safety, immunogenicity, and protective efficacy in non-human primates. Analysis was performed by investigating levels of viremia and TBEV-specific neutralizing antibody titers, since non-human primates do not exhibit any disease manifestation after peripheral inoculation with unmodified TBEV/DEN4 virus (Rumyantsev et al., *Vaccine* 26:133-143, 2006). Rhesus macaques were sc inoculated with one dose of TBEV/DEN4Δ30 virus or its derivatives, or three doses of the inactivated TBEV vaccine, bled to detect levels of viremia and neutralizing antibody titers, and sc challenged with unmodified TBEV/DEN4 virus. All animals were healthy throughout the study, regardless of the inoculums used.

One animal within the TBEV/DEN4Δ30 group and two animals in the TBEV/DEN4Δ30/E-$K_{315}D$ vaccinated groups exhibited low levels of viremia (≤1.5 $\log_{10}$ pfu/ml) for one to two days, while all remaining monkeys demonstrated no viremia above detectable limits (Table 8). This was in contrast to animals inoculated with TBEV/DEN4 virus, which developed viremia that lasted three to four days and attained a mean peak virus titer of 3.1 $\log_{10}$ pfu/ml. Despite low to no levels of viremia, all animals that received a single dose of any of the modified TBEV/DEN4 viruses seroconverted and had mean TBEV neutralizing antibody titers between 65 to 150, while animals inoculated with either the parental TBEV/DEN4 virus or three doses of the inactivated TBEV vaccine demonstrated higher mean neutralizing antibody titers of 1817 and 899, respectively (Table 8).

Although the modified TBEV/DEN4 viruses induced 6-14-fold lower mean neutralizing titers compared to three doses of the inactivated vaccine, they were still able to provide protection against viremia caused by challenge with TBEV/DEN4 virus. However, mean TBE neutralizing antibody titers after vaccination with any of the TBEV/DEN4Δ30 mutant viruses increased post-challenge, demonstrating the inability of these viruses to completely prevent viral replication after challenge.

TABLE 8

Viremia and serum neutralizing antibodies in rhesus monkeys in response to TBEV/DEN4 chimeras

| Immunizing virus | Rhesus No. | Viremia (log$_{10}$ pfu/ml) on indicated day post-inoculation[a] | | | | | Serum neutr. titer 42 dpi[b] | Viremia (log$_{10}$ pfu/ml) on indicated day post-challenge[c] | | | | | Serum neutr. titer 64 dpi | Serum neutr. titer 84 dpi |
|---|---|---|---|---|---|---|---|---|---|---|---|---|---|---|
| | | 0 | 1 | 2 | 3 | 4 | | 0 | 1 | 2 | 3 | 4 | | |
| TBE/DEN4Δ30 | DC25 | — | — | — | — | — | 120 | — | — | — | — | — | 2175 | 880 |
| | DC44 | — | — | 1.4 | — | — | 203 | — | — | — | — | — | 764 | 286 |
| | DC53 | — | — | — | — | — | 135 | — | — | — | — | — | 1137 | 465 |
| | DC62 | — | — | — | — | — | 152 | — | — | — | — | — | 1623 | 1449 |
| GMT[b] | | | | | | | 150 | | | | | | 1323 | 642 |
| TBE/DEN4Δ30/E-K315D | DC72 | — | — | 1.0 | — | — | 175 | — | — | — | — | — | 454 | 270 |
| | DC81 | — | 0.7 | 1.5 | — | — | 121 | — | — | — | — | — | 363 | 301 |
| | DC1L | — | — | — | — | — | 40 | — | — | — | — | — | 826 | 679 |
| | DC2J | — | — | — | — | — | 52 | — | — | — | — | — | 3692 | 1663 |
| GMT | | | | | | | 82 | | | | | | 842 | 550 |
| TBE/DEN4Δ30/NS5-DR$_{654,655}$AA | DCR1 | — | — | — | — | — | 97 | — | — | — | — | — | 1795 | 661 |
| | FIC | — | — | — | — | — | 61 | — | — | — | — | — | 1014 | 613 |
| | FID | — | — | — | — | — | 81 | — | — | — | — | — | 284 | 317 |
| | BZH | — | — | — | — | — | 53 | — | — | — | — | — | 453 | 223 |
| GMT | | | | | | | 71 | | | | | | 696 | 411 |
| TBE/DEN4Δ30/E-K315D/NS5-DR$_{654,655}$AA clone A | F78 | — | — | — | — | — | 65 | — | — | — | — | — | 961 | 457 |
| | DBV3 | — | — | — | — | — | 102 | — | — | — | — | — | 519 | 221 |
| | DBVF | — | — | — | — | — | 17 | — | — | — | — | — | 776 | 125 |
| | DBVW | — | — | — | — | — | 152 | — | — | — | — | — | 2052 | 574 |
| GMT | | | | | | | 65 | | | | | | 944 | 292 |
| Inactivated TBEV vaccine (3 doses) | C70 | — | — | — | — | — | 624 | — | — | — | — | — | 2407 | 1718 |
| | DBW8 | — | — | — | — | — | 400 | — | — | — | — | — | 413 | 387 |
| | DBPD | — | — | — | — | — | 2399 | — | — | — | — | — | 1537 | 1670 |
| | DBPF | — | — | — | — | — | 1090 | — | — | — | — | — | 456 | 96 |
| GMT | | | | | | | 899 | | | | | | 914 | 571 |
| Mock | DB1N | — | — | — | — | — | <2 | — | 2.7 | 2.3 | 1.7 | 1.0 | 1136 | 4374 |
| | DBRI | — | — | — | — | — | <2 | — | 1.8 | 3.3 | 1.0 | — | 1287 | 3380 |
| | DBC7 | — | — | — | — | — | <2 | — | — | 0.7 | 1.8 | — | 5946 | 4262 |
| | A5E071 | — | — | — | — | — | <2 | — | — | 2.3 | — | — | 1254 | 1652 |
| GMT | | | | | | | <2 | | | | | | 1817 | 3194 |

[a]Dashed lines (—) indicate serum viral titers below the limit of detection (<0.7 log$_{10}$ pfu/ml) in Vero cells. Serum viral titers were measured 0-8 days post-immunization or 0-7 days post-challenge. Viral titers in all groups were below the limit of detection 3-8 days post-immunization and 5-7 days post-challenge and are not shown.
[b]Plaque reduction (60%) neutralizing antibody titer was determined against TBEV/DEN4Δ30 virus using serum collected on indicated day post-immunization. Reciprocal titers are shown; geometric titers (GMT) are calculated for each group.
[c]Monkeys were challenged sc with 10$^5$ pfu of TBEV/DEN4 virus 43 days post-immunization.

Serum neutralizing antibody titers in rhesus monkeys against Sofjin and Hypr viruses were similar between groups of monkeys inoculated with one dose (10$^5$ pfu) of TBE/DEN4Δ30/E-K$_{315}$D/NS5-DR$_{654,655}$AA and three doses of Encepur® vaccine (Table 9). Overall these studies demonstrate that immunogenicity and/or protection by TBE/DEN4Δ30/E-K$_{315}$D/NS5-DR$_{654,655}$AA is comparable to that of the inactivated Encepur® vaccine in monkeys.

TABLE 9

Immunogenicity of rhesus monkeys against homologous or heterologous wild-type TBEV following vaccination

| Immunizing virus[a] | Rhesus no. | Serum neutralizing antibody titer[b] | |
|---|---|---|---|
| | | α-Sofjin | α-Hypr |
| TBE/DEN4Δ30 | DC25 | 17 | 11 |
| | DC44 | 79 | 58 |
| | DC53 | 22 | 26 |
| | DC62 | 21 | 32 |
| GMT | | 28 | 27 |
| TBE/DEN4Δ30/E-K$_{315}$D/NS5-DR$_{654,655}$AA | F78 | 7 | 19 |
| | DBV3 | 37 | <5 |
| | DBVF | 13 | <5 |
| | DBVW | 46 | 93 |
| GMT | | 20 | 13 |
| Encepur | C70 | 11 | 27 |

TABLE 9-continued

Immunogenicity of rhesus monkeys against homologous
or heterologous wild-type TBEV following vaccination

| Immunizing virus[a] | Rhesus no. | Serum neutralizing antibody titer[b] | |
|---|---|---|---|
| | | α-Sofjin | α-Hypr |
| 3 doses | DBW8 | 12 | 46 |
| | DBPD | 52 | 273 |
| | DBPF | 37 | 105 |
| GMT | | 22 | 77 |

[a]Groups of four monkeys were inoculated SC with one dose of 5.0 log$_{10}$ PFU of TBEV/DEN4Δ30 or TBEV/DEN4Δ30 Δ30/E$_{315}$/NS5$_{654,655}$, or inoculated sc with three doses of 0.5 ml of Encepur ® vaccine.
[b]Serum was harvested from monkeys on day 42 pi, prior to TBEV/DEN4 virus challenge. Serum plaque reduction (60%) neutralizing antibody titers were determined against wild-type Far-Eastern strain Sofjin or Central European strain Hypr. Reciprocal titers are shown; geometric mean titers (GMT) are calculated for each group. No significant differences were observed between serum neutralizing antibody titer groups (p > 0.05, one-way ANOVA).

Example 5

Virus Infection in Mosquitoes and Ticks

This Example demonstrates the inability of the TBEV/DEN4Δ30 chimeric viruses to infect and replicate mosquitoes and ticks.

Methods

Virus Infection in Mosquito and Tick Cell Culture. To investigate the viral kinetics in cell culture, confluent monolayers of Vero or *Aedes albopictus* C6/36 cells were infected at a multiplicity of infection (MOI) of 1 for 1 hr at 37° C. or 32° C., respectively, and maintenance media was added. Virus supernatant was harvested from the cell culture every 24 hr for 8 days and frozen at −80° C. until it could be titrated by immunofocus assay. After harvesting the supernatant, fresh media was added. To determine viral titers, confluent monolayers of Vero cells in 24- or 48-well plates were infected with 10-fold serial dilutions of virus, incubated at 37° C. for 1 hr, and were overlaid with Opti-MEM I containing 1% methylcellulose (Invitrogen), 2% heat-inactivated FBS, 4 mM L-glutamine, and 0.05 mg/ml of gentamycin. After incubation for 6 days at 32° C., the cells were fixed for 20 min with 100% methanol, and plaques were visualized by immunostaining with hyperimmune mouse ascitic fluid specific for both TBEV and LGT virus (Russian Spring Summer Encephalitis (RSSE) VR79; ATCC) and peroxidase-labeled polymer conjugated to anti-mouse immunoglobulin (Dako Co., Carpinteria, Calif.). Mean viral titers from each time point were determined from three replicates.

To investigate the ability of the viruses to infect and replicate in tick cells, infection of *Ixodes scapularis* ISE6 cells was undertaken. Infection of simian Vero cells was used as a positive control. For ISE6 cells, all viruses were serially passaged three times following an initial infection of ISE6 cells with virus. Confluent monolayers of ISE6 tick or Vero cells were initially infected with virus at a MOI of 1, and cells were incubated at 34° C. or 37° C., respectively, for 1 hr. Maintenance media was added following incubation and ⅓ volume of the virus supernatant was obtained from infected cells after 7 days; the supernatant was then used to infect fresh ISE6 cells. The infected cells were stained for viral antigen by immunofluorescence or used to extract viral RNA following all three passages with virus.

Detection of Viral Antigen in Cell Culture. After 5 days (Vero cells) or 7 days (ISE6 cells), cells were assayed for infection by immunofluorescence. Slides were prepared by cytocentrifugation of 5×10$^4$ cells followed by fixation in 100% acetone for 30 min. The slides were blocked with PBS containing 2% normal goat serum (NGS) and 1% bovine serum albumin (BSA) for 30 min at room temperature. The primary antibody was a cocktail containing the polyclonal mouse antibody cross-reactive to TBEV and LGT virus (RSSE), and DEN4 virus antiserum (hyperimmune mouse ascites fluid, HMAF). Both antibodies were diluted at 1:1000 in blocking buffer. Following application of the primary antibody, the slides were incubated for 1 hr at 37° C. and were washed with PBS containing 0.5% Tween-20 (PBS-T). Secondary antibody (goat anti-mouse IgG conjugated with Alexa Fluor® 488 (Invitrogen)) was applied at a 1:500 dilution in blocking buffer and incubated for 1 hr at 37° C. The slides were washed in PBS-T and coverslips were mounted using ProLong® Gold antifade reagent (Invitrogen) with 4'6-diamidino-2-phenylindole (DAPI; Invitrogen). Images were captured using an Olympus BX51 microscope with an Olympus DP70 camera and Microsuite software.

Virus Infection in Mosquitoes. *Aedes aegypti* mosquitoes were reared at 27° C. in 70% relative humidity with a 16-hr daylight cycle for use in oral infection. For oral infection of mosquitoes, 10$^6$ pfu/ml of each virus was mixed separately with defibrinated rabbit red blood cells (Spring Valley Laboratories, Woodline, Md.) containing 2.5% sucrose. Five-day-old female *Ae. aegypti* mosquitoes that had been deprived of a sugar source for 24 hr were exposed to the virus bloodmeal for 25 min. The infected bloodmeal was prepared immediately prior to feeding and was offered to mosquitoes in a 37° C. preheated water-jacketed feeder covered in stretched Parafilm®. Fully engorged mosquitoes were transferred to a new container by aspirator and maintained as described above for either 14 or 21 days post-infection (dpi). Throughout the study, the mosquitoes were allowed continuous access to a cotton pad soaked in a solution of 10% sucrose. After 14 or 21 days, mosquitoes were harvested and stored at −80° C. until dissection.

To assess virus infection of mosquitoes, the bodies of mosquitoes were first separated from the legs and heads and then separately triturated in 250 µl Hanks balanced salt solution (HBSS) (Invitrogen) supplemented with 10% FBS, 250 µg/ml amphotericin, 1% ciprofloxacin, and 150 mg/ml clindamycin. To address the efficiency of viral dissemination, individual mosquito heads were also triturated in 250 µl HBSS containing FBS, amphotericin, ciprofloxacin, and clindamycin. Virus titers of heads and bodies were determined in Vero cells by immunofocus assay, as described above.

Virus Infection in Ticks. *I. scapularis* adult females with egg sacs (Oklahoma State University, Stillwater, Okla.) were housed in a relative humidity of 98% with a 16-hr daylight cycle for oviposition and larvae emergence. The larvae were used within 6 months of emergence.

Infection of ticks was by the immersion method. Briefly, 60 larvae per group were collected in a sterile 1.5 ml screw cap centrifuge tube and pretreated by exposure to a reduced relative humidity. To virally infect ticks, the larvae were then immersed in 0.5 ml of complete medium containing 10$^6$ pfu/ml of virus and incubated at 34° C. for 45 min. Following immersion, the ticks were washed twice with cold PBS. Larvae were wicked free of excess moisture using tapered strips of Whatman® paper and maintained at a relative humidity of 98% for 21 and 45 days post-immersion (dpim).

Detection of Viral RNA from Cell Culture or Whole Ticks. Total RNA was isolated from Vero and ISE6 cells using the RNeasy® mini kit (Qiagen, Valencia, Calif.). Cell pellets were resuspended in 350 µl of Buffer RLT and were homogenized by passing through a QIAshredder spin column (Qiagen). RNA was eluted in 50 µl of RNase-free water.

To isolate total RNA from ticks, a group of 25 ticks were homogenized using one of two methods. In the first method, ticks were frozen in liquid nitrogen and triturated with mortar and pestle. The powder was resuspended in 250 µl of Buffer RLT and passed through a QIAshredder spin column. For the second method, ticks were frozen in liquid nitrogen and transferred to Lysing Matrix D tubes (MPBio, Solon, Ohio) containing 800 μl of RLT buffer (Qiagen RNeasy® kit). The ticks were homogenized using the Fastprep® 24 (MPBio) set at speed level 6 m/s for 40 s. The homogenate was clarified by centrifugation at 21,000×g for 3 min. For both methods, RNA from the homogenates was purified using an RNeasy® mini kit (Qiagen). The RNA was eluted in 35 μl of RNase-free water.

Viral RNA from cell culture and ticks was detected using SuperScript® III One-Step RT-PCR System with Platinum® Taq DNA Polymerase (Invitrogen) and primers that were specific for positive- or negative-sense RNA. The RNA was first reversed transcribed at 55° C. for 30 min, followed by routine PCR conditions (40 cycles of denaturing at 94° C. for 1 min, annealing at 55-69° C. for 45 s, and extending at 68° C. for 3 min). The primers used in the reactions are listed in Table 10, and were specific to DEN4, TBE (Sofjin), LGT, or LGT/DEN4 only. The PCR amplicons were examined on a precast 1.2% agarose gel (Lonza).

TABLE 10

Primers used for RT-PCR of negative- and positive-sense RNA

| Virus | | Primer Sequence | SEQ ID |
|---|---|---|---|
| DEN4 (+ Sense Strand)[a] | 5' Primer | CCAGAGTCCCCAGCGAGACTAG | 13 |
| | 3' Primer | GCCAAGGGGTAGAGACCTGAC | 14 |
| DEN4 (− Sense Strand)[a] | 5' Primer | CTCCATGACGCCACACAACCCATGTC | 15 |
| | 3' Primer | CTCAGAAACCCAGGATTCGCGCTCTTGG | 16 |
| TBE (+ Sense Strand)[b] | 5' Primer | GCCACAGTGCGGAAGGAAAGAG | 17 |
| | 3' Primer | GGATCTTGGGCAAGAACCCCACTC | 18 |
| TBE (− Sense Strand)[b] | 5' Primer | CACCGCCAAGAACTGTGTGCA | 19 |
| | 3' Primer | GACCGTGGAAAGTGTGGTGAC | 20 |
| LGT (+ Sense Strand)[c] | 5' Primer | CAGCGACTGTGATTGTGGATATTC | 21 |
| | 3' Primer | AAGGTTGGGTTCCTCATGTTCAAGC | 22 |
| LGT (− Sense Strand)[c, d] | 5' Primer | ACTGGCCGGTAGAAACAGCTT | 23 |
| | 3' Primer | AAGGTTGGGTTCCTCATGTTCAAGC | 24 |
| LGT/DEN (−Sense Strand)[c, e] | 5' Primer | CGCTCCTCCCAGGACGGTGTGC | 25 |
| | 3' Primer | GCGTCGAGATGCACCCACCTGGA | 26 |

Figure 8:
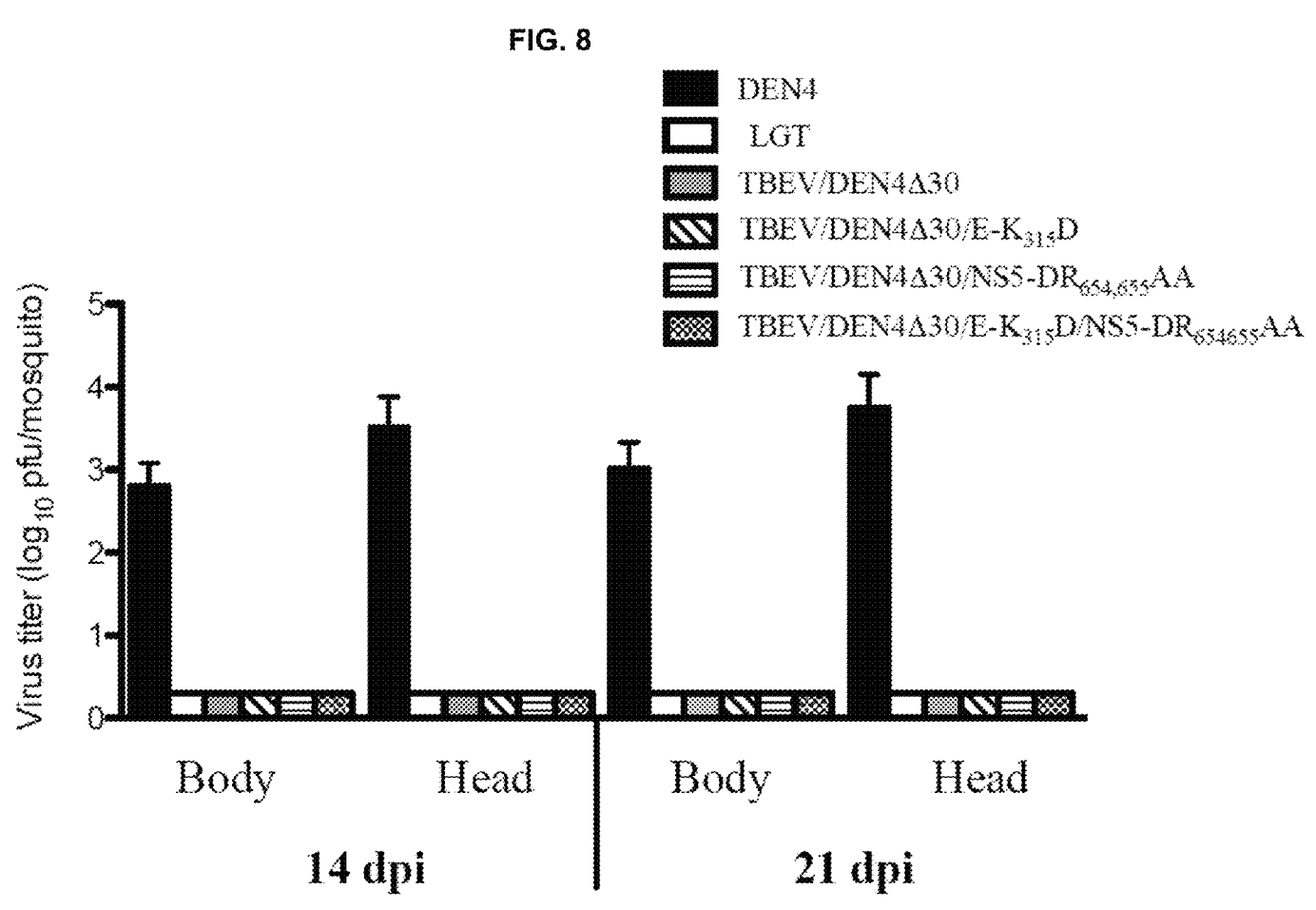
Figures 9A, 9B:
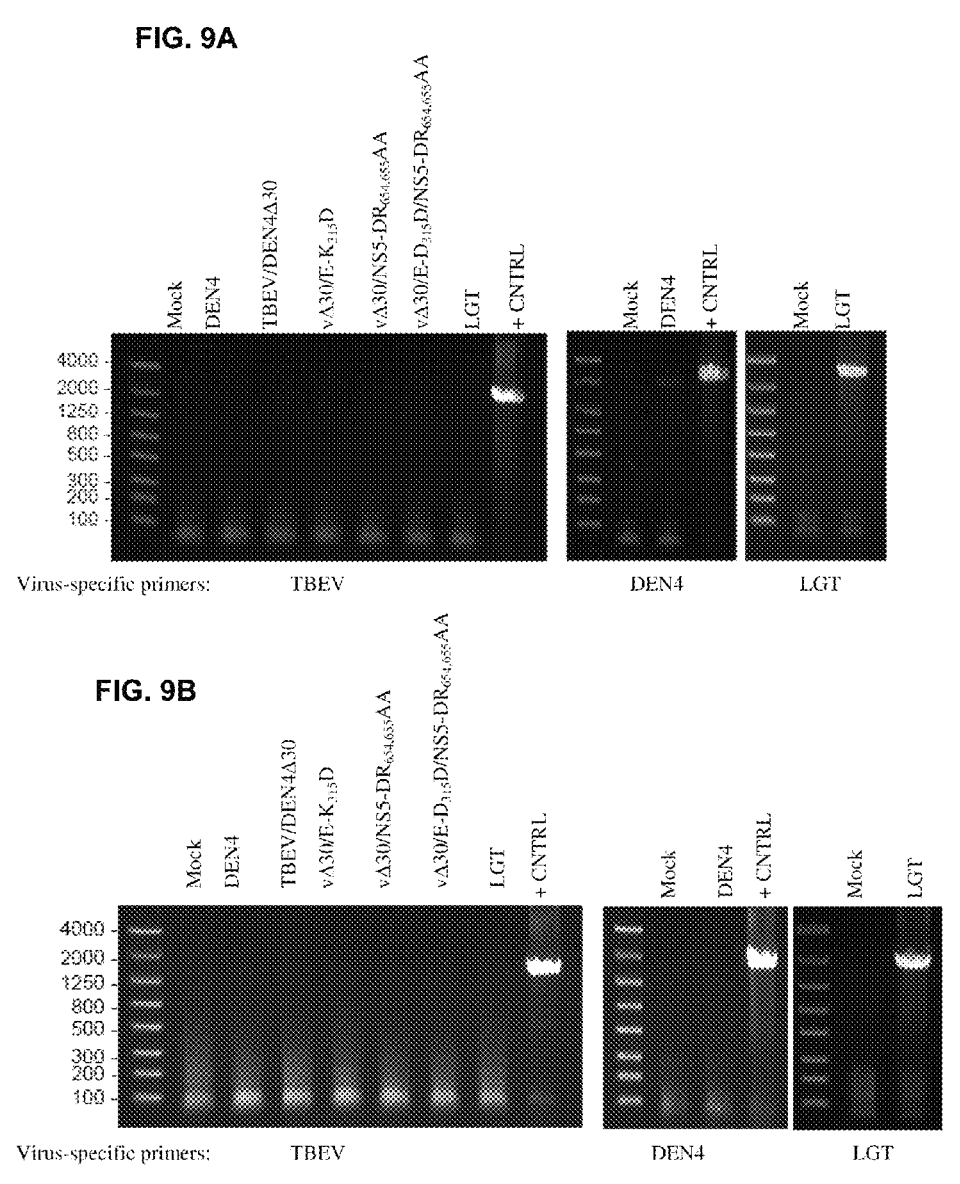

[a]Sequence of DEN4 vector p4 (Genbank Accession No. AY648301)
[b]Sequence of TBEV Sofjin strain (Genbank Accession No. X07755)
[c]Sequence of LGTV TP21 strain (Genbank Accession No. AF253419)
[d]Negative-sense primer used to detect LGTV infection
[e]Negative-sense primer used to detect LGTV/DEN4 infection Results The ability of TBEV/DEN4Δ30 chimeric viruses to infect and replicate in tick and mosquito cell culture, as well as *Ixodes scapularis* ticks and *Aedes aegypti* mosquitoes (arthropod vectors that are able to transmit TBEV and DEN4 virus, respectively) was investigated. Although the chimeric viruses were able to moderately replicate in mosquito cell culture (FIG. 7), they were unable to infect, replicate, or disseminate in *Ae. aegypti* mosquitoes (Table 11, FIG. 8). In addition, the chimeric viruses were unable to infect tick cells, as shown by absence of viral antigen and absence of virus RNA following passage in cells (Table 12). Furthermore, the chimeric viruses were unable to infect or replicate in *I. scapularis* ticks (FIG. 9). These studies demonstrate the environmental safety profile of the vaccine candidates, including TBEV/DEN4Δ30/E-$K_{315}$D/NS5-$DR_{654,655}$AA.

TABLE 11

Infection and dissemination rates of TBEV/DEN4Δ30 chimeras, DEN4, and LGT viruses in mosquitoes

| | 14 dpi | | 21 dpi | |
|---|---|---|---|---|
| Virus[a] | No. infected (% positive)[b] | No. disseminated (% positive)[c] | No. infected (% positive)[b] | No. disseminated (% positive)[c] |
| DEN4 | 16/18 (89) | 13/16 (81) | 15/18 (83) | 15/15 (100) |
| TBEV/DEN4Δ30 | 0/18 (0) | 0/18 (0) | 0/18 (0) | 0/18 (0) |
| TBEV/DEN4Δ30/E-$K_{315}$D | 0/18 (0) | 0/18 (0) | 0/18 (0) | 0/18 (0) |
| TBEV/DEN4Δ30/NS5-$DR_{654,655}$AA | 0/18 (0) | 0/18 (0) | 0/18 (0) | 0/18 (0) |
| TBEV/DEN4Δ30/E-$K_{315}$D/NS5-$DR_{654,655}$AA | 0/18 (0) | 0/18 (0) | 0/18 (0) | 0/18 (0) |
| LGT | 0/18 (0) | 0/18 (0) | 0/18 (0) | 0/18 (0) |

[a]*Ae. aegypti* mosquitoes were orally infected with the indicated viruses and incubated for 14 or 21 dpi. Mosquito bodies and heads were separated, triturated, and titered in Vero cells to determine infectivity and dissemination rates.
[b]Infection rates were measured by the presence of virus in the bodies of mosquitoes compared to the number of mosquitoes tested.
[c]Dissemination rates were measured by the presence of virus in the heads of mosquitoes compared to the number of mosquitoes tested.

TABLE 12

Detection of viral RNA in ISE6 cells during three serial passages

| Virus | Passage 1[a] | | Passage 2[a] | | Passage 3[a] | |
|---|---|---|---|---|---|---|
| | Positive[b] | Negative[b] | Positive[b] | Negative[b] | Positive[b] | Negative[b] |
| LGT | + | + | + | + | + | + |
| DEN4 | + | − | − | − | − | − |
| TBEV/DEN4Δ30 | + | + | − | − | − | − |
| TBEV/DEN4Δ30/E-$K_{315}D$ | + | + | − | − | − | − |
| TBEV/DEN4Δ30/NS5-$DR_{654,655}AA$ | + | + | − | − | − | − |
| TBEV/DEN4Δ30/E-$K_{315}D$/NS5-$DR_{654,655}AA$ | − | − | − | − | − | − |

[a]Presence and absence of viral RNA is denoted by + or −, respectively.
[b]Positive- or negative-sense RNA detection by RT-PCR.

Example 6

Vaccination of Human Subjects with Recombinant TBEV/DEN4Δ30 Chimeric Viruses This example describes evaluation of candidate TBEV/DEN4 chimeric virus vaccines in human subjects.

The safety and efficacy of the disclosed recombinant TBEV/DEN4 chimeras can be evaluated in human volunteers according to procedures well known in the art (e.g., Wright et al., Vaccine, 26:882-890, 2008). For example, eligibility criteria can include: age 18-50 years; no history of chronic illness; normal findings during physical examination; negative (<1:10) for serum neutralizing antibodies to Powassan, Langat, TBEV, West Nile virus, dengue virus types 1-4, and yellow fever virus; negative for antibodies to Saint Louis encephalitis virus and Japanese encephalitis virus by hemagglutination-inhibition (titer <1:10); negative human immunodeficiency virus antibody test and hepatitis C virus antibody test; negative for hepatitis B surface antigen; normal hematologic and hepatic values; and normal urinalysis. Female volunteers should have a negative result on a urine pregnancy test prior to vaccinations and on the days of vaccination and agree to use contraception or abstain from sexual intercourse for the duration of the study. Human volunteers may be selected from those at risk of infection with TBEV, such as individuals residing in areas where TBEV is endemic.

In this example, human volunteers are injected with candidate TBEV/DEN4Δ30 chimeric vaccines subcutaneously at an appropriate dose. The appropriate dose is the dose approved by the FDA, and can be determined from suitable animal studies conducted prior to human vaccination trials (such as those described in Examples 2 and 3). Other routes of administration are possible, including intramuscular and intravenous. The vaccine can be administered as a single dose, or given in multiple doses, such as two, three or four doses. When administered in multiple doses, the booster doses can be administered at various time intervals, such as months to years. Serum samples can be obtained to determine neutralizing antibody titers and identify responders and non-responders to the vaccine.

The initial phase of the study is a double-blind placebo controlled trial in which volunteers are randomly assigned to receive the vaccine or placebo (e.g., in a 4:1 ratio). Volunteers are enrolled in a step-wise manner: a first set of volunteers (such as 3-5 subjects) are initially enrolled; after study day 21, all safety data is reviewed by the medical monitor before proceeding with enrollment of the next set of volunteers (such as about 8-12 subjects); and the set of safety data collected for these volunteers is then reviewed by the medical monitor before enrollment of the remaining volunteers (such as 12-20 subjects). Randomization is done such that no more than 1 volunteer in the first group of volunteers and no more than 4 volunteers in the second group of volunteers receive placebo. Volunteers are observed 30 min after vaccination for any immediate reaction to the vaccine. They are given a diary card and a digital oral thermometer to record their temperature 3 times daily for 19 days. Volunteers return to the clinic every other day for 16 days after vaccination and on study days 19, 21, 28, 42, and 180. A clinical assessment is done at each visit and blood is obtained for hematological and clinical chemistry testing and for virologic or immunologic analysis. Serum is titrated for vaccine virus and for neutralizing antibody.

After completion of initial vaccination, the study may be modified to include a second dose to assess the response of vaccinees to a booster dose. Six to 18 months after initial vaccination the volunteers are re-randomized to receive either vaccine or the placebo control (vaccine diluent) (Wright et al., Vaccine, 26:882-90, 2008; McArthur et al., Am. J. Trop. Med. Hyg. 79:678-84, 2008; Durbin et al., Hum Vaccin., 2:255-60, 2006; Durbin et al., Hum Vaccin., 2:167-73, 2006; Durbin et al., J Infect Dis., 191:710-8, 2005).

In view of the many possible embodiments to which the principles of the disclosure may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A recombinant chimeric virus comprising:
   a first nucleic acid molecule comprising:
   a 5' non-coding region from a dengue type 4 virus;
   a nucleic acid encoding non-structural proteins from a dengue type 4 virus,
   wherein nonstructural protein NS4B comprises a phenylalanine at amino acid position 112 corresponding to amino acid position 2359 of SEQ ID NO: 2, and nonstructural protein NS5 comprises an alanine at amino acid position 654 corresponding to amino acid position 3146 of SEQ ID NO: 2 and an alanine at amino acid position 655 corresponding to amino acid position 3147 of SEQ ID NO: 2; and
   a 3' non-coding region from a dengue type 4 virus, wherein the 3' non-coding region comprises a deletion of nucleotides corresponding to nucleotides 10478-10507 of SEQ ID NO: 27; and
   a second nucleic acid molecule operably linked to the first nucleic acid molecule, the second nucleic acid molecule encoding:
   a prM protein from a tick borne encephalitis virus; and
   an E protein from a tick borne encephalitis virus, wherein the E protein comprises an amino acid substitution from wild-type at amino acid position 315 corresponding to amino acid position 598 of SEQ ID NO: 2 and a tryptophan at amino acid position 240 corresponding to amino acid position 523 of SEQ ID NO: 2,
   wherein the chimeric virus does not encode a C protein.

2. The recombinant chimeric virus of claim 1, wherein the amino acid substitution at amino acid position 315 of the E protein is selected from the group consisting of aspartic acid, alanine, phenylalanine, leucine, serine, arginine, threonine, tryptophan, valine, and tyrosine.

3. The recombinant chimeric virus of claim 1, further comprising an amino acid substitution at amino acid position 84 of the E protein corresponding to amino acid position 367 of SEQ ID NO: 2.

4. The recombinant chimeric virus of claim 1, further comprising an amino acid substitution at amino acid position 6 of nonstructural protein NS1 corresponding to amino acid position 785 of SEQ ID NO: 2.

5. The recombinant chimeric virus of claim 1, wherein the tick-borne encephalitis virus is selected from the group consisting of Central European, Siberian, and Far Eastern subtype.

6. An immunogenic composition comprising the recombinant chimeric virus of claim 1 and a pharmaceutically acceptable carrier.

7. A method of eliciting an immune response to a tick-borne encephalitis virus or a member of the tick-borne encephalitis virus complex in a subject, comprising:
producing a replication-deficient chimeric TBEV/DEN4 virus, comprising transfecting a cell line producing a dengue virus type 4 C protein with the recombinant chimeric virus of claim 1, thereby producing the replication-deficient chimeric TBEV/DEN4 virus; and
administering a therapeutically effective amount of the replication deficient TBEV/DEN4 virus to the subject.

8. The method of claim 7, wherein the member of the tick-borne encephalitis virus complex is Omsk hemorrhagic fever virus, Kyasanur forest disease virus, Langat virus, Louping ill virus, Negishi virus, or Powassan virus.

9. The method of claim 7, further comprising selecting a subject in need of enhanced immunity to tick-borne encephalitis virus or tick-borne encephalitis virus complex.

10. The method of claim 7, further comprising administering to the subject an immunogenic composition for one or more additional flaviviruses.

11. A method of eliciting an immune response to a tick-borne encephalitis virus or a member of the tick-borne encephalitis virus complex in a subject, comprising administering to the subject a therapeutically effective amount of the recombinant chimeric virus of claim 1, and a nucleic acid encoding a dengue virus type 4 C protein.

12. The method of claim 11, wherein the member of the tick-borne encephalitis virus complex is Omsk hemorrhagic fever virus, Kyasanur forest disease virus, Langat virus, Louping ill virus, Negishi virus, or Powassan virus.

13. The method of claim 11, further comprising selecting a subject in need of enhanced immunity to tick-borne encephalitis virus or tick-borne encephalitis virus complex.

14. The method of claim 11, further comprising administering to the subject an immunogenic composition for one or more additional flaviviruses.

* * * * *